US012715902B2

(12) United States Patent
Kammula et al.

(10) Patent No.: US 12,715,902 B2
(45) Date of Patent: Aug. 25, 2026

(54) T CELL RECEPTORS TARGETING DEFECTIVE DNA REPAIR PROTEINS

(71) Applicant: University of Pittsburgh—Of the Commonwealth System of Higher Education, Pittsburgh, PA (US)

(72) Inventors: Udai Shankar Kammula, Pittsburgh, PA (US); Ghanshyam Singh Yadav, Pittsburgh, PA (US); Chetana Bhaskarla, Pittsburgh, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 996 days.

(21) Appl. No.: 17/795,573

(22) PCT Filed: Feb. 5, 2021

(86) PCT No.: PCT/US2021/016883

§ 371 (c)(1),
(2) Date: Jul. 27, 2022

(87) PCT Pub. No.: WO2021/158962

PCT Pub. Date: Aug. 12, 2021

(65) Prior Publication Data

US 2023/0348557 A1 Nov. 2, 2023

Related U.S. Application Data

(60) Provisional application No. 62/971,057, filed on Feb. 6, 2020.

(51) Int. Cl.

| | |
|---|---|
| ***C07K 14/725*** | (2006.01) |
| ***A61P 35/00*** | (2006.01) |
| ***C07K 14/705*** | (2006.01) |
| ***C12N 5/0783*** | (2010.01) |
| ***C12N 15/86*** | (2006.01) |

(52) U.S. Cl.

CPC .......... *C07K 14/7051* (2013.01); *A61P 35/00* (2018.01); *C12N 5/0636* (2013.01); *C12N 15/86* (2013.01)

(58) Field of Classification Search

CPC .. C07K 14/7051; C12N 5/0636; C12N 15/86; A61P 35/00; A61K 40/11; A61K 40/32; A61K 40/42

See application file for complete search history.

(56) References Cited

U.S. PATENT DOCUMENTS

| | | | |
|---|---|---|---|
| 2008/0219956 | A1 | 9/2008 | Russell et al. |
| 2013/0164746 | A1 | 6/2013 | Rossi et al. |
| 2015/0307585 | A1 | 10/2015 | Blankenstein et al. |
| 2019/0233498 | A1 | 8/2019 | Loomis et al. |
| 2019/0233522 | A1 | 8/2019 | Forssmann et al. |
| 2019/0241667 | A1 | 8/2019 | Papadopoulos et al. |
| 2023/0031784 | A1 | 2/2023 | Kammula et al. |

FOREIGN PATENT DOCUMENTS

| | | |
|---|---|---|
| WO | WO 1998/022143 | 5/1998 |
| WO | WO 1998/046778 | 10/1998 |
| WO | WO 2000/017376 | 3/2000 |
| WO | WO 2016/156478 | 10/2016 |
| WO | WO 2017/193104 | 11/2017 |
| WO | WO 2019/099689 A1 | 5/2019 |
| WO | WO 2019/195576 A1 | 10/2019 |
| WO | WO 2019/196088 A1 | 10/2019 |
| WO | WO 2019/199945 | 10/2019 |

OTHER PUBLICATIONS

Choi M et al. ATM mutations in cancer: Therapeutic implications. Mol Cancer Ther. 2016, 15(8):1781-1791. (Year: 2016).*

Stankovic T et al. Ataxia telangiectasia mutated-deficient B-cell chronic lymphocytic leukemia occurs in pregerminal center cells and results in defective damage response and unrepaired chromosome damage. Blood, 2002, 99(1):300-309. (Year: 2002).*

Bitler et al., "ARIDIA-mutated ovarian cancers depend on HDAC6 activity," Nat. Cell Biol., Aug. 2019, 19(8):962-973, 30 pages.

Choi et al., "ATM Mutations in Cancer: Therapeutic Implications," Mol. Cancer Ther., Aug. 2016, 15(8):1781-1791.

Fisher et al., "A Novel Adenovirus—Adeno-Associated Virus Hybrid Vector That Displays Efficient Rescue and Delivery of the AAV Genome," Hum. Gene Ther., Nov. 1996, 7(17):2079-2087.

Gervasi et al., "Parenteral protein formulations: An overview of approved products within the European Union," Eur. J Pharm. Biopharmaceutics, Oct. 2018, 131:8-24.

International Preliminary Report on Patentability in International Appln. No. PCT/US2020/062164, mailed on Jun. 9, 2022, 9 pages.

International Preliminary Report on Patentability in International Appln. No. PCT/US2021/016883, mailed on Aug. 18, 2022, 5 pages.

International Search Report and Written Opinion in International Appln. No. PCT/US2020/062164, mailed on Apr. 30, 2021, 12 pages.

(Continued)

*Primary Examiner* — Kimberly Ballard

(74) *Attorney, Agent, or Firm* — Fish & Richardson P.C.

(57) ABSTRACT

This document provides isolated immune cells that include an exogenous T cell receptor (TCR) having affinity for an Ataxia-Telangiesctasia Mutated (ATM) peptide, an exogenous TCR having affinity for an AT-rich interactive domain-containing protein 1A (ARID1A) peptide, or both an exogenous TCR having affinity for an ATM peptide and an exogenous TCR having affinity for an ARID1A peptide, as well as methods and materials for making such immune cells. For example, isolated immune cells that included an exogenous TCR having affinity for a mutant ATM and/or exogenous TCR having affinity for an ARID1A peptide, methods and materials for making such immune cells, and methods and materials for using such immune cells to treat mammals (e.g., a human having cancer) are provided.

16 Claims, 40 Drawing Sheets

Specification includes a Sequence Listing.

(56) References Cited

OTHER PUBLICATIONS

International Search Report and Written Opinion in International Appln. No. PCT/US2021/016883, mailed on Jun. 24, 2021, 5 pages.
Kammula, "TIL Therapy for Cholangiocarcinoma and Pancreatic Carcinoma", Presented at Proceedings of the Pancreatic Cancer Minisymposium, Hillman Cancer Center, UPMC, Pittsburgh, PA, May 7, 2019, 1 page (Minisymposium Schedule).
Kuball et al., "Facilitating matched pairing and expression of TCR chains introduced into human T cells," Blood, Mar. 15, 2007, 109(6):2331-2338.
Liberante et al., "Altered splicing and cytoplasmic levels of tRNA synthetases in SF3B1-mutant myelodysplastic syndromes as a therapeutic vulnerability," Sci. Reports, Feb. 25, 2019, 9(1):2678, 13 pages.
Neumann et al., "Gene transfer into mouse lyoma cells by electroporation in high electric fields," EMBO J, Jul. 1982, 1(7):841-845.
Partial Supplementary European Search Report in European Appln No. 21751111.2, dated Aug. 7, 2023, 15 pages.
Takahashi et al., "Adult classical glioblastoma with a BRAF V600E mutation," World J. Surg. Oncol., Mar. 2015, 13:100, 5 pages.
UniProt Accession No. O75533, "Splicing factor 3B subunit 1," Nov. 7, 2018, 15 pages.
Wang et al., "Clinical manufacturing of CAR T cells: foundation of a promising therapy," Mol. Ther. Oncolytics, Jun. 15, 2016, 3:16015, 7 pages.
Yadav et al., Abstract #: P228: "Tumor infiltrating lymphocyte recognition of shared neoantigens from mutated DNA repair/ remodeling proteins in a patient with metastatic pancreatic adenocarcinoma," Presented at the Proceedings of the 34th Annual Meeting & Pre-Conference Programs of the Society for Immunotherapy of Cancer (SITC 2019): part 1 : National Harbor, MD, USA. Nov. 6-10, 2019, J. Immunother. Cancer, Nov. 2019, 7(Suppl 1):282, p. 122.
Zhang et al., "Cancer-Linked SF3B1 Mutations Cause Faulty Splicing and SUGP1 Binding," Cancer Discovery, Oct. 1, 2019, 9(10):1336.
Zheng et al., "Genomic integration and gene expression by a modified adenoviral vector," Nat. Biotechnology, Feb. 2000, 18(2):176-180.
Zoller, "New recombinant DNA methodology for protein engineering," Curr. Opin. Biotechnol., Aug. 1992, 3(4):348-354.
U.S. Appl. No. 17/779,711, filed May 25, 2022, Udai Shankar Kammula, Published as U.S. Patent Application Publication No. 2023/0031784.
Bossi et al. (OncoImmunology, 2013, 2:11, e26840). (Year: 2013).
Extended European Search Report in European Appln. No. 20894301.9, dated Nov. 30, 2023, 7 pages.
Extended European Search Report in European Appln. No. 21751111.2, dated Nov. 8, 2023, 11 pages.
Garcia et al., Cell, vol. 122, 333-336, Aug. 12, 2005. (Year: 2005).
Goyarts et al., Mol Immunol. Jul. 1998; 35(10):593-607. (Year: 1998).
Janeway et al., Immunobiology, 5th Ed., Garland Science, pp. 106-108, 117-118 and 260-263, (2001). (Year: 2001).
Nakatsugawa et al., International Journal of Oncology 39: 1041-1049, 2011. (Year: 2011).
Popovic et al. (Blood. 2011; 118(4):946-954). (Year: 2011).
Hintzsche et al., "Whole-exome sequencing identifies recurrent SF3B1 R625 mutation and comutation of NF1 and KIT in mucosal melanoma," Melanoma Research, Jun. 1, 2017, 27(3):189-199.
Maguire et al., "SF3B1 mutations constitute a novel therapeutic target in breast cancer," The Journal of Pathology, Mar. 2015, 235(4):571-580.
Pereira et al., "The somatic mutation profiles of 2,433 breast cancers refine their genomic and transcriptomic landscapes," Nature Communications, May 10, 2016, 7(1):11479, 16 pages.
Rose et al., "Detection of mutations in SF3B1, EIF1AX and GNAQ in primary orbital melanoma by candidate gene analysis," BMC Cancer, Dec. 17, 2018, 18(1):1262, 9 pages.

* cited by examiner

FIGURE 1A

Gene- ATM (Protein: NCBI Reference Sequence: NP_000042.3)
Mutation- p.G2695V

Alignment of Peptide

```
ATM_WT          LAGGVNLPK    9
ATM_G2695V      LAGVVNLPK    9
ATM_G2695A      LAGAVNLPK    9
ATM_G2695C      LAGCVNLPK    9
ATM_G2695S      LAGSVNLPK    9
                *** *****
```

FIGURE 1B

```
ARID1A_WT        KESSKFPFGISPAQSHRNIKILEDEPHSKDETPLCTLLDWQDSLAKR-----C------- 48
ARID1A_H1960fs   KESSKFPFGISPAQSHRNIKILEDEPPTVKMRPHCVPF~WTGRILLPSAASVCPIPFEAC 59
                 *************************** :     * *. : *  . :        *

ARID1A_WT        ~VCVSNTIRSLSFVPGNDFEMSKHPGLLLILGKL 81
ARID1A_H1960fs   HLCQAMTLRCPN-----------TQGCCSSWAS- 81
                  :* : *:*. .             *      ..
```

FIGURE 1C

ATM Specific Chimeric TCR

**TRBV9*01 + TRAV14/DV4**

Variable: Native Human

Constant: Mouse Codon Optimized

Order of sequence

Human Beta Variable (with CDR1b, CDR2b, CDR3b underlined)-Mouse Beta Constant (in italics)-P2A cleavage site (in bold)-Human Alpha Variable (with CDR1a, CDR2a, CDR3a underlined)- Mouse Alpha Constant (in italics)

Nucleotide sequence

ATGGGCTTCAGGCTCCTCTGCTGTGTGGCCTTTTGTCTCCTGGGAGCAGGC
CCAGTGGATTCTGGAGTCACACAAACCCCAAAGCACCTGATCACAGCAACT
GGACAGCAAGTGACGCTGAGATGCTCCCCTAGGTCTGGAGACCTCTCTGTG
TACTGGTACCAACAGAGCCTGGACCAGGGCCTCCAGTTCCTCATTCAGTAT
TATAATGGAGAAGAGAGAGCAAAAGGAAACATTCTTGAACGATTCTCCGCA
CAACAGTTCCCTGACTTGCACTCTGAACTAAACCTGAGCTCTCTGGAGCTG
GGGGACTCAGCTTTGTATTTCTGTGCCAGCAGCGCGGCAGTTCACTATGGC
TACACCTTCGGTTCGGGGACCAGGTTAACCGTTGTA*GAGGACCTGAGAAACGT*
*GACACCCCCTAAGGTGAGCCTGTTCGAGCCCTCCAAGGCCGAGATCGCCAATAAGCAGA*
*AGGCCACCCTGGTGTGCCTGGCAAGGGGCTTCTTTCCTGATCACGTGGAGCTGTCTTGG*
*TGGGTGAACGGCAAGGAGGTGCACAGCGGCGTGTGCACCGACCCACAGGCCTATAAGGA*
*GAGCAATTATTCCTACTGTCTGTCTAGCCGGCTGAGAGTGAGCGCCACATTTTGGCACA*
*ACCCTCGGAATCACTTCAGATGCCAGGTGCAGTTTCACGGCCTGTCTGAGGAGGATAAG*
*TGGCCAGAGGGCAGCCCAAAGCCAGTGACCCAGAACATCTCCGCCGAGGCATGGGGAAG*
*AGCAGACTGTGGCATCACCAGCGCCTCCTACCAGCAGGGCGTGCTGTCCGCCACAATCC*
*TGTATGAGATCCTGCTGGGCAAGGCCACCCTGTACGCCGTGCTGGTGAGCACACTGGTG*
*GTCATGGCTATGGTGAAGAGGAAGAACTCC*AGGGCAAAGCGGAGCGGAAGCGGAGCCAC
AAATTTCTCTCTGCTGAAGCAGGCAGGCGATGTGGAGGAGAACCCTGGACCAATGTCA
CTTTCTAGCCTGCTGAAGGTGGTCACAGCTTCACTGTGGCTAGGACCTGGC
ATTGCCCAGAAGATAACTCAAACCCAACCAGGAATGTTCGTGCAGGAAAAG
GAGGCTGTGACTCTGGACTGCACATATGACACCAGTGATCAAAGTTATGGT
CTCTTCTGGTACAAGCAGCCCAGCAGTGGGGAAATGATTTTTCTTATTTAT
CAGGGGTCTTATGACGAGCAAAATGCAACAGAAGGTCGCTACTCATTGAAT
TTCCAGAAGGCAAGAAAATCCGCCAACCTTGTCATCTCCGCTTCACAACTG
GGGGACTCAGCAATGTATTTCTGTGCAATGAGAGAGCAGGGAGCCCAGAAG

FIGURE 1C (Cont.)

CTGGTATTTGGCCAAGGAACCAGGCTGACTATCAACCCA*AACATCCAGAATCC*
*AGAGCCCGCCGTGTATCAGCTGAAGGACCCAAGATCCCAGGATTCTACCCTGTGCCTGT*
*TCACAGACTTTGATTCTCAGATCAATGTGCCCAAGACAATGGAGAGCGGCACCTTCATC*
*ACAGACAAGTGCGTGCTGGATATGAAGGCTATGGACTCCAAGTCTAACGGCGCCATCGC*
*CTGGAGCAATCAGACCTCCTTCACATGCCAGGATATCTTTAAGGAGACAAACGCCACAT*
*ACCCTTCTAGCGACGTGCCATGTGATGCCACCCTGACAGAGAAGAGCTTCGAGACAGAC*
*ATGAACCTGAATTTTCAGAATCTGCTGGTCATCGTGCTGCGGATCCTGCTGCTGAAGGT*
*GGCTGGGTTTAATCTGCTGATGACACTGCGACTGTGGAGTAGCTGATGA*

Amino Acid sequence

MGFRLLCCVAFCLLGAGPVDSGVTQTPKHLITATGQQVTLRCSPRSGDLSV
YWYQQSLDQGLQFLIQYYNGEERAKGNILERFSAQQFPDLHSELNLSSLEL
GDSALYFCASSAAVHYGYTFGSGTRLTVV*EDLRNVTPPKVSLFEPSKAEIANKQKATLVC*
*LARGFFPDHVELSWWVNGKEVHSGVCTDPQAYKESNYSYCLSSRLRVSATFWHNPRNHFRCQVQFHGLSEE*
*DKWPEGSPKPVTQNISAEAWGRADCGITSASYQQGVLSATILYEILLGKATLYAVLVSTLVVMAMVKRKNS*
RAKRSGSGATNFSLLKQAGDVEENPGPMSLSSLLKVVTASLWLGPGIAQKITQTQ
PGMFVQEKEAVTLDCTYDTSDQSYGLFWYKQPSSGEMIFLIYQGSYDEQNA
TEGRYSLNFQKARKSANLVISASQLGDSAMYFCAMREQGAQKLVFGQGTRL
TINP*NIQNPEPAVYQLKDPRSQDSTLCLFTDFDSQINVPKTMESGTFITDKCVLDMKAMDSKSNGAIAWS*
*NQTSFTCQDIFKETNATYPSSDVPCDATLTEKSFETDMNLNFQNLLVIVLRILLLKVAGFNLLMTLRLWSS*

FIGURE 2

ATM Specific Chimeric TCR (Codon Optimized)

**TRBV9*01 + TRAV14/DV4**

Variable: Human Codon Optimized

Constant: Mouse Codon Optimized

Order of sequence

Human Beta Variable (with CDR1b, CDR2b, CDR3b underlined)-Mouse Beta Constant (in italics) - P2A cleavage site (in bold)-Human Alpha Variable (with CDR1a, CDR2a, CDR3a underlined)- Mouse Alpha Constant (in italics)

Nucleotide sequence

ATGGGCTTCCGGCTGCTGTGCTGCGTGGCATTTTGCCTGCTGGGAGCAGGA
CCTGTGGATAGCGGCGTGACCCAGACACCAAAGCACCTGATCACCGCAACA
GGACAGCAGGTGACCCTGAGGTGTTCCCCAAGATCTGGCGATCTGTCCGTG
TACTGGTATCAGCAGTCTCTGGACCAGGGCCTGCAGTTCCTGATCCAGTAC
TATAACGGCGAGGAGCGGGCCAAGGGCAATATCCTGGAGAGATTCAGCGCC
CAGCAGTTTCCTGATCTGCACTCCGAGCTGAATCTGAGCTCCCTGGAGCTG
GGCGACTCCGCCCTGTACTTCTGCGCCTCTAGCGCCGCAGTGCACTACGGC
TATACCTTTGGCTCTGGCACCAGGCTGACAGTGGTG*GAGGACCTGCGCAATGT*
*GACACCCCCTAAGGTGTCTCTGTTCGAGCCCAGCAAGGCCGAGATCGCCAACAAGCAGA*
*AGGCCACCCTGGTGTGCCTGGCCCGGGGCTTCTTTCCTGATCACGTGGAGCTGTCCTGG*
*TGGGTGAATGGCAAGGAGGTGCACTCTGGCGTGTGCACCGACCCACAGGCCTACAAGGA*
*GAGCAACTACTCCTATTGTCTGTCCTCTCGGCTGAGAGTGAGCGCCACATTTTGGCACA*
*ACCCTAGGAATCACTTCCGCTGCCAGGTGCAGTTTCACGGCCTGTCTGAGGAGGATAAG*
*TGGCCAGAGGGAAGCCCAAAGCCAGTGACCCAGAATATCTCCGCCGAGGCATGGGGAAG*
*GGCAGACTGTGGAATCACCTCTGCCAGCTATCAGCAGGGCGTGCTGTCCGCCACAATCC*
*TGTACGAGATCCTGCTGGGCAAGGCCACCCTGTATGCCGTGCTGGTGTCCACACTGGTG*
*GTCATGGCTATGGTGAAGAGGAAGAACAGC*CGGGCCAAGCGGAGCGGATCTGGAGCCAC
CAACTTCAGCCTGCTGAAGCAGGCAGGCGATGTGGAGGAGAACCCTGGACCAATGTCT
CTGAGCTCCCTGCTGAAGGTCGTGACAGCAAGCCTGTGGCTGGGACCAGGA
ATCGCACAGAAGATCACCCAGACACAGCCTGGCATGTTTGTGCAGGAGAAG
GAGGCCGTGACCCTGGACTGCACCTACGACACATCTGATCAGAGCTACGGC
CTGTTCTGGTATAAGCAGCCATCTAGCGGCGAGATGATCTTTCTGATCTAC
CAGGGCAGCTATGATGAGCAGAACGCCACAGAGGGCCGGTACTCTCTGAAT
TTCCAGAAGGCCAGAAAGAGCGCCAACCTGGTCATCAGCGCCTCCCAGCTG
GGCGACTCCGCCATGTATTTCTGTGCCATGAGGGAGCAGGGCGCCCAGAAG

FIGURE 2 (Cont.)

CTGGTGTTTGGCCAGGGCACCCGCCTGACAATCAACCCA*AATATCCAGAATCC*
*CGAGCCTGCCGTGTACCAGCTGAAGGACCCCAGATCCCAGGATTCTACCCTGTGCCTGT*
*TCACAGACTTTGATAGCCAGATCAACGTGCCCAAGACAATGGAGTCCGGCACCTTCATC*
*ACAGACAAGTGCGTGCTGGACATGAAGGCTATGGACTCTAAGAGCAACGGCGCCATCGC*
*CTGGAGCAATCAGACCTCCTTCACATGCCAGGATATCTTTAAGGAGACCAACGCCACAT*
*ATCCATCCTCTGACGTGCCCTGTGATGCCACCCTGACAGAGAAGTCCTTCGAGACCGAC*
*ATGAACCTGAATTTTCAGAATCTGCTGGTCATCGTGCTGCGGATCCTGCTGCTGAAGGT*
*GGCCGGCTTTAACCTGCTGATGACACTGAGACTGTGGAGCTCCTGATGA*

Amino Acid sequence

MGFRLLCCVAFCLLGAGPVDSGVTQTPKHLITATGQQVTLRCSPRSGDLSV
YWYQQSLDQGLQFLIQYYNGEERAKGNILERFSAQQFPDLHSELNLSSLEL
GDSALYFCASSAAVHYGYTFGSGTRLTVV*EDLRNVTPPKVSLFEPSKAEIANKQK*
*ATLVCLARGFFPDHVELSWWVNGKEVHSGVCTDPQAYKESNYSYCLSSRLRVSATFWHN*
*PRNHFRCQVQFHGLSEEDKWPEGSPKPVTQNISAEAWGRADCGITSASYQQGVLSATIL*
*YEILLGKATLYAVLVSTLVVMAMVKRKNS*RAKRSGSGATNFSLLKQAGDVEENPGPMSL
SSLLKVVTASLWLGPGIAQKITQTQPGMFVQEKEAVTLDCTYDTSDQSYGL
FWYKQPSSGEMIFLIYQGSYDEQNATEGRYSLNFQKARKSANLVISASQLG
DSAMYFCAMREQGAQKLVFGQGTRLTINP*NIQNPEPAVYQLKDPRSQDSTLCLFT*
*DFDSQINVPKTMESGTFITDKCVLDMKAMDSKSNGAIAWSNQTSFTCQDIFKETNATYP*
*SSDVFCDATLTEKSFETDMNLNFQNLLVIVLRILLLKVAGFNLLMTLRLWSS*

FIGURE 3

ATM Specific Human TCR (Native Sequence)

**TRBV9*01 + TRAV14/DV4**

Variable: Native Human

Constant: Native Human

Order of sequence

Human Beta Variable (with CDR1b, CDR2b, CDR3b underlined)-Human Beta Constant (in italics)- P2A cleavage site (in bold)-Human Alpha Variable (with CDR1a, CDR2a, CDR3a underlined)- Human Alpha Constant (in italics)

Nucleotide sequence

ATGGGCTTCAGGCTCCTCTGCTGTGTGGCCTTTTGTCTCCTGGGAGCAGGC
CCAGTGGATTCTGGAGTCACACAAACCCCAAAGCACCTGATCACAGCAACT
GGACAGCAAGTGACGCTGAGATGCTCCCCTAGGTCTGGAGACCTCTCTGTG
TACTGGTACCAACAGAGCCTGGACCAGGGCCTCCAGTTCCTCATTCAGTAT
TATAATGGAGAAGAGAGAGCAAAAGGAAACATTCTTGAACGATTCTCCGCA
CAACAGTTCCCTGACTTGCACTCTGAACTAAACCTGAGCTCTCTGGAGCTG
GGGGACTCAGCTTTGTATTTCTGTGCCAGCAGCGCGGCAGTTCACTATGGC
TACACCTTCGGTTCGGGGACCAGGTTAACCGTTGTA*GAGGACCTGAACAAGGT*
*GTTCCCACCCGAGGTCGCTGTGTTTGAGCCATCAGAAGCAGAGATCTCCCACACCCAAA*
*AGGCCACACTGGTGTGCCTGGCCACAGGCTTCTTCCCCGACCACGTGGAGCTGAGCTGG*
*TGGGTGAATGGGAAGGAGGTGCACAGTGGGGTCAGCACGGACCCGCAGCCCCTCAAGGA*
*GCAGCCCGCCCTCAATGACTCCAGATACTGCCTGAGCAGCCGCCTGAGGGTCTCGGCCA*
*CCTTCTGGCAGAACCCCCGCAACCACTTCCGCTGTCAAGTCCAGTTCTACGGGCTCTCG*
*GAGAATGACGAGTGGACCCAGGATAGGGCCAAACCCGTCACCCAGATCGTCAGCGCCGA*
*GGCCTGGGGTAGAGCAGACTGTGGCTTTACCTCGGTGTCCTACCAGCAAGGGGTCCTGT*
*CTGCCACCATCCTCTATGAGATCCTGCTAGGGAAGGCCACCCTGTATGCTGTGCTGGTC*
*AGCGCCCTTGTGTTGATGGCCATGGTCAAGAGAAAGGATTTC*AGGGCAAAGCGGAGCGG
AAGCGGAGCCACAAATTTCTCTCTGCTGAAGCAGGCAGGCGATGTGGAGGAGAACCCTG
GACCAATGTCACTTTCTAGCCTGCTGAAGGTGGTCACAGCTTCACTGTGGCT
AGGACCTGGCATTGCCCAGAAGATAACTCAAACCCAACCAGGAATGTTCGT
GCAGGAAAAGGAGGCTGTGACTCTGGACTGCACATATGACACCAGTGATCA
AAGTTATGGTCTCTTCTGGTACAAGCAGCCCAGCAGTGGGGAAATGATTTT
TCTTATTTATCAGGGGTCTTATGACGAGCAAAATGCAACAGAAGGTCGCTA
CTCATTGAATTTCCAGAAGGCAAGAAAATCCGCCAACCTTGTCATCTCCGC
TTCACAACTGGGGGACTCAGCAATGTATTTCTGTGCAATGAGAGAGCAGGG
AGCCCAGAAGCTGGTATTTGGCCAAGGAACCAGGCTGACTATCAACCCAAA
*TATCCAGAACCCTGACCCTGCCGTGTACCAGCTGAGAGACTCTAAATCCAGTGACAAGT*

FIGURE 3 (Cont.)

*CTGTCTGCCTATTCACCGATTTTGATTCTCAAACAAATGTGTCACAAAGTAAGGATTCT*
*GATGTGTATATCACAGACAAAACTGTGCTAGACATGAGGTCTATGGACTTCAAGAGCAA*
*CAGTGCTGTGGCCTGGAGCAACAAATCTGACTTTGCATGTGCAAACGCCTTCAACAACA*
*GCATTATTCCAGAAGACACCTTCTTCCCCAGCCCAGAAAGTTCCTGTGATGTCAAGCTG*
*GTCGAGAAAAGCTTTGAAACAGATACGAACCTAAACTTTCAAAACCTGTCAGTGATTGG*
*GTTCCGAATCCTCCTCCTGAAAGTGGCCGGGTTTAATCTGCTCATGACGCTGCGGCTGT*
*GGTCCAGCTGATGA*

Amino acid Sequence

MGFRLLCCVAFCLLGAGPVDSGVTQTPKHLITATGQQVTLRCSPRSGDLSV
YWYQQSLDQGLQFLIQYYNGEERAKGNILERFSAQQFPDLHSELNLSSLEL
GDSALYFCASSAAVHYGYTFGSGTRLTVV*EDLNKVFPPEVAVFEPSEAEISHTQK*
*ATLVCLATGFFPDHVELSWWVNGKEVHSGVSTDPQPLKEQPALNDSRYCLSSRLRVSAT*
*FWQNPRNHFRCQVQFYGLSENDEWTQDRAKPVTQIVSAEAWGRADCGFTSVSYQQGVLS*
*ATILYEILLGKATLYAVLVSALVLMAMVKRKDF*RAKRSGSGATNFSLLKQAGDVEENPG
PMSLSSLLKVVTASLWLGPGIAQKITQTQPGMFVQEKEAVTLDCTYDTSDQ
SYGLFWYKQPSSGEMIFLIYQGSYDEQNATEGRYSLNFQKARKSANLVISA
SQLGDSAMYFCAMREQGAQKLVFGQGTRLTINP*NIQNPDPAVYQLRDSKSSDKS*
*VCLFTDFDSQTNVSQSKDSDVYITDKTVLDMRSMDFKSNSAVAWSNKSDFACANAFNNS*
*IIPEDTFFPSPESSCDVKLVEKSFETDTNLNFQNLSVIGFRILLLKVAGFNLLMTLRLW*
*SS*

FIGURE 4

ATM Specific Human TCR (Codon Optimized)

**TRBV9*01 + TRAV14/DV4**

Variable: Native Human (Codon Optimized)

Constant: Native Human (Codon Optimized)

Order of sequence

Human Beta Variable (with CDR1b, CDR2b, CDR3b underlined)-Human Beta Constant (italics)- P2A cleavage site (in bold)- Human Alpha Variable (with CDR1a, CDR2a, CDR3a underlined)- Human Alpha Constant (italics)

Nucleotide sequence

ATGGGCTTCCGGCTGCTGTGCTGCGTGGCATTTTGCCTGCTGGGAGCAGGA
CCTGTGGATAGCGGCGTGACCCAGACACCAAAGCACCTGATCACCGCAACA
GGACAGCAGGTGACCCTGAGGTGTTCCCCAAGATCTGGCGATCTGTCCGTG
TACTGGTATCAGCAGTCTCTGGACCAGGGCCTGCAGTTCCTGATCCAGTAC
TATAACGGCGAGGAGCGGGCCAAGGGCAATATCCTGGAGAGATTCAGCGCC
CAGCAGTTTCCTGATCTGCACTCCGAGCTGAATCTGAGCTCCCTGGAGCTG
GGCGACTCCGCCCTGTACTTCTGCGCCTCTAGCGCCGCAGTGCACTACGGC
TATACCTTTGGCTCTGGCACCAGGCTGACAGTGGTGGAGGACCTGAATAAGGT
GTTCCCCCCTGAGGTGGCCGTGTTTGAGCCTTCCGAGGCCGAGATCTCTCACACCCAGA
AGGCCACCCTGGTGTGCCTGGCAACCGGCTTCTTTCCAGATCACGTGGAGCTGAGCTGG
TGGGTGAACGGCAAGGAGGTGCACAGCGGCGTGTCCACCGACCCACAGCCCCTGAAGGA
GCAGCCCGCCCTGAATGATAGCAGATATTGCCTGTCTAGCCGGCTGAGAGTGTCCGCCA
CCTTTTGGCAGAACCCTCGGAATCACTTCAGATGTCAGGTGCAGTTTTACGGCCTGAGC
GAGAATGACGAGTGGACCCAGGATAGGGCCAAGCCCGTGACACAGATCGTGTCCGCCGA
GGCATGGGGAAGGGCAGACTGCGGCTTCACATCCGTGTCTTATCAGCAGGGCGTGCTGA
GCGCCACCATCCTGTATGAGATCCTGCTGGGCAAGGCCACACTGTACGCCGTGCTGGTG
TCCGCCCTGGTGCTGATGGCTATGGTGAAGCGGAAGGACTTTCGGGCCAAGCGGAGCGG
ATCTGGAGCCACCAACTTCAGCCTGCTGAAGCAGGCAGGCGATGTGGAGGAGAACCCTG
GACCAATGTCTCTGAGCTCCCTGCTGAAGGTCGTGACAGCAAGCCTGTGGCT
GGGACCAGGAATCGCACAGAAGATCACCCAGACACAGCCTGGCATGTTTGT
GCAGGAGAAGGAGGCCGTGACCCTGGACTGCACCTACGACACATCTGATCA
GAGCTACGGCCTGTTCTGGTATAAGCAGCCATCTAGCGGCGAGATGATCTT
TCTGATCTACCAGGGCAGCTATGATGAGCAGAACGCCACAGAGGGCCGGTA
CTCTCTGAATTTCCAGAAGGCCAGAAAGAGCGCCAACCTGGTCATCAGCGC
CTCCCAGCTGGGCGACTCCGCCATGTATTTCTGTGCCATGAGGGAGCAGGG

FIGURE 4 (Cont.)

*CGCCCAGAAGCTGGTGTTTGGCCAGGGCACCCGCCTGACAATCAACCCAAA*
*CATCCAGAATCCCGACCCTGCCGTGTATCAGCTGAGGGACTCCAAGTCCTCTGATAAGA*
*GCGTGTGCCTGTTCACCGACTTTGATTCTCAGACAAACGTGAGCCAGTCCAAGGACAGC*
*GACGTGTACATCACCGACAAGACAGTGCTGGATATGCGGAGCATGGACTTCAAGTCTAA*
*CAGCGCCGTGGCCTGGAGCAATAAGTCCGATTTCGCCTGCGCCAATGCCTTTAACAATT*
*CCATCATCCCTGAGGATACCTTCTTTCCATCTCCCGAGAGCTCCTGTGACGTGAAGCTG*
*GTGGAGAAGTCTTTCGAGACCGATACAAACCTGAATTTTCAGAACCTGAGCGTGATCGG*
*CTTCCGGATCCTGCTGCTGAAGGTGGCCGGCTTCAATCTGCTGATGACACTGAGACTGT*
*GGTCTAGCTGATGA*

Amino Acid sequence

MGFRLLCCVAFCLLGAGPVDSGVTQTPKHLITATGQQVTLRCSPRSGDLSV
YWYQQSLDQGLQFLIQYYNGEERAKGNILERFSAQQFPDLHSELNLSSLEL
GDSALYFCASSAAVHYGYTFGSGTRLTVV*EDLNKVFPPEVAVFEPSEAEISHTQK*
*ATLVCLATGFFPDHVELSWWVNGKEVHSGVSTDPQPLKEQPALNDSRYCLSSRLRVSAT*
*FWQNPRNHFRCQVQFYGLSENDEWTQDRAKPVTQIVSAEAWGRADCGFTSVSYQQGVLS*
*ATILYEILLGKATLYAVLVSALVLMAMVKRKDF*RAKRSGSGATNFSLLKQAGDVEENPG
PMSLSSLLKVVTASLWLGPGIAQKITQTQPGMFVQEKEAVTLDCTYDTSDQ
SYGLFWYKQPSSGEMIFLIYQGSYDEQNATEGRYSLNFQKARKSANLVISA
SQLGDSAMYFCAMREQGAQKLVFGQGTRLTINP*NIQNPDPAVYQLRDSKSSDKS*
*VCLFTDFDSQTNVSQSKDSDVYITDKTVLDMRSMDFKSNSAVAWSNKSDFACANAFNNS*
*IIPEDTFFPSPESSCDVKLVEKSFETDTNLNFQNLSVIGFRILLLKVAGFNLLMTLRLW*
*SS*

FIGURE 5

ARID1A Specific Chimeric TCR

TRBV25-1+ TRAV20

Variable: Native Human

Constant: Mouse (Codon Optimized)

Order of sequence

Human Beta Variable (with CDR1b, CDR2b, CDR3b underlined)-Mouse Beta Constant (in italics) – P2A cleavage site (in bold) –Human Alpha Variable (with CDR1a, CDR2a, CDR3a underlined)- Mouse Alpha Constant (in italics)

Nucleotide sequence

ATGACTATCAGGCTCCTCTGCTACATGGGCTTTTATTTTCTGGGGGCAGGC
CTCATGGAAGCTGACATCTACCAGACCCCAAGATACCTTGTTATAGGGACA
GGAAAGAAGATCACTCTGGAATGTTCTCAAACCATGGCCATGACAAAATG
TACTGGTATCAACAAGATCCAGGAATGGAACTACACCTCATCCACTATTCC
TATGGAGTTAATTCCACAGAGAAGGGAGATCTTTCCTCTGAGTCAACAGTC
TCCAGAATAAGGACGGAGCATTTTCCCCTGACCCTGGAGTCTGCCAGGCCC
TCACATACCTCTCAGTACCTCTGTGCCAGCAGTCCGCCGGGACAGCCTTAC
GAGCAGTACTTCGGGCCGGGCACCAGGCTCACGGTCACA*GAGGACCTGAGAAA*
*CGTGACACCCCCTAAGGTGAGCCTGTTCGAGCCCTCCAAGGCCGAGATCGCCAATAAGC*
*AGAAGGCCACCCTGGTGTGCCTGGCAAGGGGCTTCTTTCCTGATCACGTGGAGCTGTCT*
*TGGTGGGTGAACGGCAAGGAGGTGCACAGCGGCGTGTGCACCGACCCACAGGCCTATAA*
*GGAGAGCAATTATTCCTACTGTCTGTCTAGCCGGCTGAGAGTGAGCGCCACATTTGGC*
*ACAACCCTCGGAATCACTTCAGATGCCAGGTGCAGTTTCACGGCCTGTCTGAGGAGGAT*
*AAGTGGCCAGAGGGCAGCCCAAAGCCAGTGACCCAGAACATCTCCGCCGAGGCATGGGG*
*AAGAGCAGACTGTGGCATCACCAGCGCCTCCTACCAGCAGGGCGTGCTGTCCGCCACAA*
*TCCTGTATGAGATCCTGCTGGGCAAGGCCACCCTGTACGCCGTGCTGGTGAGCACACTG*
*GTGGTCATGGCTATGGTGAAGAGGAAGAACTCC*AGGGCAAAGCGGAGCGGAAGCGGAGC
CACAAATTTCTCTCTGCTGAAGCAGGCAGGCGATGTGGAGGAGAACCCTGGACCAATGG
AGAAAATGTTGGAGTGTGCATTCATAGTCTTGTGGCTTCAGCTTGGCTGGT
TGAGTGGAGAAGACCAGGTGACGCAGAGTCCCGAGGCCCTGAGACTCCAGG
AGGGAGAGAGTAGCAGTCTCAACTGCAGTTACACAGTCAGCGGTTTAAGAG
GGCTGTTCTGGTATAGGCAAGATCCTGGGAAAGGCCCTGAATTCCTCTTCA
CCCTGTATTCAGCTGGGGAAGAAAAGGAGAAAGAAAGGCTAAAAGCCACAT
TAACAAAGAAGGAAAGCTTTCTGCACATCACAGCCCCTAAACCTGAAGACT
CAGCCACTTATCTCTGTGCTGTGCGGATGAACACAGGCTTTCAGAAACTTG
TATTTGGAACTGGCACCCGACTTCTGGTCAGTCCA*AACATCCAGAATCCAGAGC*
*CCGCCGTGTATCAGCTGAAGGACCCAAGATCCCAGGATTCTACCCTGTGCCTGTTCACA*

FIGURE 5(Cont.)

*GACTTTGATTCTCAGATCAATGTGCCCAAGACAATGGAGAGCGGCACCTTCATCACAGA*
*CAAGTGCGTGCTGGATATGAAGGCTATGGACTCCAAGTCTAACGGCGCCATCGCCTGGA*
*GCAATCAGACCTCCTTCACATGCCAGGATATCTTTAAGGAGACAAACGCCACATACCCT*
*TCTAGCGACGTGCCATGTGATGCCACCCTGACAGAGAAGAGCTTCGAGACAGACATGAA*
*CCTGAATTTTCAGAATCTGCTGGTCATCGTGCTGCGGATCCTGCTGCTGAAGGTGGCTG*
*GGTTTAATCTGCTGATGACACTGCGACTGTGGAGTAGCTGATGA*

Amino Acid sequence

MTIRLLCYMGFYFLGAGLMEADIYQTPRYLVIGTGKKITLECSQTMGHDKM
YWYQQDPGMELHLIHYSYGVNSTEKGDLSSESTVSRIRTEHFPLTLESARP
SHTSQYLCASSPPGQPYEQYFGPGTRLTVT*EDLRNVTPPKVSLFEPSKAEIANK*
*QKATLVCLARGFFPDHVELSWWVNGKEVHSGVCTDPQAYKESNYSYCLSSRLRVSATFW*
*HNPRNHFRCQVQFHGLSEEDKWPEGSPKPVTQNISAEAWGRADCGITSASYQQGVLSAT*
*ILYEILLGKATLYAVLVSTLVVMAMVKRKNS*RAKRSGSGATNFSLLKQAGDVEENPGPM
EKMLECAFIVLWLQLGWLSGEDQVTQSPEALRLQEGESSSLNCSYTVSGLR
GLFWYRQDPGKGPEFLFTLYSAGEEKEKERLKATLTKKESFLHITAPKPED
SATYLCAVRMNTGFQKLVFGTGTRLLVSP*NIQNPEPAVYQLKDPRSQDSTLCLFT*
*DFDSQINVPKTMESGTFITDKCVLDMKAMDSKSNGAIAWSNQTSFTCQDIFKETNATYP*
*SSDVPCDATLTEKSFETDMNLNFQNLLVIVLRILLLKVAGFNLLMTLRLWSS*

FIGURE 6

ARID1A Specific Chimeric TCR (Codon Optimized)

TRBV25-1+ TRAV20

Variable: Native Human (Codon Optimized)

Constant: Mouse (Codon Optimized)

Order of sequence

Human Beta Variable (with CDR1b, CDR2b, CDR3b underlined)-Mouse Beta Constant (italics)-P2A cleavage site (in bold)-Human Alpha Variable (with CDR1a, CDR2a, CDR3a underlined)- Mouse Alpha Constant (italics)

Nucleotide sequence

ATGACCATCCGGCTGCTGTGCTACATGGGCTTCTATTTTCTGGGCGCCGGC
CTGATGGAGGCCGATATCTACCAGACCCCCAGATACCTGGTCATCGGCACC
GGCAAGAAGATCACACTGGAGTGTTCCCAGACAATGGGCCACGATAAGATG
TACTGGTATCAGCAGGACCCTGGCATGGAGCTGCACCTGATCCACTACTCC
TATGGCGTGAACTCTACCGAGAAGGGCGACCTGAGCTCCGAGTCCACCGTG
TCTCGGATCAGAACAGAGCACTTCCCACTGACCCTGGAGAGCGCCAGGCCT
AGCCACACATCCCAGTACCTGTGCGCCTCTAGCCCACCTGGACAGCCTTAC
GAGCAGTATTTCGGCCCAGGCACCAGGCTGACCGTGACA*GAGGATCTGCGCAA*
*CGTGACACCACCCAAGGTGAGCCTGTTTGAGCCCTCCAAGGCCGAGATCGCCAATAAGC*
*AGAAGGCCACCCTGGTGTGCCTGGCCCGCGGCTTCTTTCCTGATCACGTGGAGCTGTCC*
*TGGTGGGTGAACGGCAAGGAGGTGCACTCTGGCGTGTGCACCGACCCACAGGCCTATAA*
*GGAGTCTAATTACAGCTATTGTCTGTCCTCTAGGCTGCGCGTGTCCGCCACATTCTGGC*
*ACAACCCTAGGAATCACTTCCGCTGCCAGGTGCAGTTTCACGGCCTGTCCGAGGAGGAT*
*AAGTGGCCAGAGGGCTCTCCTAAGCCAGTGACCCAGAATATCAGCGCCGAGGCATGGGG*
*AAGGGCAGACTGTGGAATCACCTCCGCCTCTTACCAGCAGGGCGTGCTGAGCGCCACAA*
*TCCTGTACGAGATCCTGCTGGGCAAGGCCACACTGTATGCCGTGCTGGTGTCCACCCTG*
*GTGGTCATGGCTATGGTGAAGCGCAAGAACTCT*CGGGCCAAGAGAAGCGGATCCGGAGC
CACAAATTTCAGCCTGCTGAAGCAGGCAGGCGATGTGGAGGAGAACCCAGGACCTATGG
AGAAGATGCTGGAGTGCGCCTTTATCGTGCTGTGGCTGCAGCTGGGATGGC
TGTCTGGAGAGGACCAGGTGACCCAGAGCCCAGAGGCCCTGAGGCTGCAGG
AGGGAGAGAGCTCCTCTCTGAATTGTAGCTACACAGTGTCCGGCCTGCGGG
GCCTGTTCTGGTATAGACAGGATCCCGGCAAGGGCCCTGAGTTCCTGTTTA
CCCTGTACTCCGCCGGCGAGGAGAAGGAGAAGGAGAGACTGAAGGCCACCC
TGACAAAGAAGGAGTCTTTTCTGCACATCACAGCCCCAAAGCCCGAGGACA
GCGCCACCTATCTGTGCGCCGTGCGGATGAACACAGGCTTCCAGAAGCTGG
TGTTTGGCACCGGCACAAGACTGCTGGTGAGCCCA*AACATCCAGAATCCTGAGC*

FIGURE 6 (Cont.)

*CAGCCGTGTACCAGCTGAAGGACCCCCGGTCCCAGGATTCTACCCTGTGCCTGTTCACA*
*GACTTTGATAGCCAGATCAACGTGCCCAAGACAATGGAGTCCGGCACCTTCATCACAGA*
*CAAGTGCGTGCTGGACATGAAGGCTATGGACTCTAAGAGCAACGGCGCCATCGCCTGGT*
*CTAATCAGACCAGCTTCACATGCCAGGATATCTTTAAGGAGACCAATGCCACATACCCA*
*AGCTCCGACGTGCCCTGTGATGCCACCCTGACAGAGAAGAGCTTCGAGACCGACATGAA*
*CCTGAATTTTCAGAACCTGCTGGTCATCGTGCTGAGGATCCTGCTGCTGAAGGTGGCCG*
*GCTTTAATCTGCTGATGACACTGCGCCTGTGGTCTAGCTGATGA*

Amino Acid sequence

MTIRLLCYMGFYFLGAGLMEADIYQTPRYLVIGTGKKITLECSQTMGHDKM
YWYQQDPGMELHLIHYSYGVNSTEKGDLSSESTVSRIRTEHFPLTLESARP
SHTSQYLCASSPPGQPYEQYFGPGTRLTVTEDLRNVTPPKVSLFEPSKAEIANK
QKATLVCLARGFFPDHVELSWWVNGKEVHSGVCTDPQAYKESNYSYCLSSRLRVSATFW
HNPRNHFRCQVQFHGLSEEDKWPEGSPKPVTQNISAEAWGRADCGITSASYQQGVLSAT
ILYEILLGKATLYAVLVSTLVVMAMVKRKNSRAKRSGSGATNFSLLKQAGDVEENPGPM
EKMLECAFIVLWLQLGWLSGEDQVTQSPEALRLQEGESSSLNCSYTVSGLR
GLFWYRQDPGKGPEFLFTLYSAGEEKEKERLKATLTKKESFLHITAPKPED
SATYLCAVRMNTGFQKLVFGTGTRLLVSP*NIQNPEPAVYQLKDPRSQDSTLCLFT*
*DFDSQINVPKTMESGTFITDKCVLDMKAMDSKSNGAIAWSNQTSFTCQDIFKETNATYP*
*SSDVFCDATLTEKSFETDMNLNFQNLLVIVLRILLLKVAGFNLLMTLRLWSS*

FIGURE 7

ARID1A Specific Human TCR (Native)

TRBV25-1+ TRAV20

Variable: Native Human

Constant: Native Human

Order of sequence

Human Beta Variable (with CDR1b, CDR2b, CDR3b underlined)-Human Beta Constant (italics)- P2A cleavage site (in bold)-Human Alpha Variable (with CDR1a, CDR2b, CDR3a underlined)- Human Alpha Constant (italics)

Nucleotide sequence

ATGACTATCAGGCTCCTCTGCTACATGGGCTTTTATTTTCTGGGGGCAGGC
CTCATGGAAGCTGACATCTACCAGACCCCAAGATACCTTGTTATAGGGACA
GGAAAGAAGATCACTCTGGAATGTTCTCAAACCATGGGCCATGACAAAATG
TACTGGTATCAACAAGATCCAGGAATGGAACTACACCTCATCCACTATTCC
TATGGAGTTAATTCCACAGAGAAGGGAGATCTTTCCTCTGAGTCAACAGTC
TCCAGAATAAGGACGGAGCATTTTCCCCTGACCCTGGAGTCTGCCAGGCCC
TCACATACCTCTCAGTACCTCTGTGCCAGCAGTCCGCCGGGACAGCCTTAC
GAGCAGTACTTCGGGCCGGGCACCAGGCTCACGGTCACA*GAGGACCTGAACAA*
*GGTGTTCCCACCCGAGGTCGCTGTGTTTGAGCCATCAGAAGCAGAGATCTCCCACACCC*
*AAAAGGCCACACTGGTGTGCCTGGCCACAGGCTTCTTCCCCGACCACGTGGAGCTGAGC*
*TGGTGGGTGAATGGGAAGGAGGTGCACAGTGGGGTCAGCACGGACCCGCAGCCCCTCAA*
*GGAGCAGCCCGCCCTCAATGACTCCAGATACTGCCTGAGCAGCCGCCTGAGGGTCTCGG*
*CCACCTTCTGGCAGAACCCCCGCAACCACTTCCGCTGTCAAGTCCAGTTCTACGGGCTC*
*TCGGAGAATGACGAGTGGACCCAGGATAGGGCCAAACCCGTCACCCAGATCGTCAGCGC*
*CGAGGCCTGGGGTAGAGCAGACTGTGGCTTTACCTCGGTGTCCTACCAGCAAGGGGTCC*
*TGTCTGCCACCATCCTCTATGAGATCCTGCTAGGGAAGGCCACCCTGTATGCTGTGCTG*
*GTCAGCGCCCTTGTGTTGATGGCCATGGTCAAGAGAAAGGATTTC*AGGGCAAAGCGGAG
CGGAAGCGGAGCCACAAATTTCTCTCTGCTGAAGCAGGCAGGCGATGTGGAGGAGAACC
CTGGACCAATGGAGAAAATGTTGGAGTGTGCATTCATAGTCTTGTGGCTTCA
GCTTGGCTGGTTGAGTGGAGAAGACCAGGTGACGCAGAGTCCCGAGGCCCT
GAGACTCCAGGAGGGAGAGAGTAGCAGTCTCAACTGCAGTTACACAGTCAG
CGGTTTAAGAGGGCTGTTCTGGTATAGGCAAGATCCTGGGAAAGGCCCTGA
ATTCCTCTTCACCCTGTATTCAGCTGGGGAAGAAAAGGAGAAAGAAAGGCT
AAAAGCCACATTAACAAAGAAGGAAAGCTTTCTGCACATCACAGCCCCTAA
ACCTGAAGACTCAGCCACTTATCTCTGTGCTGTGCGGATGAACACAGGCTT
TCAGAAACTTGTATTTGGAACTGGCACCCGACTTCTGGTCAGTCCAA*ATATC*
*CAGAACCCTGACCCTGCCGTGTACCAGCTGAGAGACTCTAAATCCAGTGACAAGTCTGT*

FIGURE 7 (Cont.)

*CTGCCTATTCACCGATTTTGATTCTCAAACAAATGTGTCACAAAGTAAGGATTCTGATG TGTATATCACAGACAAAACTGTGCTAGACATGAGGTCTATGGACTTCAAGAGCAACAGT GCTGTGGCCTGGAGCAACAAATCTGACTTTGCATGTGCAAACGCCTTCAACAACAGCAT TATTCCAGAAGACACCTTCTTCCCCAGCCCAGAAAGTTCCTGTGATGTCAAGCTGGTCG AGAAAAGCTTTGAAACAGATACGAACCTAAACTTTCAAAACCTGTCAGTGATTGGGTTC CGAATCCTCCTCCTGAAAGTGGCCGGGTTTAATCTGCTCATGACGCTGCGGCTGTGGTC CAGCTGATGA*

Amino Acid sequence

MTIRLLCYMGFYFLGAGLMEADIYQTPRYLVIGTGKKITLECSQTMGHDKM YWYQQDPGMELHLIHYSYGVNSTEKGDLSSESTVSRIRTEHFPLTLESARP SHTSQYLCASSPPGQPYEQYFGPGTRLTVT*EDLNKVFPPEVAVFEPSEAEISHT QKATLVCLATGFFPDHVELSWWVNGKEVHSGVSTDPQPLKEQPALNDSRYCLSSRLRVS ATFWQNPRNHFRCQVQFYGLSENDEWTQDRAKPVTQIVSAEAWGRADCGFTSVSYQQGV LSATILYEILLGKATLYAVLVSALVLMAMVKRKDF*RAKRSGSGATNFSLLKQAGDVEEN PGPMEKMLECAFIVLWLQLGWLSGEDQVTQSPEALRLQEGESSSLNCSYTV SGLRGLFWYRQDPGKGPEFLFTLYSAGEEKEKERLKATLTKKESFLHITAP KPEDSATYLCAVRMNTGFQKLVFGTGTRLLVSP*NIQNPDPAVYQLRDSKSSDKS VCLFTDFDSQTNVSQSKDSDVYITDKTVLDMRSMDFKSNSAVAWSNKSDFACANAFNNS IIPEDTFFPSPESSCDVKLVEKSFETDTNLNFQNLSVIGFRILLLKVAGFNLLMTLRLW SS*

FIGURE 8

ARID1A Specific Human TCR (Codon Optimized)

TRBV25-1+ TRAV20

Variable: Native Human (codon optimized)

Constant: Native human (codon optimized)

Order of sequence

Human Beta Variable (with CDR1b, CDR2b, CDR3b underlined)-Human Beta Constant (italics)-P2A cleavage site (in bold)-Human Alpha Variable (with CDR1a, CDR2a, CDR3a underlined) - Human Alpha Constant (italics)

Nucleotide sequence

ATGACCATCCGGCTGCTGTGCTACATGGGCTTCTATTTTCTGGGCGCCGGC
CTGATGGAGGCCGATATCTACCAGACCCCCAGATACCTGGTCATCGGCACC
GGCAAGAAGATCACACTGGAGTGTTCCCAGACAATGGGCCACGATAAGATG
TACTGGTATCAGCAGGACCCTGGCATGGAGCTGCACCTGATCCACTACTCC
TATGGCGTGAACTCTACCGAGAAGGGCGACCTGAGCTCCGAGTCCACCGTG
TCTCGGATCAGAACAGAGCACTTCCCACTGACCCTGGAGAGCGCCAGGCCT
AGCCACACATCCCAGTACCTGTGCGCCTCTAGCCCACCTGGACAGCCTTAC
GAGCAGTATTTCGGCCCAGGCACCAGGCTGACCGTGACA*GAGGACCTGAATAA*
*GGTGTTCCCCCCTGAGGTGGCCGTGTTTGAGCCTTCCGAGGCCGAGATCTCTCACACCC*
*AGAAGGCCACCCTGGTGTGCCTGGCAACCGGCTTCTTTCCAGATCACGTGGAGCTGAGC*
*TGGTGGGTGAACGGCAAGGAGGTGCACAGCGGCGTGTCCACCGACCCACAGCCCCTGAA*
*GGAGCAGCCCGCCCTGAATGATAGCAGATATTGCCTGTCTAGCCGGCTGAGAGTGTCCG*
*CCACCTTTTGGCAGAACCCTCGGAATCACTTCAGATGTCAGGTGCAGTTTTACGGCCTG*
*AGCGAGAATGACGAGTGGACCCAGGATAGGGCCAAGCCCGTGACACAGATCGTGTCCGC*
*CGAGGCATGGGGAAGGGCAGACTGCGGCTTCACATCCGTGTCTTATCAGCAGGGCGTGC*
*TGAGCGCCACCATCCTGTATGAGATCCTGCTGGGCAAGGCCACACTGTACGCCGTGCTG*
*GTGTCCGCCCTGGTGCTGATGGCTATGGTGAAGCGGAAGGACTTT*CGGGCCAAGAGAAG
CGGATCCGGAGCCACAAATTTCAGCCTGCTGAAGCAGGCAGGCGATGTGGAGGAGAACC
CAGGACCTATGGAGAAGATGCTGGAGTGCGCCTTTATCGTGCTGTGGCTGCA
GCTGGGATGGCTGTCTGGAGAGGACCAGGTGACCCAGAGCCCAGAGGCCCT
GAGGCTGCAGGAGGGAGAGAGCTCCTCTCTGAATTGTAGCTACACAGTGTC
CGGCCTGCGGGGCCTGTTCTGGTATAGACAGGATCCCGGCAAGGGCCCTGA
GTTCCTGTTTACCCTGTACTCCGCCGGCGAGGAGAAGGAGAAGGAGAGACT
GAAGGCCACCCTGACAAAGAAGGAGTCTTTTCTGCACATCACAGCCCCAAA
GCCCGAGGACAGCGCCACCTATCTGTGCGCCGTGCGGATGAACACAGGCTT
CCAGAAGCTGGTGTTTGGCACCGGCACAAGACTGCTGGTGAGCCCA*ACATC*

FIGURE 8 (Cont.)

*CAGAATCCCGACCCTGCCGTGTATCAGCTGAGGGACTCCAAGTCCTCTGATAAGAGCGT*
*GTGCCTGTTCACCGACTTTGATTCTCAGACAAACGTGAGCCAGTCCAAGGACAGCGACG*
*TGTACATCACCGACAAGACAGTGCTGGATATGCGGAGCATGGACTTCAAGTCTAACAGC*
*GCCGTGGCCTGGAGCAATAAGTCCGATTTCGCCTGCGCCAATGCCTTTAACAATTCCAT*
*CATCCCTGAGGATACCTTCTTTCCATCTCCCGAGAGCTCCTGTGACGTGAAGCTGGTGG*
*AGAAGTCTTTCGAGACCGATACAAACCTGAATTTTCAGAACCTGAGCGTGATCGGCTTC*
*CGGATCCTGCTGCTGAAGGTGGCCGGCTTCAATCTGCTGATGACACTGAGACTGTGGTC*
*TAGCTGATGA*

Amino Acid sequence

MTIRLLCYMGFYFLGAGLMEADIYQTPRYLVIGTGKKITLECSQTMGHDKM
YWYQQDPGMELHLIHYSYGVNSTEKGDLSSESTVSRIRTEHFPLTLESARP
SHTSQYLCASSPPGQPYEQYFGPGTRLTVT*EDLNKVFPPEVAVFEPSEAEISHT*
*QKATLVCLATGFFPDHVELSWWVNGKEVHSGVSTDPQPLKEQPALNDSRYCLSSRLRVS*
*ATFWQNPRNHFRCQVQFYGLSENDEWTQDRAKPVTQIVSAEAWGRADCGFTSVSYQQGV*
*LSATILYEILLGKATLYAVLVSALVLMAMVKRKDF*RAKRSGSGATNFSLLKQAGDVEEN
PGPMEKMLECAFIVLWLQLGWLSGEDQVTQSPEALRLQEGESSSLNCSYTV
SGLRGLFWYRQDPGKGPEFLFTLYSAGEEKEKERLKATLTKKESFLHITAP
KPEDSATYLCAVRMNTGFQKLVFGTGTRLLVSP*NIQNPDPAVYQLRDSKSSDKS*
*VCLFTDFDSQTNVSQSKDSDVYITDKTVLDMRSMDFKSNSAVAWSNKSDFACANAFNNS*
*IIPEDTFFPSPESSCDVKLVEKSFETDTNLNFQNLSVIGFRILLLKVAGFNLLMTLRLW*
*SS*

FIGURE 10

| Sequence | Sequence Identifier |
|---|---|
| SGDLS | 1 |
| YYNGEE | 2 |
| ASSAAVHYGYT | 3 |
| MGFRLLCCVAFCLLGAGPVDSGVTQTPKHLITATGQQVTLRCSPR | 4 |
| VYWYQQSLDQGLQFLIQ | 5 |
| RAKGNILERFSAQQFPDLHSELNLSSLELGDSALYFC | 6 |
| FGSGTRLTVV | 7 |
| EDLRNVTPPKVSLFEPSKAEIANKQKATLVCLARGFFPDHVELSWWVNGKEVHSGVCTD<br>PQAYKESNYSYCLSSRLRVSATFWHNPRNHFRCQVQFHGLSEEDKWPEGSPKPVTQNISA<br>EAWGRADCGITSASYQQGVLSATILYEILLGKATLYAVLVSTLVVMAMVKRKNS | 8 |
| MGFRLLCCVAFCLLGAGPVDSGVTQTPKHLITATGQQVTLRCSPRSGDLSVYWYQQSLDQ<br>GLQFLIQYYNGEERAKGNILERFSAQQFPDLHSELNLSSLELGDSALYFCASSAAVHYGYTF<br>GSGTRLTVV | 47 |
| MGFRLLCCVAFCLLGAGPVDSGVTQTPKHLITATGQQVTLRCSPRSGDLSVYWYQQSLDQG<br>LQFLIQYYNGEERAKGNILERFSAQQFPDLHSELNLSSLELGDSALYFCASSAAVHYGYTFGS<br>GTRLTVVEDLRNVTPPKVSLFEPSKAEIANKQKATLVCLARGFFPDHVELSWWVNGKEVHS | 9 |

FIGURE 10 (Cont.)

| GVCTDPQAYKESNYSYCLSSRLRVSATFWHNPRNHFRCQVQFHGLSEEDKWPEGSPKPVT QNISAEAWGRADCGITSASYQQGVLSATILYEILLGKATLYAVLVSTLVVMAMVKRKNS | |
|---|---|
| TSDQSYG | 10 |
| QGSYDEQN | 11 |
| AMREQGAQKLV | 12 |
| MSLSSLLKVVTASLWLGPGIAQKITQTQPGMFVQEKEAVTLDCTYD | 13 |
| LFWYKQPSSGEMIFLIY | 14 |
| ATEGRYSLNFQKARKSANLVISASQLGDSAMYFC | 15 |
| FGQGTRLTINP | 16 |
| NIQNPEPAVYQLKDPRSQDSTLCLFTDFDSQINVPKTMESGTFITDKCVLD MKAMDSKSNGAIAWSNQTSFTCQDIFKETNATYPSSDVPCDATLTEKSFETDMNLNFQ NLLVIVLRILLLKVAGFNLLMTLRLWSS | 17 |
| MSLSSLLKVVTASLWLGPGIAQKITQTQPGMFVQEKEAVTLDCTYDTSDQSYGLFWYK QPSSGEMIFLIYQGSYDEQNATEGRYSLNFQKARKSANLVISASQLGDSAMYFCAMREQ GAQKLVFGQGTRLTINP | 45 |
| MSLSSLLKVVTASLWLGPGIAQKITQTQPGMFVQEKEAVTLDCTYDTSDQSYGLFWYKQ PSSGEMIFLIYQGSYDEQNATEGRYSLNFQKARKSANLVISASQLGDSAMYFCAMREQGA QKLVFGQGTRLTINPNIQNPEPAVYQLKDPRSQDSTLCLFTDFDSQINVPKTMESGTFITDK | 18 |

FIGURE 10 (Cont.)

| | |
|---|---|
| CVLDMKAMDSKSNGAIAWSNQTSFTCQDIFKETNATYPSSDVPCDATLTEKSFETDMNLN FQNLLVIVLRILLLKVAGFNLLMTLRLWSS | |
| EDLNKVFPPEVAVFEPSEAEISHTQKATLVCLATGFFPDHVELSWWVNGKEVHSGVSTDP QPLKEQPALNDSRYCLSSRLRVSATFWQNPRNHFRCQVQFYGLSENDEWTQDRAKPVTQI VSAEAWGRADCGFTSVSYQQGVLSATILYEILLGKATLYAVLVSALVLMAMVKRKDF | 19 |
| MGFRLLCCVAFCLLGAGPVDSGVTQTPKHLITATGQQVTLRCSPRSGDLSVYWYQQSLDQ GLQFLIQYYNGEERAKGNILERFSAQQFPDLHSELNLSSLELGDSALYFCASSAAVHYGYTF GSGTRLTVVEDLNKVFPPEVAVFEPSEAEISHTQKATLVCLATGFFPDHVELSWWVNGKEV HSGVSTDPQPLKEQPALNDSRYCLSSRLRVSATFWQNPRNHFRCQVQFYGLSENDEWTQDR AKPVTQIVSAEAWGRADCGFTSVSYQQGVLSATILYEILLGKATLYAVLVSALVLMAMVKRKDF | 20 |
| NIQNPDPAVYQLRDSKSSDKSVCLFTDFDSQTNVSQSKDSDVYITDKTVLDMRSMDFKSNSA VAWSNKSDFACANAFNNSIIPEDTFFPSPESSCDVKLVEKSFETDTNLNFQNLSVIGFRILLLK VAGFNLLMTLRLWSS | 21 |
| MSLSSLLKVVTASLWLGPGIAQKITQTQPGMFVQEKEAVTLDCTYDTSDQSYGLFWYKQPSS GEMIFLIYQGSYDEQNATEGRYSLNFQKARKSANLVISASQLGDSAMYFCAMREQGAQKLV FGQGTRLTINPNIQNPDPAVYQLRDSKSSDKSVCLFTDFDSQTNVSQSKDSDVYITDKTVLDM RSMDFKSNSAVAWSNKSDFACANAFNNSIIPEDTFFPSPESSCDVKLVEKSFETDTNLNFQNL SVIGFRILLLKVAGFNLLMTLRLWSS | 22 |

Figure 10 (Cont.)

| MGHDK | 23 |
| --- | --- |
| SYGVNS | 24 |
| ASSPPGQPYEQY | 25 |
| MTIRLLCYMGFYFLGAGLMEADIYQTPRYLVIGTGKKITLECSQT | 26 |
| MYWYQQDPGMELHLIHY | 27 |
| TEKGDLSSESTVSRIRTEHFPLTLESARPSHTSQYLC | 28 |
| FGPGTRLTVT | 29 |
| EDLRNVTPPKVSLFEPSKAEIANKQKATLVCLARGFFPDHVELSWWVNGKEVHSG<br>VCTDPQAYKESNYSYCLSSRLRVSATFWHNPRNHFRCQVQFHGLSEEDKWPEGSP<br>KPVTQNISAEAWGRADCGITSASYQQGVLSATILYEILLGKATLYAVLVSTLVVMAMVKRKNS | 30 |
| MTIRLLCYMGFYFLGAGLMEADIYQTPRYLVIGTGKKITLECSQTMGHDKMYWYQQDPGME<br>LHLIHYSYGVNSTEKGDLSSESTVSRIRTEHFPLTLESARPSHTSQYLCASSPPGQPYEQYFGPGT<br>RLTVT | 48 |
| MTIRLLCYMGFYFLGAGLMEADIYQTPRYLVIGTGKKITLECSQTMGHDKMYWYQQDPGMEL<br>HLIHYSYGVNSTEKGDLSSESTVSRIRTEHFPLTLESARPSHTSQYLCASSPPGQPYEQYFGPGTR<br>LTVTEDLRNVTPPKVSLFEPSKAEIANKQKATLVCLARGFFPDHVELSWWVNGKEVHSGVCTD<br>PQAYKESNYSYCLSSRLRVSATFWHNPRNHFRCQVQFHGLSEEDKWPEGSPKPVTQNISAEAW<br>GRADCGITSASYQQGVLSATILYEILLGKATLYAVLVSTLVVMAMVKRKNS | 31 |

Figure 10 (Cont.)

| | |
|---|---|
| VSGLRG | 32 |
| LYSAGEE | 33 |
| AVRMNTGFQKLV | 34 |
| MEKMLECAFIVLWLQLGWLSGEDQVTQSPEALRLQEGESSSLNCSYT | 35 |
| LFWYRQDPGKGPEFLFT | 36 |
| KEKERLKATLTKKESFLHITAPKPEDSATYLC | 37 |
| FGTGTRLLVSP | 38 |
| NIQNPEPAVYQLKDPRSQDSTLCLFTDFDSQINVPKTMESGTFITDKCVLDMKAMDS KSNGAIAWSNQTSFTCQDIFKETNATYPSSDVPCDATLTEKSFETDMNLNFQNLLVIV LRILLLKVAGFNLLMTLRLWSS | 39 |
| MEKMLECAFIVLWLQLGWLSGEDQVTQSPEALRLQEGESSSLNCSYTVSGLRGLFWY RQDPGKGPEFLFTLYSAGEEKEKERLKATLTKKESFLHITAPKPEDSATYLCAVRMNT GFQKLVFGTGTRLLVSP | 46 |
| MEKMLECAFIVLWLQLGWLSGEDQVTQSPEALRLQEGESSSLNCSYTVSGLRGLFWYR QDPGKGPEFLFTLYSAGEEKEKERLKATLTKKESFLHITAPKPEDSATYLCAVRMNTGFQ KLVFGTGTRLLVSPNIQNPEPAVYQLKDPRSQDSTLCLFTDFDSQINVPKTMESGTFITDK CVLDMKAMDSKSNGAIAWSNQTSFTCQDIFKETNATYPSSDVPCDATLTEKSFETDMNLN FQNLLVIVLRILLLKVAGFNLLMTLRLWSS | 40 |

Figure 10 (Cont.)

| | |
|---|---|
| EDLNKVFPPEVAVFEPSEAEISHTQKATLVCLATGFFPDHVELSWWVNGKEVHS GVSTDPQPLKEQPALNDSRYCLSSRLRVSATFWQNPRNHFRCQVQFYGLSENDE WTQDRAKPVTQIVSAEAWGRADCGFTSVSYQQGVLSATILYEILLGKATLYAVL VSALVLMAMVKRKDF | 41 |
| MTIRLLCYMGFYFLGAGLMEADIYQTPRYLVIGTGKKITLECSQTMGHDKMYW YQQDPGMELHLIHYSYGVNSTEKGDLSSESTVSRIRTEHFPLTLESARPSHTSQYL CASSPPGQPYEQYFGPGTRLTVTEDLNKVFPPEVAVFEPSEAEISHTQKATLVCLA TGFFPDHVELSWWVNGKEVHSGVSTDPQPLKEQPALNDSRYCLSSRLRVSATFW QNPRNHFRCQVQFYGLSENDEWTQDRAKPVTQIVSAEAWGRADCGFTSVSYQQ GVLSATILYEILLGKATLYAVLVSALVLMAMVKRKDF | 42 |
| NIQNPDPAVYQLRDSKSSDKSVCLFTDFDSQTNVSQSKDSDVYITDKTVLDMRSM DFKSNSAVAWSNKSDFACANAFNNSIIPEDTFFPSPESSCDVKLVEKSFETDTNLN FQNLSVIGFRILLLKVAGFNLLMTLRLWSS | 43 |
| MEKMLECAFIVLWLQLGWLSGEDQVTQSPEALRLQEGESSSLNCSYTVSGLRGLF WYRQDPGKGPEFLFTLYSAGEEKEKERLKATLTKKESFLHITAPKPEDSATYLCA VRMNTGFQKLVFGTGTRLLVSPNIQNPDPAVYQLRDSKSSDKSVCLFTDFDSQTN VSQSKDSDVYITDKTVLDMRSMDFKSNSAVAWSNKSDFACANAFNNSIIPEDTFF PSPESSCDVKLVEKSFETDTNLNFQNLSVIGFRILLLKVAGFNLLMTLRLWSS | 44 |

FIGURE 11A

Nucleotide sequence encoding beta chain of TRBV9*01 + TRAV14/DV4 chimeric TCR, with human beta variable region in larger font, CDR1, CDR2, CDR3 underlined, and mouse beta constant (codon optimized) in italics

Nucleotide sequence

ATGGGCTTCAGGCTCCTCTGCTGTGTGGCCTTTTGTCTCCTGGGAGCAGGCCCAGTGGATTCTGGAGTCACACAAAC
CCCAAAGCACCTGATCACAGCAACTGGACAGCAAGTGACGCTGAGATGCTCCCCTAGGTCTGGAGACCTCTCTGTGT
ACTGGTACCAACAGAGCCTGGACCAGGGCCTCCAGTTCCTCATTCAGTATTATAATGGAGAAGAGAGAGCAAAAGGA
AACATTCTTGAACGATTCTCCGCACAACAGTTCCCTGACTTGCACTCTGAACTAAACCTGAGCTCTCTGGAGCTGGG
GGACTCAGCTTTGTATTTCTGTGCCAGCAGCGCGGCAGTTCACTATGGCTACACCTTCGGTTCGGGGACCAGGTTAA
CCGTTGTA*GAGGACCTGAGAAACGTGACACCCCCTAAGGTGAGCCTGTTCGAGCCCTCCAAGGCCGAGATCGCCAATAAGCAGAAGGC*
*CACCCTGGTGTGCCTGGCAAGGGGCTTCTTTCCTGATCACGTGGAGCTGTCTTGGTGGGTGAACGGCAAGGAGGTGCACAGCGGCGTGT*
*GCACCGACCCACAGGCCTATAAGGAGAGCAATTATTCCTACTGTCTGTCTAGCCGGCTGAGAGTGAGCGCCACATTTTGGCACAACCCT*
*CGGAATCACTTCAGATGCCAGGTGCAGTTTCACGGCCTGTCTGAGGAGGATAAGTGGCCAGAGGGCAGCCCAAAGCCAGTGACCCAGAA*
*CATCTCCGCCGAGGCATGGGGAAGAGCAGACTGTGGCATCACCAGCGCCTCCTACCAGCAGGGCGTGCTGTCCGCCACAATCCTGTATG*
*AGATCCTGCTGGGCAAGGCCACCCTGTACGCCGTGCTGGTGAGCACACTGGTGGTCATGGCTATGGTGAAGAGGAAGAACTCC*

FIGURE 11B

Nucleotide sequence encoding alpha chain of TRBV9*01 + TRAV14/DV4 chimeric TCR including human alpha variable region in larger font, CDR1, CDR2, CDR3 underlined, and mouse alpha constant (codon optimized) in italics ATGTCACTTTCTAGCCTGCTGAAGGTGGTCACAGCTTCACTGTGGCTAGGACCTGGCATTGCCCAGAAGATAACTCA
AACCCAACCAGGAATGTTCGTGCAGGAAAAGGAGGCTGTGACTCTGGACTGCACATATGACACCAGTGATCAAAGTT
ATGGTCTCTTCTGGTACAAGCAGCCCAGCAGTGGGGAAATGATTTTTCTTATTTATCAGGGGTCTTATGACGAGCAA
AATGCAACAGAAGGTCGCTACTCATTGAATTTCCAGAAGGCAAGAAAATCCGCCAACCTTGTCATCTCCGCTTCACA
ACTGGGGGACTCAGCAATGTATTTCTGTGCAATGAGAGAGCAGGGAGCCCAGAAGCTGGTATTTGGCCAAGGAACCA
GGCTGACTATCAACCCA*AACATCCAGAATCCAGAGCCCGCCGTGTATCAGCTGAAGGACCCAAGATCCCAGGATTCTACCCTGTGCC*

FIGURE 11B (Cont.)

*TGTTCACAGACTTTGATTCTCAGATCAATGTGCCCAAGACAATGGAGAGCGGCACCTTCATCACAGACAAGTGCGTGCTGGATATGAAG*
*GCTATGGACTCCAAGTCTAACGGCGCCATCGCCTGGAGCAATCAGACCTCCTTCACATGCCAGGATATCTTTAAGGAGACAAACGCCAC*
*ATACCCTTCTAGCGACGTGCCATGTGATGCCACCCTGACAG*AGAAGAGCTTCGAGACAGACATGAACCTGAATTTTCAGAATCTGCTGG
TCATCGTGCTGCGGATCCTGCTGCTGAAGGTGGCTGGGTTTAATCTGCTGATGACACTGCGACTGTGGAGTAGCTGATGA

FIGURE 12A

Codon optimized nucleotide sequence encoding the beta chain of TRBV9*01 + TRAV14/DV4 chimeric TCR, with human beta variable region in larger font, CDR1, CDR2, CDR3 underlined, and mouse beta constant in italics ATGGGCTTCCGGCTGCTGTGCTGCGTGGCATTTTGCCTGCTGGGAGCAGGACCTGTGGATAGCGGCGTGACCCAGAC
ACCAAAGCACCTGATCACCGCAACAGGACAGCAGGTGACCCTGAGGTGTTCCCCAAGATCTGGCGATCTGTCCGTGT
ACTGGTATCAGCAGTCTCTGGACCAGGGCCTGCAGTTCCTGATCCAGTACTATAACGGCGAGGAGCGGGCCAAGGGC
AATATCCTGGAGAGATTCAGCGCCCAGCAGTTTCCTGATCTGCACTCCGAGCTGAATCTGAGCTCCCTGGAGCTGGG
CGACTCCGCCCTGTACTTCTGCGCCTCTAGCGCCGCAGTGCACTACGGCTATACCTTTGGCTCTGGCACCAGGCTGA
CAGTGGTG*GAGGACCTGCGCAATGTGACACCCCCTAAGGTGTCTCTGTTCGAGCCCAGCAAGGCCGAGATCGCCAACAAGCAGAAGGC*
*CACCCTGGTGTGCCTGGCCCGGGGCTTCTTTCCTGATCACGTGGAGCTGTCCTGGTGGGTGAATGGCAAGGAGGTGCACTCTGGCGTGT*
*GCACCGACCCACAGGCCTACAAGGAGAGCAACTACTCCTATTGTCTGTCCTCTCGGCTGAGAGTGAGCGCCACATTTTGGCACAACCCT*
*AGGAATCACTTCCGCTGCCAGGTGCAGTTTCACGGCCTGTCTGAGGAGGATAAGTGGCCAGAGGGAAGCCCAAAGCCAGTGACCCAGAA*
*TATCTCCGCCGAGGCATGGGGAAGGGCAGACTGTGGAATCACCTCTGCCAGCTATCAGCAGGGCGTGCTGTCCGCCACAATCCTGTACG*
*AGATCCTGCTGGGCAAGGCCACCCTGTATGCCGTGCTGGTGTCCACACTGGTGGTCATGGCTATGGTGAAGAGGAAGAACAGC*

FIGURE 12B

Codon optimized nucleotide sequence encoding the alpha chain of TRBV9*01 + TRAV14/DV4 chimeric TCR including human alpha variable region in larger font, CDR1, CDR2, CDR3 underlined, and mouse alpha constant in italics ATGTCTCTGAGCTCCCTGCTGAAGGTCGTGACAGCAAGCCTGTGGCTGGGACCAGGAATCGCACAGAAGATCACCCA
GACACAGCCTGGCATGTTTGTGCAGGAGAAGGAGGCCGTGACCCTGGACTGCACCTACGACACATCTGATCAGAGCT
ACGGCCTGTTCTGGTATAAGCAGCCATCTAGCGGCGAGATGATCTTTCTGATCTACCAGGGCAGCTATGATGAGCAG
AACGCCACAGAGGGCCGGTACTCTCTGAATTTCCAGAAGGCCAGAAAGAGCGCCAACCTGGTCATCAGCGCCTCCCA
GCTGGGCGACTCCGCCATGTATTTCTGTGCCATGAGGGAGCAGGGCGCCCAGAAGCTGGTGTTTGGCCAGGGCACCC
GCCTGACAATCAACCCA*AATATCCAGAATCCCGAGCCTGCCGTGTACCAGCTGAAGGACCCCAGATCCCAGGATTCTACCCTGTGCC*

FIGURE 12B (Cont.)

*TGTTCACAGACTTTGATAGCCAGATCAACGTGCCCAAGACAATGGAGTCCGGCACCTTCATCACAGACAAGTGCGTGCTGGACATGAAG*
*GCTATGGACTCTAAGAGCAACGGCGCCATCGCCTGGAGCAATCAGACCTCCTTCACATGCCAGGATATCTTTAAGGAGACCAACGCCAC*
*ATATCCATCCTCTGACGTGCCCTGTGATGCCACCCTGACAGAGAAGTCCTTCGAGACCGACATGAACCTGAATTTTCAGAATCTGCTGG*
*TCATCGTGCTGCGGATCCTGCTGCTGAAGGTGGCCGGCTTTAACCTGCTGATGACACTGAGACTGTGGAGCTCCTGATGA*

FIGURE 13A

Nucleotide sequence encoding beta chain of TRBV9*01 + TRAV14/DV4 human TCR, with human beta variable region in larger font, CDR1, CDR2, CDR3 underlined, and human beta constant in italics ATGGGCTTCAGGCTCCTCTGCTGTGTGGCCTTTTGTCTCCTGGGAGCAGGCCCAGTGGATTCTGGAGTCACACAAAC
CCCAAAGCACCTGATCACAGCAACTGGACAGCAAGTGACGCTGAGATGCTCCCCTAGGTCTGGAGACCTCTCTGTGT
ACTGGTACCAACAGAGCCTGGACCAGGGCCTCCAGTTCCTCATTCAGTATTATAATGGAGAAGAGAGAGCAAAAGGA
AACATTCTTGAACGATTCTCCGCACAACAGTTCCCTGACTTGCACTCTGAACTAAACCTGAGCTCTCTGGAGCTGGG
GGACTCAGCTTTGTATTTCTGTGCCAGCAGCGCGGCAGTTCACTATGGCTACACCTTCGGTTCGGGGACCAGGTTAA
CCGTTGTA*GAGGACCTGAACAAGGTGTTCCCACCCGAGGTCGCTGTGTTTGAGCCATCAGAAGCAGAGATCTCCCACACCCAAAAGGC*
*CACACTGGTGTGCCTGGCCACAGGCTTCTTCCCCGACCACGTGGAGCTGAGCTGGTGGGTGAATGGGAAGGAGGTGCACAGTGGGGTCA*
*GCACGGACCCGCAGCCCCTCAAGGAGCAGCCCGCCCTCAATGACTCCAGATACTGCCTGAGCAGCCGCCTGAGGGTCTCGGCCACCTTC*
*TGGCAGAACCCCCGCAACCACTTCCGCTGTCAAGTCCAGTTCTACGGGCTCTCGGAGAATGACGAGTGGACCCAGGATAGGGCCAAACC*
*CGTCACCCAGATCGTCAGCGCCGAGGCCTGGGGTAGAGCAGACTGTGGCTTTACCTCGGTGTCCTACCAGCAAGGGGTCCTGTCTGCCA*
*CCATCCTCTATGAGATCCTGCTAGGGAAGGCCACCCTGTATGCTGTGCTGGTCAGCGCCCTTGTGTTGATGGCCATGGTCAAGAGAAAG*
*GATTTC*

FIGURE 13B

Nucleotide sequence encoding alpha chain of TRBV9*01 + TRAV14/DV4 human TCR including human alpha variable region in larger font, CDR1, CDR2, CDR3 underlined, and human alpha constant in italics ATGTCACTTTCTAGCCTGCTGAAGGTGGTCACAGCTTCACTGTGGCTAGGACCTGGCATTGCCCAGAAGATAACTCA
AACCCAACCAGGAATGTTCGTGCAGGAAAAGGAGGCTGTGACTCTGGACTGCACATATGACACCAGTGATCAAAGTT
ATGGTCTCTTCTGGTACAAGCAGCCCAGCAGTGGGGAAATGATTTTTCTTATTTATCAGGGGTCTTATGACGAGCAA
AATGCAACAGAAGGTCGCTACTCATTGAATTTCCAGAAGGCAAGAAAATCCGCCAACCTTGTCATCTCCGCTTCACA FIGURE 13B (Cont.)

ACTGGGGGACTCAGCAATGTATTTCTGTGCAATGAGAGAGCAGGGAGCCCAGAAGCTGGTATTTGGCCAAGGAACCA
GGCTGACTATCAACCCA*AATATCCAGAACCCTGACCCTGCCGTGTACCAGCTGAGAGACTCTAAATCCAGTGACAAGTCTGTCTGCC*
*TATTCACCGATTTTGATTCTCAAACAAATGTGTCACAAAGTAAGGATTCTGATGTGTATATCACAGACAAAACTGTGCTAGACATGAGG*
*TCTATGGACTTCAAGAGCAACAGTGCTGTGGCCTGGAGCAACAAATCTGACTTTGCATGTGCAAACGCCTTCAACAACAGCATTATTCC*
*AGAAGACACCTTCTTCCCCAGCCCAGAAAGTTCCTGTGATGTCAAGCTGGTCGAGAAAAGCTTTGAAACAGATACGAACCTAAACTTTC*
*AAAACCTGTCAGTGATTGGGTTCCGAATCCTCCTCCTGAAAGTGGCCGGGTTTAATCTGCTCATGACGCTGCGGCTGTGGTCCAGCTGA*
*TGA*

FIGURE 14A

Codon optimized nucleotide sequence encoding the beta chain of TRBV9*01 + TRAV14/DV4 human TCR, with human beta variable region in larger font, CDR1, CDR2, CDR3 underlined, and human beta constant in italics ATGGGCTTCCGGCTGCTGTGCTGCGTGGCATTTTGCCTGCTGGGAGCAGGACCTGTGGATAGCGGCGTGACCCAGAC
ACCAAAGCACCTGATCACCGCAACAGGACAGCAGGTGACCCTGAGGTGTTCCCCAAGATCTGGCGATCTGTCCGTGT
ACTGGTATCAGCAGTCTCTGGACCAGGGCCTGCAGTTCCTGATCCAGTACTATAACGGCGAGGAGCGGGCCAAGGGC
AATATCCTGGAGAGATTCAGCGCCCAGCAGTTTCCTGATCTGCACTCCGAGCTGAATCTGAGCTCCCTGGAGCTGGG
CGACTCCGCCCTGTACTTCTGCGCCTCTAGCGCCGCAGTGCACTACGGCTATACCTTTGGCTCTGGCACCAGGCTGA
CAGTGGTG*GAGGACCTGAATAAGGTGTTCCCCCCTGAGGTGGCCGTGTTTGAGCCTTCCGAGGCCGAGATCTCTCACACCCAGAAGGC*
*CACCCTGGTGTGCCTGGCAACCGGCTTCTTTCCAGATCACGTGGAGCTGAGCTGGTGGGTGAACGGCAAGGAGGTGCACAGCGGCGTGT*
*CCACCGACCCACAGCCCCTGAAGGAGCAGCCCGCCCTGAATGATAGCAGATATTGCCTGTCTAGCCGGCTGAGAGTGTCCGCCACCTTT*
*TGGCAGAACCCTCGGAATCACTTCAGATGTCAGGTGCAGTTTTACGGCCTGAGCGAGAATGACGAGTGGACCCAGGATAGGGCCAAGCC*
*CGTGACACAGATCGTGTCCGCCGAGGCATGGGGAAGGGCAGACTGCGGCTTCACATCCGTGTCTTATCAGCAGGGCGTGCTGAGCGCCA*
*CCATCCTGTATGAGATCCTGCTGGGCAAGGCCACACTGTACGCCGTGCTGGTGTCCGCCCTGGTGCTGATGGCTATGGTGAAGCGGAAG*
*GACTTT*

FIGURE 14B

Codon optimized nucleotide sequence encoding the alpha chain of TRBV9*01 + TRAV14/DV4 human TCR including human alpha variable region in larger font, CDR1, CDR2, CDR3 underlined, and human alpha constant in italics ATGTCTCTGAGCTCCCTGCTGAAGGTCGTGACAGCAAGCCTGTGGCTGGGACCAGGAATCGCACAGAAGATCACCCA
GACACAGCCTGGCATGTTTGTGCAGGAGAAGGAGGCCGTGACCCTGGACTGCACCTACGACACATCTGATCAGAGCT
ACGGCCTGTTCTGGTATAAGCAGCCATCTAGCGGCGAGATGATCTTTCTGATCTACCAGGGCAGCTATGATGAGCAG
AACGCCACAGAGGGCCGGTACTCTCTGAATTTCCAGAAGGCCAGAAAGAGCGCCAACCTGGTCATCAGCGCCTCCCA
GCTGGGCGACTCCGCCATGTATTTCTGTGCCATGAGGGAGCAGGGCGCCCAGAAGCTGGTGTTTGGCCAGGGCACCC FIGURE 14B (Cont.)

GCCTGACAATCAACCCA*AACATCCAGAATCCCGACCCTGCCGTGTATCAGCTGAGGGACTCCAAGTCCTCTGATAAGAGCGTGTGCC*
*TGTTCACCGACTTTGATTCTCAGACAAACGTGAGCCAGTCCAAGGACAGCGACGTGTACATCACCGACAAGACAGTGCTGGATATGCGG*
*AGCATGGACTTCAAGTCTAACAGCGCCGTGGCCTGGAGCAATAAGTCCGATTTCGCCTGCGCCAATGCCTTTAACAATTCCATCATCCC*
*TGAGGATACCTTCTTTCCATCTCCCGAGAGCTCCTGTGACGTGAAGCTGGTGGAGAAGTCTTTCGAGACCGATACAAACCTGAATTTTC*
*AGAACCTGAGCGTGATCGGCTTCCGGATCCTGCTGCTGAAGGTGGCCGGCTTCAATCTGCTGATGACACTGAGACTGTGGTCTAGCTGA*
*TGA*

FIGURE 15A

Nucleotide sequence encoding the beta chain of TRBV25-1 + TRAV20 chimeric TCR with human beta variable region in larger font, CDR1, CDR2, CDR3 underlined, and mouse beta constant (codon optimized) in italics.

ATGACTATCAGGCTCCTCTGCTACATGGGCTTTTATTTTCTGGGGGCAGGCCTCATGGAAGCTGACATCTACCAGAC
CCCAAGATACCTTGTTATAGGGACAGGAAAGAAGATCACTCTGGAATGTTCTCAAACCATGGGCCATGACAAAATGT
ACTGGTATCAACAAGATCCAGGAATGGAACTACACCTCATCCACTATTCCTATGGAGTTAATTCCACAGAGAAGGGA
GATCTTTCCTCTGAGTCAACAGTCTCCAGAATAAGGACGGAGCATTTTCCCCTGACCCTGGAGTCTGCCAGGCCCTC
ACATACCTCTCAGTACCTCTGTGCCAGCAGTCCGCCGGGACAGCCTTACGAGCAGTACTTCGGGCCGGGCACCAGGC
TCACGGTCACA*GAGGACCTGAGAAACGTGACACCCCCTAAGGTGAGCCTGTTCGAGCCCTCCAAGGCCGAGATCGCCAATAAGCAGAA*
*GGCCACCCTGGTGTGCCTGGCAAGGGGCTTCTTTCCTGATCACGTGGAGCTGTCTTGGTGGGTGAACGGCAAGGAGGTGCACAGCGGCG*
*TGTGCACCGACCCACAGGCCTATAAGGAGAGCAATTATTCCTACTGTCTGTCTAGCCGGCTGAGAGTGAGCGCCACATTTTGGCACAAC*
*CCTCGGAATCACTTCAGATGCCAGGTGCAGTTTCACGGCCTGTCTGAGGAGGATAAGTGGCCAGAGGGCAGCCCAAAGCCAGTGACCCA*
*GAACATCTCCGCCGAGGCATGGGGAAGAGCAGACTGTGGCATCACCAGCGCCTCCTACCAGCAGGGCGTGCTGTCCGCCACAATCCTGT*
*ATGAGATCCTGCTGGGCAAGGCCACCCTGTACGCCGTGCTGGTGAGCACACTGGTGGTCATGGCTATGGTGAAGAGGAAGAACTCC*

FIGURE 15B

Nucleotide sequence encoding the alpha chain of TRBV25-1 + TRAV20 chimeric TCR, with the human variable region in larger font, CDR1, CDR2, CDR3 underlined, and mouse alpha constant (codon optimized) in italics ATGGAGAAAATGTTGGAGTGTGCATTCATAGTCTTGTGGCTTCAGCTTGGCTGGTTGAGTGGAGAAGACCAGGTGAC
GCAGAGTCCCGAGGCCCTGAGACTCCAGGAGGGAGAGAGTAGCAGTCTCAACTGCAGTTACACAGTCAGCGGTTTAA
GAGGGCTGTTCTGGTATAGGCAAGATCCTGGGAAAGGCCCTGAATTCCTCTTCACCCTGTATTCAGCTGGGGAAGAA
AAGGAGAAAGAAAGGCTAAAAGCCACATTAACAAAGAAGGAAAGCTTTCTGCACATCACAGCCCCTAAACCTGAAGA
CTCAGCCACTTATCTCTGTGCTGTGCGGATGAACACAGGCTTTCAGAAACTTGTATTTGGAACTGGCACCCGACTTC
TGGTCAGTCCA*AACATCCAGAATCCAGAGCCCGCCGTGTATCAGCTGAAGGACCCAAGATCCCAGGATTCTACCCTGTGCCTGTTCAC*

FIGURE 15B (Cont.)

AGACTTTGATTCTCAGATCAATGTGCCCAAGACAATGGAGAGCGGCACCTTCATCACAGACAAGTGCGTGCTGGATATGAAGGCTATGG
ACTCCAAGTCTAACGGCGCCATCGCCTGGAGCAATCAGACCTCCTTCACATGCCAGGATATCTTTAAGGAGACAAACGCCACATACCCT
TCTAGCGACGTGCCATGTGATGCCACCCTGACAGAGAAGAGCTTCGAGACAGACATGAACCTGAATTTTCAGAATCTGCTGGTCATCGT
GCTGCGGATCCTGCTGCTGAAGGTGGCTGGGTTTAATCTGCTGATGACACTGCGACTGTGGAGTAGCTGATGA

FIGURE 16A

Codon optimized nucleotide sequence encoding the beta chain of TRBV25-1 + TRAV20 chimeric TCR with human beta variable region in larger font, CDR1, CDR2, CDR3 underlined, and mouse beta constant in italics.

ATGACCATCCGGCTGCTGTGCTACATGGGCTTCTATTTTCTGGGCGCCGGCCTGATGGAGGCCGATATCTACCAGAC
CCCCAGATACCTGGTCATCGGCACCGGCAAGAAGATCACACTGGAGTGTTCCCAGACAATGGGCCACGATAAGATGT
ACTGGTATCAGCAGGACCCTGGCATGGAGCTGCACCTGATCCACTACTCCTATGGCGTGAACTCTACCGAGAAGGGC
GACCTGAGCTCCGAGTCCACCGTGTCTCGGATCAGAACAGAGCACTTCCCACTGACCCTGGAGAGCGCCAGGCCTAG
CCACACATCCCAGTACCTGTGCGCCTCTAGCCCACCTGGACAGCCTTACGAGCAGTATTTCGGCCCAGGCACCAGGC
TGACCGTGACA*GAGGATCTGCGCAACGTGACACCACCCAAGGTGAGCCTGTTTGAGCCCTCCAAGGCCGAGATCGCCAATAAGCAGAA*
*GGCCACCCTGGTGTGCCTGGCCCGCGGCTTCTTTCCTGATCACGTGGAGCTGTCCTGGTGGGTGAACGGCAAGGAGGTGCACTCTGGCG*
*TGTGCACCGACCCACAGGCCTATAAGGAGTCTAATTACAGCTATTGTCTGTCCTCTAGGCTGCGCGTGTCCGCCACATTCTGGCACAAC*
*CCTAGGAATCACTTCCGCTGCCAGGTGCAGTTTCACGGCCTGTCCGAGGAGGATAAGTGGCCAGAGGGCTCTCCTAAGCCAGTGACCCA*
*GAATATCAGCGCCGAGGCATGGGGAAGGGCAGACTGTGGAATCACCTCCGCCTCTTACCAGCAGGGCGTGCTGAGCGCCACAATCCTGT*
*ACGAGATCCTGCTGGGCAAGGCCACACTGTATGCCGTGCTGGTGTCCACCCTGGTGGTCATGGCTATGGTGAAGCGCAAGAACTCT*

FIGURE 16B

Codon optimized nucleotide sequence encoding the alpha chain of TRBV25-1 + TRAV20 chimeric TCR with human alpha variable region in larger font, CDR1, CDR2, CDR3 underlined, and mouse alpha constant in italics.

ATGGAGAAGATGCTGGAGTGCGCCTTTATCGTGCTGTGGCTGCAGCTGGGATGGCTGTCTGGAGAGGACCAGGTGAC
CCAGAGCCCAGAGGCCCTGAGGCTGCAGGAGGGAGAGAGCTCCTCTCTGAATTGTAGCTACACAGTGTCCGGCCTGC
GGGGCCTGTTCTGGTATAGACAGGATCCCGGCAAGGGCCCTGAGTTCCTGTTTACCCTGTACTCCGCCGGCGAGGAG
AAGGAGAAGGAGAGACTGAAGGCCACCCTGACAAAGAAGGAGTCTTTTCTGCACATCACAGCCCCAAAGCCCGAGGA
CAGCGCCACCTATCTGTGCGCCGTGCGGATGAACACAGGCTTCCAGAAGCTGGTGTTTGGCACCGGCACAAGACTGC
TGGTGAGCCCA*AACATCCAGAATCCTGAGCCAGCCGTGTACCAGCTGAAGGACCCCCGGTCCCAGGATTCTACCCTGTGCCTGTTCAC*

FIGURE 16B (Cont.)

AGACTTTGATAGCCAGATCAACGTGCCCAAGACAATGGAGTCCGGCACCTTCATCACAGACAAGTGCGTGCTGGACATGAAGGCTATGG
ACTCTAAGAGCAACGGCGCCATCGCCTGGTCTAATCAGACCAGCTTCACATGCCAGGATATCTTTAAGGAGACCAATGCCACATACCCA
AGCTCCGACGTGCCCTGTGATGCCACCCTGACAGAGAAGAGCTTCGAGACCGACATGAACCTGAATTTTCAGAACCTGCTGGTCATCGT
GCTGAGGATCCTGCTGCTGAAGGTGGCCGGCTTTAATCTGCTGATGACACTGCGCCTGTGGTCTAGCTGATGA

FIGURE 17A

Nucleotide sequence encoding the beta chain of TRBV25-1 + TRAV20 human TCR, with human variable region in larger font, CDR1, CDR2, CDR3 underlined, and human beta constant in italics.

ATGACTATCAGGCTCCTCTGCTACATGGGCTTTTATTTTCTGGGGCAGGCCTCATGGAAGCTGACATCTACCAGAC
CCCAAGATACCTTGTTATAGGGACAGGAAAGAAGATCACTCTGGAATGTTCTCAAACCATGGGCCATGACAAAATGT
ACTGGTATCAACAAGATCCAGGAATGGAACTACACCTCATCCACTATTCCTATGGAGTTAATTCCACAGAGAAGGGA
GATCTTTCCTCTGAGTCAACAGTCTCCAGAATAAGGACGGAGCATTTTCCCCTGACCCTGGAGTCTGCCAGGCCCTC
ACATACCTCTCAGTACCTCTGTGCCAGCAGTCCGCCGGGACAGCCTTACGAGCAGTACTTCGGGCCGGGCACCAGGC
TCACGGTCACA*GAGGACCTGAACAAGGTGTTCCCACCCGAGGTCGCTGTGTTTGAGCCATCAGAAGCAGAGATCTCCCACACCCAAAA*
*GGCCACACTGGTGTGCCTGGCCACAGGCTTCTTCCCCGACCACGTGGAGCTGAGCTGGTGGGTGAATGGGAAGGAGGTGCACAGTGGGG*
*TCAGCACGGACCCGCAGCCCCTCAAGGAGCAGCCCGCCCTCAATGACTCCAGATACTGCCTGAGCAGCCGCCTGAGGGTCTCGGCCACC*
*TTCTGGCAGAACCCCCGCAACCACTTCCGCTGTCAAGTCCAGTTCTACGGGCTCTCGGAGAATGACGAGTGGACCCAGGATAGGGCCAA*
*ACCCGTCACCCAGATCGTCAGCGCCGAGGCCTGGGGTAGAGCAGACTGTGGCTTTACCTCGGTGTCCTACCAGCAAGGGGTCCTGTCTG*
*CCACCATCCTCTATGAGATCCTGCTAGGGAAGGCCACCCTGTATGCTGTGCTGGTCAGCGCCCTTGTGTTGATGGCCATGGTCAAGAGA*
*AAGGATTTC*

FIGURE 17B

Nucleotide sequence encoding the alpha chain of TRBV25-1 + TRAV20 human TCR, with human variable region in larger font, CDR1, CDR2, CDR3 underlined, and human alpha constant in italics ATGGAGAAAATGTTGGAGTGTGCATTCATAGTCTTGTGGCTTCAGCTTGGCTGGTTGAGTGGAGAAGACCAGGTGAC
GCAGAGTCCCGAGGCCCTGAGACTCCAGGAGGGAGAGAGTAGCAGTCTCAACTGCAGTTACACAGTCAGCGGTTTAA
GAGGGCTGTTCTGGTATAGGCAAGATCCTGGGAAAGGCCCTGAATTCCTCTTCACCCTGTATTCAGCTGGGGAAGAA
AAGGAGAAAGAAAGGCTAAAAGCCACATTAACAAAGAAGGAAAGCTTTCTGCACATCACAGCCCCTAAACCTGAAGA
CTCAGCCACTTATCTCTGTGCTGTGCGGATGAACACAGGCTTTCAGAAACTTGTATTTGGAACTGGCACCCGACTTC FIGURE 17B (Cont.)

TGGTCAGTCCA*AATATCCAGAACCCTGACCCTGCCGTGTACCAGCTGAGAGACTCTAAATCCAGTGACAAGTCTGTCTGCCTATTCAC*
*CGATTTTGATTCTCAAACAAATGTGTCACAAAGTAAGGATTCTGATGTGTATATCACAGACAAAACTGTGCTAGACATGAGGTCTATGG*
*ACTTCAAGAGCAACAGTGCTGTGGCCTGGAGCAACAAATCTGACTTTGCATGTGCAAACGCCTTCAACAACAGCATTATTCCAGAAGAC*
*ACCTTCTTCCCCAGCCCAGAAAGTTCCTGTGATGTCAAGCTGGTCGAGAAAAGCTTTGAAACAGATACGAACCTAAACTTTCAAAACCT*
*GTCAGTGATTGGGTTCCGAATCCTCCTCCTGAAAGTGGCCGGGTTTAATCTGCTCATGACGCTGCGGCTGTGGTCCAGCTGATGA*

FIGURE 18A

Codon-optimized nucleotide sequence encoding the beta chain of TRBV25-1 + TRAV20 human TCR, with human variable region in larger font, CDR1, CDR2, CDR3 underlined, and human beta constant in italics ATGACCATCCGGCTGCTGTGCTACATGGGCTTCTATTTTCTGGGCGCCGGCCTGATGGAGGCCGATATCTACCAGAC
CCCCAGATACCTGGTCATCGGCACCGGCAAGAAGATCACACTGGAGTGTTCCCAGACAATGGGCCACGATAAGATGT
ACTGGTATCAGCAGGACCCTGGCATGGAGCTGCACCTGATCCACTACTCCTATGGCGTGAACTCTACCGAGAAGGGC
GACCTGAGCTCCGAGTCCACCGTGTCTCGGATCAGAACAGAGCACTTCCCACTGACCCTGGAGAGCGCCAGGCCTAG
CCACACATCCCAGTACCTGTGCGCCTCTAGCCCACCTGGACAGCCTTACGAGCAGTATTTCGGCCCAGGCACCAGGC
TGACCGTGACA*GAGGACCTGAATAAGGTGTTCCCCCCTGAGGTGGCCGTGTTTGAGCCTTCCGAGGCCGAGATCTCTCACACCCAGAA*
*GGCCACCCTGGTGTGCCTGGCAACCGGCTTCTTTCCAGATCACGTGGAGCTGAGCTGGTGGGTGAACGGCAAGGAGGTGCACAGCGGCG*
*TGTCCACCGACCCACAGCCCCTGAAGGAGCAGCCCGCCCTGAATGATAGCAGATATTGCCTGTCTAGCCGGCTGAGAGTGTCCGCCACC*
*TTTTGGCAGAACCCTCGGAATCACTTCAGATGTCAGGTGCAGTTTTACGGCCTGAGCGAGAATGACGAGTGGACCCAGGATAGGGCCAA*
*GCCCGTGACACAGATCGTGTCCGCCGAGGCATGGGGAAGGGCAGACTGCGGCTTCACATCCGTGTCTTATCAGCAGGGCGTGCTGAGCG*
*CCACCATCCTGTATGAGATCCTGCTGGGCAAGGCCACACTGTACGCCGTGCTGGTGTCCGCCCTGGTGCTGATGGCTATGGTGAAGCGG*
*AAGGACTTT*

FIGURE 18B

Codon-optimized nucleotide sequence encoding the alpha chain of TRBV25-1 + TRAV20 human TCR, with the human variable region in larger font, CDR1, CDR2, CDR3 underlined, and human alpha constant in italics GGTGACCCAGAGCCCAGAGGCCCTGAGGCTGCAGGAGGGAGAGAGCTCCTCTCTGAATTGTAGCTACACAGTGTCCG
GCCTGCGGGGCCTGTTCTGGTATAGACAGGATCCCGGCAAGGGCCCTGAGTTCCTGTTTACCCTGTACTCCGCCGGC
GAGGAGAAGGAGAAGGAGAGACTGAAGGCCACCCTGACAAAGAAGGAGTCTTTTCTGCACATCACAGCCCCAAAGCC
CGAGGACAGCGCCACCTATCTGTGCGCCGTGCGGATGAACACAGGCTTCCAGAAGCTGGTGTTTGGCACCGGCACAA
GACTGCTGGTGAGCCCA*AACATCCAGAATCCCGACCCTGCCGTGTATCAGCTGAGGGACTCCAAGTCCTCTGATAAGAGCGTGTGCC*

FIGURE 18B (Cont.)

TGTTCACCGACTTTGATTCTCAGACAAACGTGAGCCAGTCCAAGGACAGCGACGTGTACATCACCGACAAGACAGTGCTGGATATGCGG
AGCATGGACTTCAAGTCTAACAGCGCCGTGGCCTGGAGCAATAAGTCCGATTTCGCCTGCGCCAATGCCTTTAACAATTCCATCATCCC
TGAGGATACCTTCTTTCCATCTCCCGAGAGCTCCTGTGACGTGAAGCTGGTGGAGAAGTCTTTCGAGACCGATACAAACCTGAATTTTC
AGAACCTGAGCGTGATCGGCTTCCGGATCCTGCTGCTGAAGGTGGCCGGCTTCAATCTGCTGATGACACTGAGACTGTGGTCTAGCTGA
TGA

SEQUENCE LISTING

```
<160> NUMBER OF SEQ ID NOS: 95

<210> SEQ ID NO 1
<211> LENGTH: 5
<212> TYPE: PRT
<213> ORGANISM: Artificial
<220> FEATURE:
<223> OTHER INFORMATION: Synthetic polypeptide

<400> SEQUENCE: 1

Ser Gly Asp Leu Ser
1               5


<210> SEQ ID NO 2
<211> LENGTH: 6
<212> TYPE: PRT
<213> ORGANISM: Artificial
<220> FEATURE:
<223> OTHER INFORMATION: Synthetic polypeptide

<400> SEQUENCE: 2

Tyr Tyr Asn Gly Glu Glu
1               5
```

<210> SEQ ID NO 3
<211> LENGTH: 11
<212> TYPE: PRT
<213> ORGANISM: Artificial
<220> FEATURE:
<223> OTHER INFORMATION: Synthetic polypeptide

<400> SEQUENCE: 3

```
Ala Ser Ser Ala Ala Val His Tyr Gly Tyr Thr
1               5                   10
```

<210> SEQ ID NO 4
<211> LENGTH: 45
<212> TYPE: PRT
<213> ORGANISM: Artificial
<220> FEATURE:
<223> OTHER INFORMATION: Synthetic polypeptide

<400> SEQUENCE: 4

```
Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
            20                  25                  30

Ala Thr Gly Gln Gln Val Thr Leu Arg Cys Ser Pro Arg
        35                  40                  45
```

<210> SEQ ID NO 5
<211> LENGTH: 17
<212> TYPE: PRT
<213> ORGANISM: Artificial
<220> FEATURE:
<223> OTHER INFORMATION: Synthetic polypeptide

<400> SEQUENCE: 5

```
Val Tyr Trp Tyr Gln Gln Ser Leu Asp Gln Gly Leu Gln Phe Leu Ile
1               5                   10                  15

Gln
```

<210> SEQ ID NO 6
<211> LENGTH: 37
<212> TYPE: PRT
<213> ORGANISM: Artificial
<220> FEATURE:
<223> OTHER INFORMATION: Synthetic polypeptide

<400> SEQUENCE: 6

```
Arg Ala Lys Gly Asn Ile Leu Glu Arg Phe Ser Ala Gln Gln Phe Pro
1               5                   10                  15

Asp Leu His Ser Glu Leu Asn Leu Ser Ser Leu Glu Leu Gly Asp Ser
            20                  25                  30

Ala Leu Tyr Phe Cys
        35
```

<210> SEQ ID NO 7
<211> LENGTH: 10
<212> TYPE: PRT
<213> ORGANISM: Artificial
<220> FEATURE:
<223> OTHER INFORMATION: Synthetic polypeptide

<400> SEQUENCE: 7

```
Phe Gly Ser Gly Thr Arg Leu Thr Val Val
1               5                   10
```

```
<210> SEQ ID NO 8
<211> LENGTH: 173
<212> TYPE: PRT
<213> ORGANISM: Artificial
<220> FEATURE:
<223> OTHER INFORMATION: Synthetic polypeptide

<400> SEQUENCE: 8

Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Lys Glu Val His Ser Gly Val Cys Thr Asp Pro Gln Ala Tyr Lys
    50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp Cys Gly
        115                 120                 125

Ile Thr Ser Ala Ser Tyr Gln Gln Gly Val Leu Ser Ala Thr Ile Leu
    130                 135                 140

Tyr Glu Ile Leu Leu Gly Lys Ala Thr Leu Tyr Ala Val Leu Val Ser
145                 150                 155                 160

Thr Leu Val Val Met Ala Met Val Lys Arg Lys Asn Ser
                165                 170


<210> SEQ ID NO 9
<211> LENGTH: 304
<212> TYPE: PRT
<213> ORGANISM: Artificial
<220> FEATURE:
<223> OTHER INFORMATION: Synthetic polypeptide

<400> SEQUENCE: 9

Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
            20                  25                  30

Ala Thr Gly Gln Gln Val Thr Leu Arg Cys Ser Pro Arg Ser Gly Asp
        35                  40                  45

Leu Ser Val Tyr Trp Tyr Gln Gln Ser Leu Asp Gln Gly Leu Gln Phe
    50                  55                  60

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
            100                 105                 110

Ser Ala Ala Val His Tyr Gly Tyr Thr Phe Gly Ser Gly Thr Arg Leu
        115                 120                 125

Thr Val Val Glu Asp Leu Arg Asn Val Thr Pro Pro Lys Val Ser Leu
    130                 135                 140
```

```
Phe Glu Pro Ser Lys Ala Glu Ile Ala Asn Lys Gln Lys Ala Thr Leu
145                 150                 155                 160

Val Cys Leu Ala Arg Gly Phe Phe Pro Asp His Val Glu Leu Ser Trp
                165                 170                 175

Trp Val Asn Gly Lys Glu Val His Ser Gly Val Cys Thr Asp Pro Gln
            180                 185                 190

Ala Tyr Lys Glu Ser Asn Tyr Ser Tyr Cys Leu Ser Ser Arg Leu Arg
        195                 200                 205

Val Ser Ala Thr Phe Trp His Asn Pro Arg Asn His Phe Arg Cys Gln
    210                 215                 220

Val Gln Phe His Gly Leu Ser Glu Glu Asp Lys Trp Pro Glu Gly Ser
225                 230                 235                 240

Pro Lys Pro Val Thr Gln Asn Ile Ser Ala Glu Ala Trp Gly Arg Ala
                245                 250                 255

Asp Cys Gly Ile Thr Ser Ala Ser Tyr Gln Gln Gly Val Leu Ser Ala
            260                 265                 270

Thr Ile Leu Tyr Glu Ile Leu Leu Gly Lys Ala Thr Leu Tyr Ala Val
        275                 280                 285

Leu Val Ser Thr Leu Val Val Met Ala Met Val Lys Arg Lys Asn Ser
    290                 295                 300


<210> SEQ ID NO 10
<211> LENGTH: 7
<212> TYPE: PRT
<213> ORGANISM: Artificial
<220> FEATURE:
<223> OTHER INFORMATION: Synthetic polypeptide

<400> SEQUENCE: 10

Thr Ser Asp Gln Ser Tyr Gly
1               5


<210> SEQ ID NO 11
<211> LENGTH: 8
<212> TYPE: PRT
<213> ORGANISM: Artificial
<220> FEATURE:
<223> OTHER INFORMATION: Synthetic polypeptide

<400> SEQUENCE: 11

Gln Gly Ser Tyr Asp Glu Gln Asn
1               5


<210> SEQ ID NO 12
<211> LENGTH: 11
<212> TYPE: PRT
<213> ORGANISM: Artificial
<220> FEATURE:
<223> OTHER INFORMATION: Synthetic polypeptide

<400> SEQUENCE: 12

Ala Met Arg Glu Gln Gly Ala Gln Lys Leu Val
1               5                   10


<210> SEQ ID NO 13
<211> LENGTH: 46
<212> TYPE: PRT
<213> ORGANISM: Artificial
<220> FEATURE:
<223> OTHER INFORMATION: Synthetic polypeptide

<400> SEQUENCE: 13
```

```
Met Ser Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
            20                  25                  30

Val Gln Glu Lys Glu Ala Val Thr Leu Asp Cys Thr Tyr Asp
        35                  40                  45


<210> SEQ ID NO 14
<211> LENGTH: 17
<212> TYPE: PRT
<213> ORGANISM: Artificial
<220> FEATURE:
<223> OTHER INFORMATION: Synthetic polypeptide

<400> SEQUENCE: 14

Leu Phe Trp Tyr Lys Gln Pro Ser Ser Gly Glu Met Ile Phe Leu Ile
1               5                   10                  15

Tyr


<210> SEQ ID NO 15
<211> LENGTH: 34
<212> TYPE: PRT
<213> ORGANISM: Artificial
<220> FEATURE:
<223> OTHER INFORMATION: Synthetic polypeptide

<400> SEQUENCE: 15

Ala Thr Glu Gly Arg Tyr Ser Leu Asn Phe Gln Lys Ala Arg Lys Ser
1               5                   10                  15

Ala Asn Leu Val Ile Ser Ala Ser Gln Leu Gly Asp Ser Ala Met Tyr
            20                  25                  30

Phe Cys


<210> SEQ ID NO 16
<211> LENGTH: 11
<212> TYPE: PRT
<213> ORGANISM: Artificial
<220> FEATURE:
<223> OTHER INFORMATION: Synthetic polypeptide

<400> SEQUENCE: 16

Phe Gly Gln Gly Thr Arg Leu Thr Ile Asn Pro
1               5                   10


<210> SEQ ID NO 17
<211> LENGTH: 137
<212> TYPE: PRT
<213> ORGANISM: Artificial
<220> FEATURE:
<223> OTHER INFORMATION: Synthetic polypeptide

<400> SEQUENCE: 17

Asn Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
            20                  25                  30

Asn Val Pro Lys Thr Met Glu Ser Gly Thr Phe Ile Thr Asp Lys Cys
        35                  40                  45

Val Leu Asp Met Lys Ala Met Asp Ser Lys Ser Asn Gly Ala Ile Ala
    50                  55                  60

Trp Ser Asn Gln Thr Ser Phe Thr Cys Gln Asp Ile Phe Lys Glu Thr
```

```
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Leu
            100                 105                 110

Val Ile Val Leu Arg Ile Leu Leu Leu Lys Val Ala Gly Phe Asn Leu
        115                 120                 125

Leu Met Thr Leu Arg Leu Trp Ser Ser
    130                 135


<210> SEQ ID NO 18
<211> LENGTH: 271
<212> TYPE: PRT
<213> ORGANISM: Artificial
<220> FEATURE:
<223> OTHER INFORMATION: Synthetic polypeptide

<400> SEQUENCE: 18

Met Ser Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
            20                  25                  30

Val Gln Glu Lys Glu Ala Val Thr Leu Asp Cys Thr Tyr Asp Thr Ser
        35                  40                  45

Asp Gln Ser Tyr Gly Leu Phe Trp Tyr Lys Gln Pro Ser Ser Gly Glu
    50                  55                  60

Met Ile Phe Leu Ile Tyr Gln Gly Ser Tyr Asp Glu Gln Asn Ala Thr
65                  70                  75                  80

Glu Gly Arg Tyr Ser Leu Asn Phe Gln Lys Ala Arg Lys Ser Ala Asn
                85                  90                  95

Leu Val Ile Ser Ala Ser Gln Leu Gly Asp Ser Ala Met Tyr Phe Cys
            100                 105                 110

Ala Met Arg Glu Gln Gly Ala Gln Lys Leu Val Phe Gly Gln Gly Thr
        115                 120                 125

Arg Leu Thr Ile Asn Pro Asn Ile Gln Asn Pro Glu Pro Ala Val Tyr
    130                 135                 140

Gln Leu Lys Asp Pro Arg Ser Gln Asp Ser Thr Leu Cys Leu Phe Thr
145                 150                 155                 160

Asp Phe Asp Ser Gln Ile Asn Val Pro Lys Thr Met Glu Ser Gly Thr
                165                 170                 175

Phe Ile Thr Asp Lys Cys Val Leu Asp Met Lys Ala Met Asp Ser Lys
            180                 185                 190

Ser Asn Gly Ala Ile Ala Trp Ser Asn Gln Thr Ser Phe Thr Cys Gln
        195                 200                 205

Asp Ile Phe Lys Glu Thr Asn Ala Thr Tyr Pro Ser Ser Asp Val Pro
    210                 215                 220

Cys Asp Ala Thr Leu Thr Glu Lys Ser Phe Glu Thr Asp Met Asn Leu
225                 230                 235                 240

Asn Phe Gln Asn Leu Leu Val Ile Val Leu Arg Ile Leu Leu Leu Lys
                245                 250                 255

Val Ala Gly Phe Asn Leu Leu Met Thr Leu Arg Leu Trp Ser Ser
            260                 265                 270


<210> SEQ ID NO 19
<211> LENGTH: 177
<212> TYPE: PRT
```

<213> ORGANISM: Artificial
<220> FEATURE:
<223> OTHER INFORMATION: Synthetic polypeptide

<400> SEQUENCE: 19

```
Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Val Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe
```

<210> SEQ ID NO 20
<211> LENGTH: 309
<212> TYPE: PRT
<213> ORGANISM: Artificial
<220> FEATURE:
<223> OTHER INFORMATION: Synthetic polypeptide

<400> SEQUENCE: 20

```
Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
            20                  25                  30

Ala Thr Gly Gln Gln Val Thr Leu Arg Cys Ser Pro Arg Ser Gly Asp
        35                  40                  45

Leu Ser Val Tyr Trp Tyr Gln Gln Ser Leu Asp Gln Ile Gly Leu Gln
    50                  55                  60

Phe Leu Ile Gln Tyr Tyr Asn Gly Glu Glu Arg Ala Lys Gly Asn Ile
65                  70                  75                  80

Leu Glu Arg Phe Ser Ala Gln Gln Phe Pro Asp Leu His Ser Glu Leu
                85                  90                  95

Asn Leu Ser Ser Leu Glu Leu Gly Asp Ser Ala Leu Tyr Phe Cys Ala
            100                 105                 110

Ser Ser Ala Ala Val His Tyr Gly Tyr Thr Phe Gly Ser Gly Thr Arg
        115                 120                 125

Leu Thr Val Val Glu Asp Leu Asn Lys Val Phe Pro Pro Glu Val Ala
    130                 135                 140

Val Phe Glu Pro Ser Glu Ala Glu Ile Ser His Thr Gln Lys Ala Thr
```

```
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Phe
305
```

<210> SEQ ID NO 21
<211> LENGTH: 142
<212> TYPE: PRT
<213> ORGANISM: Artificial
<220> FEATURE:
<223> OTHER INFORMATION: Synthetic polypeptide

<400> SEQUENCE: 21

```
Asn Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
        35                  40                  45

Val Leu Asp Met Arg Ser Met Asp Phe Lys Ser Asn Ser Ala Ile Val
    50                  55                  60

Ala Trp Ser Asn Lys Ser Asp Phe Ala Cys Ala Asn Ala Phe Asn Asn
65                  70                  75                  80

Ser Ile Ile Pro Glu Asp Thr Phe Phe Pro Ser Pro Glu Ser Ser Cys
                85                  90                  95

Asp Val Lys Leu Val Glu Lys Ser Phe Glu Thr Asp Thr Asn Leu Asn
            100                 105                 110

Phe Gln Asn Leu Ser Val Ile Gly Phe Arg Ile Leu Leu Leu Lys Val
        115                 120                 125

Ala Gly Phe Asn Leu Leu Met Thr Leu Arg Leu Trp Ser Ser
    130                 135                 140
```

<210> SEQ ID NO 22
<211> LENGTH: 276
<212> TYPE: PRT
<213> ORGANISM: Artificial
<220> FEATURE:
<223> OTHER INFORMATION: Synthetic polypeptide

<400> SEQUENCE: 22

```
Met Ser Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
            20                  25                  30

Val Gln Glu Lys Glu Ala Val Thr Leu Asp Cys Thr Tyr Asp Thr Ser
        35                  40                  45

Asp Gln Ser Tyr Gly Leu Phe Trp Tyr Lys Gln Pro Ser Ser Ile Gly
    50                  55                  60

Glu Met Ile Phe Leu Ile Tyr Gln Gly Ser Tyr Asp Glu Gln Asn Ala
65                  70                  75                  80

Thr Glu Gly Arg Tyr Ser Leu Asn Phe Gln Lys Ala Arg Lys Ser Ala
                85                  90                  95

Asn Leu Val Ile Ser Ala Ser Gln Leu Gly Asp Ser Ala Met Tyr Phe
            100                 105                 110

Cys Ala Met Arg Glu Gln Gly Ala Gln Lys Leu Val Phe Gly Gln Gly
        115                 120                 125

Thr Arg Leu Thr Ile Asn Pro Asn Ile Gln Asn Pro Asp Pro Ala Val
    130                 135                 140

Tyr Gln Leu Arg Asp Ser Lys Ser Ser Asp Lys Ser Val Cys Leu Phe
145                 150                 155                 160

Thr Asp Phe Asp Ser Gln Thr Asn Val Ser Gln Ser Lys Asp Ser Asp
                165                 170                 175

Val Tyr Ile Thr Asp Lys Thr Val Leu Asp Met Arg Ser Met Asp Phe
            180                 185                 190

Lys Ser Asn Ser Ala Val Ala Trp Ser Asn Lys Ser Asp Phe Ala Cys
        195                 200                 205

Ala Asn Ala Phe Asn Asn Ser Ile Ile Pro Glu Asp Thr Phe Phe Pro
    210                 215                 220

Ser Pro Glu Ser Ser Cys Asp Val Lys Leu Val Glu Lys Ser Phe Glu
225                 230                 235                 240

Thr Asp Thr Asn Leu Asn Phe Gln Asn Leu Ser Val Ile Gly Phe Arg
                245                 250                 255

Ile Leu Leu Leu Lys Val Ala Gly Phe Asn Leu Leu Met Thr Leu Arg
            260                 265                 270

Leu Trp Ser Ser
        275


<210> SEQ ID NO 23
<211> LENGTH: 5
<212> TYPE: PRT
<213> ORGANISM: Artificial
<220> FEATURE:
<223> OTHER INFORMATION: Synthetic polypeptide

<400> SEQUENCE: 23

Met Gly His Asp Lys
1               5


<210> SEQ ID NO 24
<211> LENGTH: 6
<212> TYPE: PRT
<213> ORGANISM: Artificial
<220> FEATURE:
<223> OTHER INFORMATION: Synthetic polypeptide

<400> SEQUENCE: 24

Ser Tyr Gly Val Asn Ser
1               5
```

<210> SEQ ID NO 25
<211> LENGTH: 12
<212> TYPE: PRT
<213> ORGANISM: Artificial
<220> FEATURE:
<223> OTHER INFORMATION: Synthetic polypeptide

<400> SEQUENCE: 25

```
Ala Ser Ser Pro Pro Gly Gln Pro Tyr Glu Gln Tyr
1               5                   10
```

<210> SEQ ID NO 26
<211> LENGTH: 45
<212> TYPE: PRT
<213> ORGANISM: Artificial
<220> FEATURE:
<223> OTHER INFORMATION: Synthetic polypeptide

<400> SEQUENCE: 26

```
Met Thr Ile Arg Leu Leu Cys Tyr Met Gly Phe Tyr Phe Leu Gly Ala
1               5                   10                  15

Gly Leu Met Glu Ala Asp Ile Tyr Gln Thr Pro Arg Tyr Leu Val Ile
            20                  25                  30

Gly Thr Gly Lys Lys Ile Thr Leu Glu Cys Ser Gln Thr
        35                  40                  45
```

<210> SEQ ID NO 27
<211> LENGTH: 17
<212> TYPE: PRT
<213> ORGANISM: Artificial
<220> FEATURE:
<223> OTHER INFORMATION: Synthetic polypeptide

<400> SEQUENCE: 27

```
Met Tyr Trp Tyr Gln Gln Asp Pro Gly Met Glu Leu His Leu Ile His
1               5                   10                  15

Tyr
```

<210> SEQ ID NO 28
<211> LENGTH: 37
<212> TYPE: PRT
<213> ORGANISM: Artificial
<220> FEATURE:
<223> OTHER INFORMATION: Synthetic polypeptide

<400> SEQUENCE: 28

```
Thr Glu Lys Gly Asp Leu Ser Ser Glu Ser Thr Val Ser Arg Ile Arg
1               5                   10                  15

Thr Glu His Phe Pro Leu Thr Leu Glu Ser Ala Arg Pro Ser His Thr
            20                  25                  30

Ser Gln Tyr Leu Cys
        35
```

<210> SEQ ID NO 29
<211> LENGTH: 10
<212> TYPE: PRT
<213> ORGANISM: Artificial
<220> FEATURE:
<223> OTHER INFORMATION: Synthetic polypeptide

<400> SEQUENCE: 29

```
Phe Gly Pro Gly Thr Arg Leu Thr Val Thr
1               5                   10
```

<210> SEQ ID NO 30
<211> LENGTH: 173
<212> TYPE: PRT
<213> ORGANISM: Artificial
<220> FEATURE:
<223> OTHER INFORMATION: Synthetic polypeptide

<400> SEQUENCE: 30

```
Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Lys Glu Val His Ser Gly Val Cys Thr Asp Pro Gln Ala Tyr Lys
    50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp Cys Gly
        115                 120                 125

Ile Thr Ser Ala Ser Tyr Gln Gln Gly Val Leu Ser Ala Thr Ile Leu
    130                 135                 140

Tyr Glu Ile Leu Leu Gly Lys Ala Thr Leu Tyr Ala Val Leu Val Ser
145                 150                 155                 160

Thr Leu Val Val Met Ala Met Val Lys Arg Lys Asn Ser
                165                 170
```

<210> SEQ ID NO 31
<211> LENGTH: 305
<212> TYPE: PRT
<213> ORGANISM: Artificial
<220> FEATURE:
<223> OTHER INFORMATION: Synthetic polypeptide

<400> SEQUENCE: 31

```
Met Thr Ile Arg Leu Leu Cys Tyr Met Gly Phe Tyr Phe Leu Gly Ala
1               5                   10                  15

Gly Leu Met Glu Ala Asp Ile Tyr Gln Thr Pro Arg Tyr Leu Val Ile
            20                  25                  30

Gly Thr Gly Lys Lys Ile Thr Leu Glu Cys Ser Gln Thr Met Gly His
        35                  40                  45

Asp Lys Met Tyr Trp Tyr Gln Gln Asp Pro Gly Met Glu Leu His Leu
    50                  55                  60

Ile His Tyr Ser Tyr Gly Val Asn Ser Thr Glu Lys Gly Asp Leu Ser
65                  70                  75                  80

Ser Glu Ser Thr Val Ser Arg Ile Arg Thr Glu His Phe Pro Leu Thr
                85                  90                  95

Leu Glu Ser Ala Arg Pro Ser His Thr Ser Gln Tyr Leu Cys Ala Ser
            100                 105                 110

Ser Pro Pro Gly Gln Pro Tyr Glu Gln Tyr Phe Gly Pro Gly Thr Arg
        115                 120                 125

Leu Thr Val Thr Glu Asp Leu Arg Asn Val Thr Pro Pro Lys Val Ser
```

```
    130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175

Trp Trp Val Asn Gly Lys Glu Val His Ser Gly Val Cys Thr Asp Pro
            180                 185                 190

Gln Ala Tyr Lys Glu Ser Asn Tyr Ser Tyr Cys Leu Ser Ser Arg Leu
        195                 200                 205

Arg Val Ser Ala Thr Phe Trp His Asn Pro Arg Asn His Phe Arg Cys
    210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr Gln Gln Gly Val Leu Ser
            260                 265                 270

Ala Thr Ile Leu Tyr Glu Ile Leu Leu Gly Lys Ala Thr Leu Tyr Ala
        275                 280                 285

Val Leu Val Ser Thr Leu Val Val Met Ala Met Val Lys Arg Lys Asn
    290                 295                 300

Ser
305


<210> SEQ ID NO 32
<211> LENGTH: 6
<212> TYPE: PRT
<213> ORGANISM: Artificial
<220> FEATURE:
<223> OTHER INFORMATION: Synthetic polypeptide

<400> SEQUENCE: 32

Val Ser Gly Leu Arg Gly
1               5


<210> SEQ ID NO 33
<211> LENGTH: 7
<212> TYPE: PRT
<213> ORGANISM: Artificial
<220> FEATURE:
<223> OTHER INFORMATION: Synthetic polypeptide

<400> SEQUENCE: 33

Leu Tyr Ser Ala Gly Glu Glu
1               5


<210> SEQ ID NO 34
<211> LENGTH: 12
<212> TYPE: PRT
<213> ORGANISM: Artificial
<220> FEATURE:
<223> OTHER INFORMATION: Synthetic polypeptide

<400> SEQUENCE: 34

Ala Val Arg Met Asn Thr Gly Phe Gln Lys Leu Val
1               5                   10


<210> SEQ ID NO 35
<211> LENGTH: 47
<212> TYPE: PRT
<213> ORGANISM: Artificial
```

```
<220> FEATURE:
<223> OTHER INFORMATION: Synthetic polypeptide

<400> SEQUENCE: 35

Met Glu Lys Met Leu Glu Cys Ala Phe Ile Val Leu Trp Leu Gln Leu
1               5                   10                  15

Gly Trp Leu Ser Gly Glu Asp Gln Val Thr Gln Ser Pro Glu Ala Leu
            20                  25                  30

Arg Leu Gln Glu Gly Glu Ser Ser Ser Leu Asn Cys Ser Tyr Thr
        35                  40                  45


<210> SEQ ID NO 36
<211> LENGTH: 17
<212> TYPE: PRT
<213> ORGANISM: Artificial
<220> FEATURE:
<223> OTHER INFORMATION: Synthetic polypeptide

<400> SEQUENCE: 36

Leu Phe Trp Tyr Arg Gln Asp Pro Gly Lys Gly Pro Glu Phe Leu Phe
1               5                   10                  15

Thr


<210> SEQ ID NO 37
<211> LENGTH: 32
<212> TYPE: PRT
<213> ORGANISM: Artificial
<220> FEATURE:
<223> OTHER INFORMATION: Synthetic polypeptide

<400> SEQUENCE: 37

Lys Glu Lys Glu Arg Leu Lys Ala Thr Leu Thr Lys Lys Glu Ser Phe
1               5                   10                  15

Leu His Ile Thr Ala Pro Lys Pro Glu Asp Ser Ala Thr Tyr Leu Cys
            20                  25                  30


<210> SEQ ID NO 38
<211> LENGTH: 11
<212> TYPE: PRT
<213> ORGANISM: Artificial
<220> FEATURE:
<223> OTHER INFORMATION: Synthetic polypeptide

<400> SEQUENCE: 38

Phe Gly Thr Gly Thr Arg Leu Leu Val Ser Pro
1               5                   10


<210> SEQ ID NO 39
<211> LENGTH: 137
<212> TYPE: PRT
<213> ORGANISM: Artificial
<220> FEATURE:
<223> OTHER INFORMATION: Synthetic polypeptide

<400> SEQUENCE: 39

Asn Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
            20                  25                  30

Asn Val Pro Lys Thr Met Glu Ser Gly Thr Phe Ile Thr Asp Lys Cys
        35                  40                  45

Val Leu Asp Met Lys Ala Met Asp Ser Lys Ser Asn Gly Ala Ile Ala
    50                  55                  60
```

```
Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Leu
            100                 105                 110

Val Ile Val Leu Arg Ile Leu Leu Leu Lys Val Ala Gly Phe Asn Leu
        115                 120                 125

Leu Met Thr Leu Arg Leu Trp Ser Ser
    130                 135


<210> SEQ ID NO 40
<211> LENGTH: 269
<212> TYPE: PRT
<213> ORGANISM: Artificial
<220> FEATURE:
<223> OTHER INFORMATION: Synthetic polypeptide

<400> SEQUENCE: 40

Met Glu Lys Met Leu Glu Cys Ala Phe Ile Val Leu Trp Leu Gln Leu
1               5                   10                  15

Gly Trp Leu Ser Gly Glu Asp Gln Val Thr Gln Ser Pro Glu Ala Leu
            20                  25                  30

Arg Leu Gln Glu Gly Glu Ser Ser Ser Leu Asn Cys Ser Tyr Thr Val
        35                  40                  45

Ser Gly Leu Arg Gly Leu Phe Trp Tyr Arg Gln Asp Pro Gly Lys Gly
    50                  55                  60

Pro Glu Phe Leu Phe Thr Leu Tyr Ser Ala Gly Glu Glu Lys Glu Lys
65                  70                  75                  80

Glu Arg Leu Lys Ala Thr Leu Thr Lys Lys Glu Ser Phe Leu His Ile
                85                  90                  95

Thr Ala Pro Lys Pro Glu Asp Ser Ala Thr Tyr Leu Cys Ala Val Arg
            100                 105                 110

Met Asn Thr Gly Phe Gln Lys Leu Val Phe Gly Thr Gly Thr Arg Leu
        115                 120                 125

Leu Val Ser Pro Asn Ile Gln Asn Pro Glu Pro Ala Val Tyr Gln Leu
    130                 135                 140

Lys Asp Pro Arg Ser Gln Asp Ser Thr Leu Cys Leu Phe Thr Asp Phe
145                 150                 155                 160

Asp Ser Gln Ile Asn Val Pro Lys Thr Met Glu Ser Gly Thr Phe Ile
                165                 170                 175

Thr Asp Lys Cys Val Leu Asp Met Lys Ala Met Asp Ser Lys Ser Asn
            180                 185                 190

Gly Ala Ile Ala Trp Ser Asn Gln Thr Ser Phe Thr Cys Gln Asp Ile
        195                 200                 205

Phe Lys Glu Thr Asn Ala Thr Tyr Pro Ser Ser Asp Val Pro Cys Asp
    210                 215                 220

Ala Thr Leu Thr Glu Lys Ser Phe Glu Thr Asp Met Asn Leu Asn Phe
225                 230                 235                 240

Gln Asn Leu Leu Val Ile Val Leu Arg Ile Leu Leu Leu Lys Val Ala
                245                 250                 255

Gly Phe Asn Leu Leu Met Thr Leu Arg Leu Trp Ser Ser
            260                 265


<210> SEQ ID NO 41
```

```
<211> LENGTH: 177
<212> TYPE: PRT
<213> ORGANISM: Artificial
<220> FEATURE:
<223> OTHER INFORMATION: Synthetic polypeptide

<400> SEQUENCE: 41

Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Val Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe


<210> SEQ ID NO 42
<211> LENGTH: 309
<212> TYPE: PRT
<213> ORGANISM: Artificial
<220> FEATURE:
<223> OTHER INFORMATION: Synthetic polypeptide

<400> SEQUENCE: 42

Met Thr Ile Arg Leu Leu Cys Tyr Met Gly Phe Tyr Phe Leu Gly Ala
1               5                   10                  15

Gly Leu Met Glu Ala Asp Ile Tyr Gln Thr Pro Arg Tyr Leu Val Ile
            20                  25                  30

Gly Thr Gly Lys Lys Ile Thr Leu Glu Cys Ser Gln Thr Met Gly His
        35                  40                  45

Asp Lys Met Tyr Trp Tyr Gln Gln Asp Pro Gly Met Glu Leu His Leu
    50                  55                  60

Ile His Tyr Ser Tyr Gly Val Asn Ser Thr Glu Lys Gly Asp Leu Ser
65                  70                  75                  80

Ser Glu Ser Thr Val Ser Arg Ile Arg Thr Glu His Phe Pro Leu Thr
                85                  90                  95

Leu Glu Ser Ala Arg Pro Ser His Thr Ser Gln Tyr Leu Cys Ala Ser
            100                 105                 110

Ser Pro Pro Gly Gln Pro Tyr Glu Gln Tyr Phe Gly Pro Gly Thr Arg
        115                 120                 125

Leu Thr Val Thr Glu Asp Leu Asn Lys Val Phe Pro Pro Glu Val Ala
    130                 135                 140
```

Val Phe Glu Pro Ser Glu Ala Glu Ile Ser His Thr Gln Lys Ala Thr
145 150 155 160

Leu Val Cys Leu Ala Thr Gly Phe Phe Pro Asp His Val Glu Leu Ser
165 170 175

Trp Trp Val Asn Gly Lys Glu Val His Ser Gly Val Ser Thr Asp Pro
180 185 190

Gln Pro Leu Lys Glu Gln Pro Ala Leu Asn Asp Ser Arg Tyr Cys Leu
195 200 205

Ser Ser Arg Leu Arg Val Ser Ala Thr Phe Trp Gln Asn Pro Arg Asn
210 215 220

His Phe Arg Cys Gln Val Gln Phe Tyr Gly Leu Ser Glu Asn Asp Glu
225 230 235 240

Trp Thr Gln Asp Arg Ala Lys Pro Val Thr Gln Ile Val Ser Ala Glu
245 250 255

Ala Trp Gly Arg Ala Asp Cys Gly Phe Thr Ser Val Ser Tyr Gln Gln
260 265 270

Gly Val Leu Ser Ala Thr Ile Leu Tyr Glu Ile Leu Leu Gly Lys Ala
275 280 285

Thr Leu Tyr Ala Val Leu Val Ser Ala Leu Val Leu Met Ala Met Val
290 295 300

Lys Arg Lys Asp Phe
305

<210> SEQ ID NO 43
<211> LENGTH: 141
<212> TYPE: PRT
<213> ORGANISM: Artificial
<220> FEATURE:
<223> OTHER INFORMATION: Synthetic polypeptide

<400> SEQUENCE: 43

Asn Ile Gln Asn Pro Asp Pro Ala Val Tyr Gln Leu Arg Asp Ser Lys
1 5 10 15

Ser Ser Asp Lys Ser Val Cys Leu Phe Thr Asp Phe Asp Ser Gln Thr
20 25 30

Asn Val Ser Gln Ser Lys Asp Ser Asp Val Tyr Ile Thr Asp Lys Thr
35 40 45

Val Leu Asp Met Arg Ser Met Asp Phe Lys Ser Asn Ser Ala Val Ala
50 55 60

Trp Ser Asn Lys Ser Asp Phe Ala Cys Ala Asn Ala Phe Asn Asn Ser
65 70 75 80

Ile Ile Pro Glu Asp Thr Phe Phe Pro Ser Pro Glu Ser Ser Cys Asp
85 90 95

Val Lys Leu Val Glu Lys Ser Phe Glu Thr Asp Thr Asn Leu Asn Phe
100 105 110

Gln Asn Leu Ser Val Ile Gly Phe Arg Ile Leu Leu Leu Lys Val Ala
115 120 125

Gly Phe Asn Leu Leu Met Thr Leu Arg Leu Trp Ser Ser
130 135 140

<210> SEQ ID NO 44
<211> LENGTH: 273
<212> TYPE: PRT
<213> ORGANISM: Artificial
<220> FEATURE:
<223> OTHER INFORMATION: Synthetic polypeptide

<400> SEQUENCE: 44

```
Met Glu Lys Met Leu Glu Cys Ala Phe Ile Val Leu Trp Leu Gln Leu
1               5                   10                  15

Gly Trp Leu Ser Gly Glu Asp Gln Val Thr Gln Ser Pro Glu Ala Leu
            20                  25                  30

Arg Leu Gln Glu Gly Glu Ser Ser Ser Leu Asn Cys Ser Tyr Thr Val
        35                  40                  45

Ser Gly Leu Arg Gly Leu Phe Trp Tyr Arg Gln Asp Pro Gly Lys Gly
    50                  55                  60

Pro Glu Phe Leu Phe Thr Leu Tyr Ser Ala Gly Glu Glu Lys Glu Lys
65                  70                  75                  80

Glu Arg Leu Lys Ala Thr Leu Thr Lys Lys Glu Ser Phe Leu His Ile
                85                  90                  95

Thr Ala Pro Lys Pro Glu Asp Ser Ala Thr Tyr Leu Cys Ala Val Arg
            100                 105                 110

Met Asn Thr Gly Phe Gln Lys Leu Val Phe Gly Thr Gly Thr Arg Leu
        115                 120                 125

Leu Val Ser Pro Asn Ile Gln Asn Pro Asp Pro Ala Val Tyr Gln Leu
    130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
        195                 200                 205

Phe Asn Asn Ser Ile Ile Pro Glu Asp Thr Phe Phe Pro Ser Pro Glu
    210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
            260                 265                 270

Ser
```

<210> SEQ ID NO 45
<211> LENGTH: 134
<212> TYPE: PRT
<213> ORGANISM: Artificial
<220> FEATURE:
<223> OTHER INFORMATION: Synthetic polypeptide

<400> SEQUENCE: 45

```
Met Ser Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
            20                  25                  30

Val Gln Glu Lys Glu Ala Val Thr Leu Asp Cys Thr Tyr Asp Thr Ser
        35                  40                  45

Asp Gln Ser Tyr Gly Leu Phe Trp Tyr Lys Gln Pro Ser Ser Gly Glu
    50                  55                  60

Met Ile Phe Leu Ile Tyr Gln Gly Ser Tyr Asp Glu Gln Asn Ala Thr
65                  70                  75                  80
```

```
Glu Gly Arg Tyr Ser Leu Asn Phe Gln Lys Ala Arg Lys Ser Ala Asn
                85                  90                  95

Leu Val Ile Ser Ala Ser Gln Leu Gly Asp Ser Ala Met Tyr Phe Cys
            100                 105                 110

Ala Met Arg Glu Gln Gly Ala Gln Lys Leu Val Phe Gly Gln Gly Thr
        115                 120                 125

Arg Leu Thr Ile Asn Pro
    130


<210> SEQ ID NO 46
<211> LENGTH: 132
<212> TYPE: PRT
<213> ORGANISM: Artificial
<220> FEATURE:
<223> OTHER INFORMATION: Synthetic polypeptide

<400> SEQUENCE: 46

Met Glu Lys Met Leu Glu Cys Ala Phe Ile Val Leu Trp Leu Gln Leu
1               5                   10                  15

Gly Trp Leu Ser Gly Glu Asp Gln Val Thr Gln Ser Pro Glu Ala Leu
            20                  25                  30

Arg Leu Gln Glu Gly Glu Ser Ser Ser Leu Asn Cys Ser Tyr Thr Val
        35                  40                  45

Ser Gly Leu Arg Gly Leu Phe Trp Tyr Arg Gln Asp Pro Gly Lys Gly
    50                  55                  60

Pro Glu Phe Leu Phe Thr Leu Tyr Ser Ala Gly Glu Glu Lys Glu Lys
65                  70                  75                  80

Glu Arg Leu Lys Ala Thr Leu Thr Lys Lys Glu Ser Phe Leu His Ile
                85                  90                  95

Thr Ala Pro Lys Pro Glu Asp Ser Ala Thr Tyr Leu Cys Ala Val Arg
            100                 105                 110

Met Asn Thr Gly Phe Gln Lys Leu Val Phe Gly Thr Gly Thr Arg Leu
        115                 120                 125

Leu Val Ser Pro
    130


<210> SEQ ID NO 47
<211> LENGTH: 131
<212> TYPE: PRT
<213> ORGANISM: Artificial
<220> FEATURE:
<223> OTHER INFORMATION: Synthetic polypeptide

<400> SEQUENCE: 47

Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
            20                  25                  30

Ala Thr Gly Gln Gln Val Thr Leu Arg Cys Ser Pro Arg Ser Gly Asp
        35                  40                  45

Leu Ser Val Tyr Trp Tyr Gln Gln Ser Leu Asp Gln Gly Leu Gln Phe
    50                  55                  60

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
```

```
            100                 105                 110

Ser Ala Ala Val His Tyr Gly Tyr Thr Phe Gly Ser Gly Thr Arg Leu
        115                 120                 125

Thr Val Val
    130


<210> SEQ ID NO 48
<211> LENGTH: 132
<212> TYPE: PRT
<213> ORGANISM: Artificial
<220> FEATURE:
<223> OTHER INFORMATION: Synthetic polypeptide

<400> SEQUENCE: 48

Met Thr Ile Arg Leu Leu Cys Tyr Met Gly Phe Tyr Phe Leu Gly Ala
1               5                   10                  15

Gly Leu Met Glu Ala Asp Ile Tyr Gln Thr Pro Arg Tyr Leu Val Ile
            20                  25                  30

Gly Thr Gly Lys Lys Ile Thr Leu Glu Cys Ser Gln Thr Met Gly His
        35                  40                  45

Asp Lys Met Tyr Trp Tyr Gln Gln Asp Pro Gly Met Glu Leu His Leu
    50                  55                  60

Ile His Tyr Ser Tyr Gly Val Asn Ser Thr Glu Lys Gly Asp Leu Ser
65                  70                  75                  80

Ser Glu Ser Thr Val Ser Arg Ile Arg Thr Glu His Phe Pro Leu Thr
                85                  90                  95

Leu Glu Ser Ala Arg Pro Ser His Thr Ser Gln Tyr Leu Cys Ala Ser
            100                 105                 110

Ser Pro Pro Gly Gln Pro Tyr Glu Gln Tyr Phe Gly Pro Gly Thr Arg
        115                 120                 125

Leu Thr Val Thr
    130


<210> SEQ ID NO 49
<211> LENGTH: 1812
<212> TYPE: DNA
<213> ORGANISM: Artificial
<220> FEATURE:
<223> OTHER INFORMATION: Synthetic oligonucleotide

<400> SEQUENCE: 49

atgggcttca ggctcctctg ctgtgtggcc ttttgtctcc tgggagcagg cccagtggat      60

tctggagtca cacaaacccc aaagcacctg atcacagcaa ctggacagca agtgacgctg     120

agatgctccc ctaggtctgg agacctctct gtgtactggt accaacagag cctggaccag     180

ggcctccagt tcctcattca gtattataat ggagaagaga gagcaaaagg aaacattctt     240

gaacgattct ccgcacaaca gttccctgac ttgcactctg aactaaacct gagctctctg     300

gagctggggg actcagcttt gtatttctgt gccagcagcg cggcagttca ctatggctac     360

accttcggtt cggggaccag gttaaccgtt gtagaggacc tgagaaacgt gacaccccct     420

aaggtgagcc tgttcgagcc ctccaaggcc gagatcgcca ataagcagaa ggccaccctg     480

gtgtgcctgg caaggggctt ctttcctgat cacgtggagc tgtcttggtg ggtgaacggc     540

aaggaggtgc acagcggcgt gtgcaccgac ccacaggcct ataaggagag caattattcc     600

tactgtctgt ctagccggct gagagtgagc gccacatttt ggcacaaccc tcggaatcac     660

ttcagatgcc aggtgcagtt tcacggcctg tctgaggagg ataagtggcc agagggcagc     720
```

```
ccaaagccag tgacccagaa catctccgcc gaggcatggg gaagagcaga ctgtggcatc    780

accagcgcct cctaccagca gggcgtgctg tccgccacaa tcctgtatga gatcctgctg    840

ggcaaggcca ccctgtacgc cgtgctggtg agcacactgg tggtcatggc tatggtgaag    900

aggaagaact ccagggcaaa gcggagcgga agcggagcca caaatttctc tctgctgaag    960

caggcaggcg atgtggagga gaaccctgga ccaatgtcac tttctagcct gctgaaggtg   1020

gtcacagctt cactgtggct aggacctggc attgcccaga agataactca aacccaacca   1080

ggaatgttcg tgcaggaaaa ggaggctgtg actctggact gcacatatga caccagtgat   1140

caaagttatg gtctcttctg gtacaagcag cccagcagtg ggaaaatgat tttccttatt   1200

tatcaggggt cttatgacga gcaaaatgca acagaaggtc gctactcatt gaatttccag   1260

aaggcaagaa aatccgccaa ccttgtcatc tccgcttcac aactgggga ctcagcaatg   1320

tatttctgtg caatgagaga gcagggagcc cagaagctgg tatttggcca aggaaccagg   1380

ctgactatca acccaaacat ccagaatcca gagcccgccg tgtatcagct gaaggaccca   1440

agatcccagg attctaccct gtgcctgttc acagactttg attctcagat caatgtgccc   1500

aagacaatgg agagcggcac cttcatcaca gacaagtgcg tgctggatat gaaggctatg   1560

gactccaagt ctaacggcgc catcgcctgg agcaatcaga cctccttcac atgccaggat   1620

atctttaagg agacaaacgc cacataccct tctagcgacg tgccatgtga tgccaccctg   1680

acagagaaga gcttcgagac agacatgaac ctgaattttc agaatctgct ggtcatcgtg   1740

ctgcggatcc tgctgctgaa ggtggctggg tttaatctgc tgatgacact gcgactgtgg   1800

agtagctgat ga                                                       1812
```

```
<210> SEQ ID NO 50
<211> LENGTH: 602
<212> TYPE: PRT
<213> ORGANISM: Artificial
<220> FEATURE:
<223> OTHER INFORMATION: Synthetic polypeptide

<400> SEQUENCE: 50

Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
            20                  25                  30

Ala Thr Gly Gln Gln Val Thr Leu Arg Cys Ser Pro Arg Ser Gly Asp
        35                  40                  45

Leu Ser Val Tyr Trp Tyr Gln Gln Ser Leu Asp Gln Gly Leu Gln Phe
    50                  55                  60

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
            100                 105                 110

Ser Ala Ala Val His Tyr Gly Tyr Thr Phe Gly Ser Gly Thr Arg Leu
        115                 120                 125

Thr Val Val Glu Asp Leu Arg Asn Val Thr Pro Pro Lys Val Ser Leu
    130                 135                 140

Phe Glu Pro Ser Lys Ala Glu Ile Ala Asn Lys Gln Lys Ala Thr Leu
145                 150                 155                 160

Val Cys Leu Ala Arg Gly Phe Phe Pro Asp His Val Glu Leu Ser Trp
```

```
                165                 170                 175

Trp Val Asn Gly Lys Glu Val His Ser Gly Val Cys Thr Asp Pro Gln
            180                 185                 190

Ala Tyr Lys Glu Ser Asn Tyr Ser Tyr Cys Leu Ser Ser Arg Leu Arg
        195                 200                 205

Val Ser Ala Thr Phe Trp His Asn Pro Arg Asn His Phe Arg Cys Gln
    210                 215                 220

Val Gln Phe His Gly Leu Ser Glu Glu Asp Lys Trp Pro Glu Gly Ser
225                 230                 235                 240

Pro Lys Pro Val Thr Gln Asn Ile Ser Ala Glu Ala Trp Gly Arg Ala
                245                 250                 255

Asp Cys Gly Ile Thr Ser Ala Ser Tyr Gln Gln Gly Val Leu Ser Ala
            260                 265                 270

Thr Ile Leu Tyr Glu Ile Leu Leu Gly Lys Ala Thr Leu Tyr Ala Val
        275                 280                 285

Leu Val Ser Thr Leu Val Val Met Ala Met Val Lys Arg Lys Asn Ser
    290                 295                 300

Arg Ala Lys Arg Ser Gly Ser Gly Ala Thr Asn Phe Ser Leu Leu Lys
305                 310                 315                 320

Gln Ala Gly Asp Val Glu Glu Asn Pro Gly Pro Met Ser Leu Ser Ser
                325                 330                 335

Leu Leu Lys Val Val Thr Ala Ser Leu Trp Leu Gly Pro Gly Ile Ala
            340                 345                 350

Gln Lys Ile Thr Gln Thr Gln Pro Gly Met Phe Val Gln Glu Lys Glu
        355                 360                 365

Ala Val Thr Leu Asp Cys Thr Tyr Asp Thr Ser Asp Gln Ser Tyr Gly
    370                 375                 380

Leu Phe Trp Tyr Lys Gln Pro Ser Ser Gly Glu Met Ile Phe Leu Ile
385                 390                 395                 400

Tyr Gln Gly Ser Tyr Asp Glu Gln Asn Ala Thr Glu Gly Arg Tyr Ser
                405                 410                 415

Leu Asn Phe Gln Lys Ala Arg Lys Ser Ala Asn Leu Val Ile Ser Ala
            420                 425                 430

Ser Gln Leu Gly Asp Ser Ala Met Tyr Phe Cys Ala Met Arg Glu Gln
        435                 440                 445

Gly Ala Gln Lys Leu Val Phe Gly Gln Gly Thr Arg Leu Thr Ile Asn
    450                 455                 460

Pro Asn Ile Gln Asn Pro Glu Pro Ala Val Tyr Gln Leu Lys Asp Pro
465                 470                 475                 480

Arg Ser Gln Asp Ser Thr Leu Cys Leu Phe Thr Asp Phe Asp Ser Gln
                485                 490                 495

Ile Asn Val Pro Lys Thr Met Glu Ser Gly Thr Phe Ile Thr Asp Lys
            500                 505                 510

Cys Val Leu Asp Met Lys Ala Met Asp Ser Lys Ser Asn Gly Ala Ile
        515                 520                 525

Ala Trp Ser Asn Gln Thr Ser Phe Thr Cys Gln Asp Ile Phe Lys Glu
    530                 535                 540

Thr Asn Ala Thr Tyr Pro Ser Ser Asp Val Pro Cys Asp Ala Thr Leu
545                 550                 555                 560

Thr Glu Lys Ser Phe Glu Thr Asp Met Asn Leu Asn Phe Gln Asn Leu
                565                 570                 575

Leu Val Ile Val Leu Arg Ile Leu Leu Leu Lys Val Ala Gly Phe Asn
            580                 585                 590
```

```
Leu Leu Met Thr Leu Arg Leu Trp Ser Ser
        595                 600


<210> SEQ ID NO 51
<211> LENGTH: 1812
<212> TYPE: DNA
<213> ORGANISM: Artificial
<220> FEATURE:
<223> OTHER INFORMATION: Synthetic oligonucleotide

<400> SEQUENCE: 51

atgggcttcc ggctgctgtg ctgcgtggca ttttgcctgc tgggagcagg acctgtggat     60

agcggcgtga cccagacacc aaagcacctg atcaccgcaa caggacagca ggtgaccctg    120

aggtgttccc caagatctgg cgatctgtcc gtgtactggt atcagcagtc tctggaccag    180

ggcctgcagt tcctgatcca gtactataac ggcgaggagc gggccaaggg caatatcctg    240

gagagattca gcgcccagca gtttcctgat ctgcactccg agctgaatct gagctccctg    300

gagctgggcg actccgccct gtacttctgc gcctctagcg ccgcagtgca ctacggctat    360

acctttggct ctggcaccag gctgacagtg gtggaggacc tgcgcaatgt gacacccccct    420

aaggtgtctc tgttcgagcc cagcaaggcc gagatcgcca acaagcagaa ggccaccctg    480

gtgtgcctgg cccggggctt ctttcctgat cacgtggagc tgtcctggtg ggtgaatggc    540

aaggaggtgc actctggcgt gtgcaccgac ccacaggcct acaaggagag caactactcc    600

tattgtctgt cctctcggct gagagtgagc gccacatttt ggcacaaccc taggaatcac    660

ttccgctgcc aggtgcagtt tcacggcctg tctgaggagg ataagtggcc agagggaagc    720

ccaaagccag tgacccagaa tatctccgcc gaggcatggg gaagggcaga ctgtggaatc    780

acctctgcca gctatcagca gggcgtgctg tccgccacaa tcctgtacga gatcctgctg    840

ggcaaggcca ccctgtatgc cgtgctggtg tccacactgg tggtcatggc tatggtgaag    900

aggaagaaca gccgggccaa gcggagcgga tctggagcca ccaacttcag cctgctgaag    960

caggcaggcg atgtggagga gaaccctgga ccaatgtctc tgagctccct gctgaaggtc   1020

gtgacagcaa gcctgtggct gggaccagga atcgcacaga agatcaccca gacacagcct   1080

ggcatgtttg tgcaggagaa ggaggccgtg accctggact gcacctacga cacatctgat   1140

cagagctacg gcctgttctg gtataagcag ccatctagcg gcgagatgat ctttctgatc   1200

taccagggca gctatgatga gcagaacgcc acagagggcc ggtactctct gaatttccag   1260

aaggccagaa agagcgccaa cctggtcatc agcgcctccc agctgggcga ctccgccatg   1320

tatttctgtg ccatgaggga gcagggcgcc cagaagctgg tgtttggcca gggcacccgc   1380

ctgacaatca acccaaatat ccagaatccc gagcctgccg tgtaccagct gaaggacccc   1440

agatcccagg attctaccct gtgcctgttc acagactttg atagccagat caacgtgccc   1500

aagacaatgg agtccggcac cttcatcaca gacaagtgcg tgctggacat gaaggctatg   1560

gactctaaga gcaacggcgc catcgcctgg agcaatcaga cctccttcac atgccaggat   1620

atctttaagg agaccaacgc cacatatcca tcctctgacg tgccctgtga tgccaccctg   1680

acagagaagt ccttcgagac cgacatgaac ctgaattttc agaatctgct ggtcatcgtg   1740

ctgcggatcc tgctgctgaa ggtggccggc tttaacctgc tgatgacact gagactgtgg   1800

agctcctgat ga                                                       1812


<210> SEQ ID NO 52
<211> LENGTH: 1836
```

<212> TYPE: DNA
<213> ORGANISM: Homo sapiens

<400> SEQUENCE: 52
atgggcttca ggctcctctg ctgtgtggcc ttttgtctcc tgggagcagg cccagtggat 60
tctggagtca cacaaacccc aaagcacctg atcacagcaa ctggacagca agtgacgctg 120
agatgctccc ctaggtctgg agacctctct gtgtactggt accaacagag cctggaccag 180
ggcctccagt tcctcattca gtattataat ggagaagaga gagcaaaagg aaacattctt 240
gaacgattct ccgcacaaca gttccctgac ttgcactctg aactaaacct gagctctctg 300
gagctggggg actcagcttt gtatttctgt gccagcagcg cggcagttca ctatggctac 360
accttcggtt cggggaccag gttaaccgtt gtagaggacc tgaacaaggt gttcccaccc 420
gaggtcgctg tgtttgagcc atcagaagca gagatctccc acacccaaaa ggccacactg 480
gtgtgcctgg ccacaggctt cttccccgac cacgtggagc tgagctggtg ggtgaatggg 540
aaggaggtgc acagtggggt cagcacggac ccgcagcccc tcaaggagca gcccgccctc 600
aatgactcca gatactgcct gagcagccgc ctgagggtct cggccacctt ctggcagaac 660
ccccgcaacc acttccgctg tcaagtccag ttctacgggc tctcggagaa tgacgagtgg 720
acccaggata gggccaaacc cgtcacccag atcgtcagcg ccgaggcctg gggtagagca 780
gactgtggct ttacctcggt gtcctaccag caaggggtcc tgtctgccac catcctctat 840
gagatcctgc tagggaaggc caccctgtat gctgtgctgg tcagcgccct tgtgttgatg 900
gccatggtca agagaaagga tttcagggca aagcggagcg gaagcggagc cacaaatttc 960
tctctgctga agcaggcagg cgatgtggag gagaaccctg gaccaatgtc actttctagc 1020
ctgctgaagg tggtcacagc ttcactgtgg ctaggacctg gcattgccca gaagataact 1080
caaacccaac caggaatgtt cgtgcaggaa aaggaggctg tgactctgga ctgcacatat 1140
gacaccagtg atcaaagtta tggtctcttc tggtacaagc agcccagcag tggggaaatg 1200
atttttctta tttatcaggg gtcttatgac gagcaaaatg caacagaagg tcgctactca 1260
ttgaatttcc agaaggcaag aaaatccgcc aaccttgtca tctccgcttc acaactgggg 1320
gactcagcaa tgtatttctg tgcaatgaga gagcagggag cccagaagct ggtatttggc 1380
caaggaacca ggctgactat caacccaaat atccagaacc ctgaccctgc cgtgtaccag 1440
ctgagagact ctaaatccag tgacaagtct gtctgcctat tcaccgattt tgattctcaa 1500
acaaatgtgt cacaaagtaa ggattctgat gtgtatatca cagacaaaac tgtgctagac 1560
atgaggtcta tggacttcaa gagcaacagt gctgtggcct ggagcaacaa atctgacttt 1620
gcatgtgcaa acgccttcaa caacagcatt attccagaag acaccttctt ccccagccca 1680
gaaagttcct gtgatgtcaa gctggtcgag aaaagctttg aaacagatac gaacctaaac 1740
tttcaaaacc tgtcagtgat tgggttccga atcctcctcc tgaaagtggc cgggtttaat 1800
ctgctcatga cgctgcggct gtggtccagc tgatga 1836

<210> SEQ ID NO 53
<211> LENGTH: 610
<212> TYPE: PRT
<213> ORGANISM: Homo sapiens

<400> SEQUENCE: 53

Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr

```
            20                  25                  30

Ala Thr Gly Gln Gln Val Thr Leu Arg Cys Ser Pro Arg Ser Gly Asp
        35                  40                  45

Leu Ser Val Tyr Trp Tyr Gln Gln Ser Leu Asp Gln Gly Leu Gln Phe
    50                  55                  60

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
            100                 105                 110

Ser Ala Ala Val His Tyr Gly Tyr Thr Phe Gly Ser Gly Thr Arg Leu
        115                 120                 125

Thr Val Val Glu Asp Leu Asn Lys Val Phe Pro Pro Glu Val Ala Val
    130                 135                 140

Phe Glu Pro Ser Glu Ala Glu Ile Ser His Thr Gln Lys Ala Thr Leu
145                 150                 155                 160

Val Cys Leu Ala Thr Gly Phe Phe Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Val Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
    290                 295                 300

Arg Lys Asp Phe Arg Ala Lys Arg Ser Gly Ser Gly Ala Thr Asn Phe
305                 310                 315                 320

Ser Leu Leu Lys Gln Ala Gly Asp Val Glu Glu Asn Pro Gly Pro Met
                325                 330                 335

Ser Leu Ser Ser Leu Leu Lys Val Val Thr Ala Ser Leu Trp Leu Gly
            340                 345                 350

Pro Gly Ile Ala Gln Lys Ile Thr Gln Thr Gln Pro Gly Met Phe Val
        355                 360                 365

Gln Glu Lys Glu Ala Val Thr Leu Asp Cys Thr Tyr Asp Thr Ser Asp
    370                 375                 380

Gln Ser Tyr Gly Leu Phe Trp Tyr Lys Gln Pro Ser Ser Gly Glu Met
385                 390                 395                 400

Ile Phe Leu Ile Tyr Gln Gly Ser Tyr Asp Glu Gln Asn Ala Thr Glu
                405                 410                 415

Gly Arg Tyr Ser Leu Asn Phe Gln Lys Ala Arg Lys Ser Ala Asn Leu
            420                 425                 430

Val Ile Ser Ala Ser Gln Leu Gly Asp Ser Ala Met Tyr Phe Cys Ala
        435                 440                 445
```

```
Met Arg Glu Gln Gly Ala Gln Lys Leu Val Phe Gly Gln Gly Thr Arg
    450                 455                 460

Leu Thr Ile Asn Pro Asn Ile Gln Asn Pro Asp Pro Ala Val Tyr Gln
465                 470                 475                 480

Leu Arg Asp Ser Lys Ser Ser Asp Lys Ser Val Cys Leu Phe Thr Asp
                485                 490                 495

Phe Asp Ser Gln Thr Asn Val Ser Gln Ser Lys Asp Ser Asp Val Tyr
            500                 505                 510

Ile Thr Asp Lys Thr Val Leu Asp Met Arg Ser Met Asp Phe Lys Ser
        515                 520                 525

Asn Ser Ala Val Ala Trp Ser Asn Lys Ser Asp Phe Ala Cys Ala Asn
    530                 535                 540

Ala Phe Asn Asn Ser Ile Ile Pro Glu Asp Thr Phe Phe Pro Ser Pro
545                 550                 555                 560

Glu Ser Ser Cys Asp Val Lys Leu Val Glu Lys Ser Phe Glu Thr Asp
                565                 570                 575

Thr Asn Leu Asn Phe Gln Asn Leu Ser Val Ile Gly Phe Arg Ile Leu
            580                 585                 590

Leu Leu Lys Val Ala Gly Phe Asn Leu Leu Met Thr Leu Arg Leu Trp
        595                 600                 605

Ser Ser
    610
```

<210> SEQ ID NO 54
<211> LENGTH: 1836
<212> TYPE: DNA
<213> ORGANISM: Artificial
<220> FEATURE:
<223> OTHER INFORMATION: Synthetic oligonucleotide

<400> SEQUENCE: 54

```
atgggcttcc ggctgctgtg ctgcgtggca ttttgcctgc tgggagcagg acctgtggat     60

agcggcgtga cccagacacc aaagcacctg atcaccgcaa caggacagca ggtgaccctg    120

aggtgttccc caagatctgg cgatctgtcc gtgtactggt atcagcagtc tctggaccag    180

ggcctgcagt tcctgatcca gtactataac ggcgaggagc gggccaaggg caatatcctg    240

gagagattca gcgcccagca gtttcctgat ctgcactccg agctgaatct gagctccctg    300

gagctgggcg actccgccct gtacttctgc gcctctagcg ccgcagtgca ctacggctat    360

acctttggct ctggcaccag gctgacagtg gtggaggacc tgaataaggt gttccccccct   420

gaggtggccg tgtttgagcc ttccgaggcc gagatctctc acacccagaa ggccaccctg    480

gtgtgcctgg caaccggctt ctttccagat cacgtggagc tgagctggtg ggtgaacggc    540

aaggaggtgc acagcggcgt gtccaccgac ccacagcccc tgaaggagca gcccgccctg    600

aatgatagca gatattgcct gtctagccgg ctgagagtgt ccgccacctt ttggcagaac    660

cctcggaatc acttcagatg tcaggtgcag ttttacggcc tgagcgagaa tgacgagtgg    720

acccaggata gggccaagcc cgtgacacag atcgtgtccg ccgaggcatg gggaagggca    780

gactgcggct tcacatccgt gtcttatcag cagggcgtgc tgagcgccac catcctgtat    840

gagatcctgc tgggcaaggc cacactgtac gccgtgctgg tgtccgccct ggtgctgatg    900

gctatggtga agcggaagga ctttcgggcc aagcggagcg gatctggagc caccaacttc    960

agcctgctga agcaggcagg cgatgtggag gagaaccctg gaccaatgtc tctgagctcc   1020

ctgctgaagg tcgtgacagc aagcctgtgg ctgggaccag gaatcgcaca gaagatcacc   1080
```

cagacacagc ctggcatgtt tgtgcaggag aaggaggccg tgaccctgga ctgcacctac 1140
gacacatctg atcagagcta cggcctgttc tggtataagc agccatctag cggcgagatg 1200
atctttctga tctaccaggg cagctatgat gagcagaacg ccacagaggg ccggtactct 1260
ctgaatttcc agaaggccag aaagagcgcc aacctggtca tcagcgcctc ccagctgggc 1320
gactccgcca tgtatttctg tgccatgagg gagcagggcg cccagaagct ggtgtttggc 1380
cagggcaccc gcctgacaat caacccaaac atccagaatc ccgaccctgc cgtgtatcag 1440
ctgagggact ccaagtcctc tgataagagc gtgtgcctgt tcaccgactt tgattctcag 1500
acaaacgtga gccagtccaa ggacagcgac gtgtacatca ccgacaagac agtgctggat 1560
atgcggagca tggacttcaa gtctaacagc gccgtggcct ggagcaataa gtccgatttc 1620
gcctgcgcca atgcctttaa caattccatc atccctgagg ataccttctt tccatctccc 1680
gagagctcct gtgacgtgaa gctggtggag aagtctttcg agaccgatac aaacctgaat 1740
tttcagaacc tgagcgtgat cggcttccgg atcctgctgc tgaaggtggc cggcttcaat 1800
ctgctgatga cactgagact gtggtctagc tgatga 1836

<210> SEQ ID NO 55
<211> LENGTH: 1809
<212> TYPE: DNA
<213> ORGANISM: Artificial
<220> FEATURE:
<223> OTHER INFORMATION: Synthetic oligonucleotide

<400> SEQUENCE: 55
atgactatca ggctcctctg ctacatgggc ttttattttc tgggggcagg cctcatggaa 60
gctgacatct accagacccc aagatacctt gttataggga caggaaagaa gatcactctg 120
gaatgttctc aaaccatggg ccatgacaaa atgtactggt atcaacaaga tccaggaatg 180
gaactacacc tcatccacta ttcctatgga gttaattcca cagagaaggg agatctttcc 240
tctgagtcaa cagtctccag aataaggacg gagcattttc ccctgaccct ggagtctgcc 300
aggccctcac atacctctca gtacctctgt gccagcagtc cgccgggaca gccttacgag 360
cagtacttcg ggccgggcac caggctcacg gtcacagagg acctgagaaa cgtgacaccc 420
cctaaggtga gcctgttcga gccctccaag gccgagatcg ccaataagca gaaggccacc 480
ctggtgtgcc tggcaagggg cttctttcct gatcacgtgg agctgtcttg gtgggtgaac 540
ggcaaggagg tgcacagcgg cgtgtgcacc gacccacagg cctataagga gagcaattat 600
tcctactgtc tgtctagccg gctgagagtg agcgccacat tttggcacaa ccctcggaat 660
cacttcagat gccaggtgca gtttcacggc ctgtctgagg aggataagtg gccagagggc 720
agcccaaagc cagtgaccca gaacatctcc gccgaggcat ggggaagagc agactgtggc 780
atcaccagcg cctcctacca gcagggcgtg ctgtccgcca caatcctgta tgagatcctg 840
ctgggcaagg ccaccctgta cgccgtgctg gtgagcacac tggtggtcat ggctatggtg 900
aagaggaaga actccagggc aaagcggagc ggaagcggag ccacaaattt ctctctgctg 960
aagcaggcag gcgatgtgga ggagaaccct ggaccaatgg agaaaatgtt ggagtgtgca 1020
ttcatagtct tgtggcttca gcttggctgg ttgagtggag aagaccaggt gacgcagagt 1080
cccgaggccc tgagactcca ggagggagag agtagcagtc tcaactgcag ttacacagtc 1140
agcggtttaa gagggctgtt ctggtatagg caagatcctg ggaaaggccc tgaattcctc 1200
ttcaccctgt attcagctgg ggaagaaaag gagaaagaaa ggctaaaagc cacattaaca 1260

```
aagaaggaaa gctttctgca catcacagcc cctaaacctg aagactcagc cacttatctc   1320

tgtgctgtgc ggatgaacac aggctttcag aaacttgtat ttggaactgg cacccgactt   1380

ctggtcagtc caaacatcca gaatccagag cccgccgtgt atcagctgaa ggacccaaga   1440

tcccaggatt ctaccctgtg cctgttcaca gactttgatt ctcagatcaa tgtgcccaag   1500

acaatggaga gcggcacctt catcacagac aagtgcgtgc tggatatgaa ggctatggac   1560

tccaagtcta acggcgccat cgcctggagc aatcagacct ccttcacatg ccaggatatc   1620

tttaaggaga caaacgccac atacccttct agcgacgtgc catgtgatgc caccctgaca   1680

gagaagagct tcgagacaga catgaacctg aattttcaga atctgctggt catcgtgctg   1740

cggatcctgc tgctgaaggt ggctgggttt aatctgctga tgacactgcg actgtggagt   1800

agctgatga                                                           1809
```

<210> SEQ ID NO 56
<211> LENGTH: 601
<212> TYPE: PRT
<213> ORGANISM: Artificial
<220> FEATURE:
<223> OTHER INFORMATION: Synthetic polypeptide

<400> SEQUENCE: 56

```
Met Thr Ile Arg Leu Leu Cys Tyr Met Gly Phe Tyr Phe Leu Gly Ala
1               5                   10                  15

Gly Leu Met Glu Ala Asp Ile Tyr Gln Thr Pro Arg Tyr Leu Val Ile
            20                  25                  30

Gly Thr Gly Lys Lys Ile Thr Leu Glu Cys Ser Gln Thr Met Gly His
        35                  40                  45

Asp Lys Met Tyr Trp Tyr Gln Gln Asp Pro Gly Met Glu Leu His Leu
    50                  55                  60

Ile His Tyr Ser Tyr Gly Val Asn Ser Thr Glu Lys Gly Asp Leu Ser
65                  70                  75                  80

Ser Glu Ser Thr Val Ser Arg Ile Arg Thr Glu His Phe Pro Leu Thr
                85                  90                  95

Leu Glu Ser Ala Arg Pro Ser His Thr Ser Gln Tyr Leu Cys Ala Ser
            100                 105                 110

Ser Pro Pro Gly Gln Pro Tyr Glu Gln Tyr Phe Gly Pro Gly Thr Arg
        115                 120                 125

Leu Thr Val Thr Glu Asp Leu Arg Asn Val Thr Pro Pro Lys Val Ser
    130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175

Trp Trp Val Asn Gly Lys Glu Val His Ser Gly Val Cys Thr Asp Pro
            180                 185                 190

Gln Ala Tyr Lys Glu Ser Asn Tyr Ser Tyr Cys Leu Ser Ser Arg Leu
        195                 200                 205

Arg Val Ser Ala Thr Phe Trp His Asn Pro Arg Asn His Phe Arg Cys
    210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr Gln Gln Gly Val Leu Ser
```

```
            260                 265                 270

Ala Thr Ile Leu Tyr Glu Ile Leu Leu Gly Lys Ala Thr Leu Tyr Ala
        275                 280                 285

Val Leu Val Ser Thr Leu Val Val Met Ala Met Val Lys Arg Lys Asn
    290                 295                 300

Ser Arg Ala Lys Arg Ser Gly Ser Gly Ala Thr Asn Phe Ser Leu Leu
305                 310                 315                 320

Lys Gln Ala Gly Asp Val Glu Glu Asn Pro Gly Pro Met Glu Lys Met
                325                 330                 335

Leu Glu Cys Ala Phe Ile Val Leu Trp Leu Gln Leu Gly Trp Leu Ser
            340                 345                 350

Gly Glu Asp Gln Val Thr Gln Ser Pro Glu Ala Leu Arg Leu Gln Glu
        355                 360                 365

Gly Glu Ser Ser Ser Leu Asn Cys Ser Tyr Thr Val Ser Gly Leu Arg
    370                 375                 380

Gly Leu Phe Trp Tyr Arg Gln Asp Pro Gly Lys Gly Pro Glu Phe Leu
385                 390                 395                 400

Phe Thr Leu Tyr Ser Ala Gly Glu Glu Lys Glu Lys Glu Arg Leu Lys
                405                 410                 415

Ala Thr Leu Thr Lys Lys Glu Ser Phe Leu His Ile Thr Ala Pro Lys
            420                 425                 430

Pro Glu Asp Ser Ala Thr Tyr Leu Cys Ala Val Arg Met Asn Thr Gly
        435                 440                 445

Phe Gln Lys Leu Val Phe Gly Thr Gly Thr Arg Leu Leu Val Ser Pro
    450                 455                 460

Asn Ile Gln Asn Pro Glu Pro Ala Val Tyr Gln Leu Lys Asp Pro Arg
465                 470                 475                 480

Ser Gln Asp Ser Thr Leu Cys Leu Phe Thr Asp Phe Asp Ser Gln Ile
                485                 490                 495

Asn Val Pro Lys Thr Met Glu Ser Gly Thr Phe Ile Thr Asp Lys Cys
            500                 505                 510

Val Leu Asp Met Lys Ala Met Asp Ser Lys Ser Asn Gly Ala Ile Ala
        515                 520                 525

Trp Ser Asn Gln Thr Ser Phe Thr Cys Gln Asp Ile Phe Lys Glu Thr
    530                 535                 540

Asn Ala Thr Tyr Pro Ser Ser Asp Val Pro Cys Asp Ala Thr Leu Thr
545                 550                 555                 560

Glu Lys Ser Phe Glu Thr Asp Met Asn Leu Asn Phe Gln Asn Leu Leu
                565                 570                 575

Val Ile Val Leu Arg Ile Leu Leu Leu Lys Val Ala Gly Phe Asn Leu
            580                 585                 590

Leu Met Thr Leu Arg Leu Trp Ser Ser
        595                 600
```

<210> SEQ ID NO 57
<211> LENGTH: 1809
<212> TYPE: DNA
<213> ORGANISM: Artificial
<220> FEATURE:
<223> OTHER INFORMATION: Synthetic oligonucleotide

<400> SEQUENCE: 57

```
atgaccatcc ggctgctgtg ctacatgggc ttctattttc tgggcgccgg cctgatggag      60

gccgatatct accagacccc cagatacctg gtcatcggca ccggcaagaa gatcacactg     120
```

```
gagtgttccc agacaatggg ccacgataag atgtactggt atcagcagga ccctggcatg    180

gagctgcacc tgatccacta ctcctatggc gtgaactcta ccgagaaggg cgacctgagc    240

tccgagtcca ccgtgtctcg gatcagaaca gagcacttcc cactgaccct ggagagcgcc    300

aggcctagcc acacatccca gtacctgtgc gcctctagcc cacctggaca gccttacgag    360

cagtatttcg gcccaggcac caggctgacc gtgacagagg atctgcgcaa cgtgacacca    420

cccaaggtga gcctgtttga gccctccaag gccgagatcg ccaataagca gaaggccacc    480

ctggtgtgcc tggcccgcgg cttctttcct gatcacgtgg agctgtcctg gtgggtgaac    540

ggcaaggagg tgcactctgg cgtgtgcacc gacccacagg cctataagga gtctaattac    600

agctattgtc tgtcctctag gctgcgcgtg tccgccacat tctggcacaa ccctaggaat    660

cacttccgct gccaggtgca gtttcacggc ctgtccgagg aggataagtg gccagagggc    720

tctcctaagc cagtgaccca gaatatcagc gccgaggcat ggggaagggc agactgtgga    780

atcacctccg cctcttacca gcagggcgtg ctgagcgcca caatcctgta cgagatcctg    840

ctgggcaagg ccacactgta tgccgtgctg gtgtccaccc tggtggtcat ggctatggtg    900

aagcgcaaga actctcgggc caagagaagc ggatccggag ccacaaattt cagcctgctg    960

aagcaggcag gcgatgtgga ggagaaccca ggacctatgg agaagatgct ggagtgcgcc   1020

tttatcgtgc tgtggctgca gctgggatgg ctgtctggag aggaccaggt gacccagagc   1080

ccagaggccc tgaggctgca ggagggagag agctcctctc tgaattgtag ctacacagtg   1140

tccggcctgc ggggcctgtt ctggtataga caggatcccg gcaagggccc tgagttcctg   1200

tttaccctgt actccgccgg cgaggagaag gagaaggaga gactgaaggc caccctgaca   1260

aagaaggagt cttttctgca catcacagcc ccaaagcccg aggacagcgc cacctatctg   1320

tgcgccgtgc ggatgaacac aggcttccag aagctggtgt ttggcaccgg cacaagactg   1380

ctggtgagcc caaacatcca gaatcctgag ccagccgtgt accagctgaa ggacccccgg   1440

tcccaggatt ctaccctgtg cctgttcaca gactttgata gccagatcaa cgtgcccaag   1500

acaatggagt ccggcacctt catcacagac aagtgcgtgc tggacatgaa ggctatggac   1560

tctaagagca acggcgccat cgcctggtct aatcagacca gcttcacatg ccaggatatc   1620

tttaaggaga ccaatgccac atacccaagc tccgacgtgc cctgtgatgc caccctgaca   1680

gagaagagct tcgagaccga catgaacctg aattttcaga acctgctggt catcgtgctg   1740

aggatcctgc tgctgaaggt ggccggcttt aatctgctga tgacactgcg cctgtggtct   1800

agctgatga                                                           1809
```

<210> SEQ ID NO 58
<211> LENGTH: 1833
<212> TYPE: DNA
<213> ORGANISM: Homo sapiens

<400> SEQUENCE: 58

```
atgactatca ggctcctctg ctacatgggc ttttattttc tgggggcagg cctcatggaa     60

gctgacatct accagacccc aagatacctt gttataggga caggaaagaa gatcactctg    120

gaatgttctc aaaccatggg ccatgacaaa atgtactggt atcaacaaga tccaggaatg    180

gaactacacc tcatccacta ttcctatgga gttaattcca cagagaaggg agatctttcc    240

tctgagtcaa cagtctccag aataaggacg gagcattttc ccctgaccct ggagtctgcc    300

aggccctcac atacctctca gtacctctgt gccagcagtc cgccgggaca gccttacgag    360

cagtacttcg ggccgggcac caggctcacg gtcacagagg acctgaacaa ggtgttccca    420
```

```
cccgaggtcg ctgtgtttga gccatcagaa gcagagatct cccacaccca aaaggccaca    480

ctggtgtgcc tggccacagg cttcttcccc gaccacgtgg agctgagctg gtgggtgaat    540

gggaaggagg tgcacagtgg ggtcagcacg gacccgcagc cctcaagga gcagcccgcc     600

ctcaatgact ccagatactg cctgagcagc cgcctgaggg tctcggccac cttctggcag    660

aacccccgca accacttccg ctgtcaagtc cagttctacg ggctctcgga gaatgacgag    720

tggacccagg atagggccaa acccgtcacc cagatcgtca gcgccgaggc ctggggtaga    780

gcagactgtg gctttacctc ggtgtcctac cagcaagggg tcctgtctgc caccatcctc    840

tatgagatcc tgctagggaa ggccaccctg tatgctgtgc tggtcagcgc ccttgtgttg    900

atggccatgg tcaagagaaa ggatttcagg gcaaagcgga gcggaagcgg agccacaaat    960

ttctctctgc tgaagcaggc aggcgatgtg gaggagaacc ctggaccaat ggagaaaatg   1020

ttggagtgtg cattcatagt cttgtggctt cagcttggct ggttgagtgg agaagaccag   1080

gtgacgcaga gtcccgaggc cctgagactc caggagggag agagtagcag tctcaactgc   1140

agttacacag tcagcggttt aagagggctg ttctggtata ggcaagatcc tgggaaaggc   1200

cctgaattcc tcttcaccct gtattcagct ggggaagaaa aggagaaaga aaggctaaaa   1260

gccacattaa caaagaagga aagctttctg cacatcacag cccctaaacc tgaagactca   1320

gccacttatc tctgtgctgt gcggatgaac acaggctttc agaaacttgt atttggaact   1380

ggcacccgac ttctggtcag tccaaatatc cagaaccctg accctgccgt gtaccagctg   1440

agagactcta aatccagtga caagtctgtc tgcctattca ccgattttga ttctcaaaca   1500

aatgtgtcac aaagtaagga ttctgatgtg tatatcacag acaaaactgt gctagacatg   1560

aggtctatgg acttcaagag caacagtgct gtggcctgga gcaacaaatc tgactttgca   1620

tgtgcaaacg ccttcaacaa cagcattatt ccagaagaca ccttcttccc cagcccagaa   1680

agttcctgtg atgtcaagct ggtcgagaaa agctttgaaa cagatacgaa cctaaacttt   1740

caaaacctgt cagtgattgg gttccgaatc ctcctcctga aagtggccgg gtttaatctg   1800

ctcatgacgc tgcggctgtg gtccagctga tga                                1833
```

<210> SEQ ID NO 59
<211> LENGTH: 609
<212> TYPE: PRT
<213> ORGANISM: Homo sapiens

<400> SEQUENCE: 59

```
Met Thr Ile Arg Leu Leu Cys Tyr Met Gly Phe Tyr Phe Leu Gly Ala
1               5                   10                  15

Gly Leu Met Glu Ala Asp Ile Tyr Gln Thr Pro Arg Tyr Leu Val Ile
            20                  25                  30

Gly Thr Gly Lys Lys Ile Thr Leu Glu Cys Ser Gln Thr Met Gly His
        35                  40                  45

Asp Lys Met Tyr Trp Tyr Gln Gln Asp Pro Gly Met Glu Leu His Leu
    50                  55                  60

Ile His Tyr Ser Tyr Gly Val Asn Ser Thr Glu Lys Gly Asp Leu Ser
65                  70                  75                  80

Ser Glu Ser Thr Val Ser Arg Ile Arg Thr Glu His Phe Pro Leu Thr
                85                  90                  95

Leu Glu Ser Ala Arg Pro Ser His Thr Ser Gln Tyr Leu Cys Ala Ser
            100                 105                 110

Ser Pro Pro Gly Gln Pro Tyr Glu Gln Tyr Phe Gly Pro Gly Thr Arg
```

```
        115                 120                 125

Leu Thr Val Thr Glu Asp Leu Asn Lys Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Phe Arg Ala Lys Arg Ser Gly Ser Gly Ala Thr Asn
305                 310                 315                 320

Phe Ser Leu Leu Lys Gln Ala Gly Asp Val Glu Glu Asn Pro Gly Pro
                325                 330                 335

Met Glu Lys Met Leu Glu Cys Ala Phe Ile Val Leu Trp Leu Gln Leu
            340                 345                 350

Gly Trp Leu Ser Gly Glu Asp Gln Val Thr Gln Ser Pro Glu Ala Leu
        355                 360                 365

Arg Leu Gln Glu Gly Glu Ser Ser Ser Leu Asn Cys Ser Tyr Thr Val
    370                 375                 380

Ser Gly Leu Arg Gly Leu Phe Trp Tyr Arg Gln Asp Pro Gly Lys Gly
385                 390                 395                 400

Pro Glu Phe Leu Phe Thr Leu Tyr Ser Ala Gly Glu Glu Lys Glu Lys
                405                 410                 415

Glu Arg Leu Lys Ala Thr Leu Thr Lys Lys Glu Ser Phe Leu His Ile
            420                 425                 430

Thr Ala Pro Lys Pro Glu Asp Ser Ala Thr Tyr Leu Cys Ala Val Arg
        435                 440                 445

Met Asn Thr Gly Phe Gln Lys Leu Val Phe Gly Thr Gly Thr Arg Leu
    450                 455                 460

Leu Val Ser Pro Asn Ile Gln Asn Pro Asp Pro Ala Val Tyr Gln Leu
465                 470                 475                 480

Arg Asp Ser Lys Ser Ser Asp Lys Ser Val Cys Leu Phe Thr Asp Phe
                485                 490                 495

Asp Ser Gln Thr Asn Val Ser Gln Ser Lys Asp Ser Asp Val Tyr Ile
            500                 505                 510

Thr Asp Lys Thr Val Leu Asp Met Arg Ser Met Asp Phe Lys Ser Asn
        515                 520                 525

Ser Ala Val Ala Trp Ser Asn Lys Ser Asp Phe Ala Cys Ala Asn Ala
    530                 535                 540
```

```
Phe Asn Asn Ser Ile Ile Pro Glu Asp Thr Phe Phe Pro Ser Pro Glu
545                 550                 555                 560

Ser Ser Cys Asp Val Lys Leu Val Glu Lys Ser Phe Glu Thr Asp Thr
                565                 570                 575

Asn Leu Asn Phe Gln Asn Leu Ser Val Ile Gly Phe Arg Ile Leu Leu
            580                 585                 590

Leu Lys Val Ala Gly Phe Asn Leu Leu Met Thr Leu Arg Leu Trp Ser
        595                 600                 605

Ser


<210> SEQ ID NO 60
<211> LENGTH: 1833
<212> TYPE: DNA
<213> ORGANISM: Artificial
<220> FEATURE:
<223> OTHER INFORMATION: Synthetic oligonucleotide

<400> SEQUENCE: 60

atgaccatcc ggctgctgtg ctacatgggc ttctattttc tgggcgccgg cctgatggag      60

gccgatatct accagacccc cagatacctg gtcatcggca ccggcaagaa gatcacactg     120

gagtgttccc agacaatggg ccacgataag atgtactggt atcagcagga ccctggcatg     180

gagctgcacc tgatccacta ctcctatggc gtgaactcta ccgagaaggg cgacctgagc     240

tccgagtcca ccgtgtctcg gatcagaaca gagcacttcc cactgaccct ggagagcgcc     300

aggcctagcc acacatccca gtacctgtgc gcctctagcc cacctggaca gccttacgag     360

cagtatttcg gcccaggcac caggctgacc gtgacagagg acctgaataa ggtgttcccc     420

cctgaggtgg ccgtgtttga gccttccgag gccgagatct ctcacaccca gaaggccacc     480

ctggtgtgcc tggcaaccgg cttctttcca gatcacgtgg agctgagctg gtgggtgaac     540

ggcaaggagg tgcacagcgg cgtgtccacc gacccacagc cctgaagga gcagcccgcc     600

ctgaatgata gcagatattg cctgtctagc cggctgagag tgtccgccac cttttggcag     660

aaccctcgga atcacttcag atgtcaggtg cagttttacg gcctgagcga gaatgacgag     720

tggacccagg atagggccaa gcccgtgaca cagatcgtgt ccgccgaggc atggggaagg     780

gcagactgcg gcttcacatc cgtgtcttat cagcagggcg tgctgagcgc caccatcctg     840

tatgagatcc tgctgggcaa ggccacactg tacgccgtgc tggtgtccgc cctggtgctg     900

atggctatgg tgaagcggaa ggactttcgg gccaagagaa gcggatccgg agccacaaat     960

ttcagcctgc tgaagcaggc aggcgatgtg gaggagaacc caggacctat ggagaagatg    1020

ctggagtgcg cctttatcgt gctgtggctg cagctgggat ggctgtctgg agaggaccag    1080

gtgacccaga gcccagaggc cctgaggctg caggagggag agagctcctc tctgaattgt    1140

agctacacag tgtccggcct gcggggcctg ttctggtata gacaggatcc cggcaagggc    1200

cctgagttcc tgtttaccct gtactccgcc ggcgaggaga aggagaagga gagactgaag    1260

gccaccctga caaagaagga gtcttttctg cacatcacag ccccaaagcc cgaggacagc    1320

gccacctatc tgtgcgccgt gcggatgaac acaggcttcc agaagctggt gtttggcacc    1380

ggcacaagac tgctggtgag cccaaacatc cagaatcccg accctgccgt gtatcagctg    1440

agggactcca agtcctctga taagagcgtg tgcctgttca ccgactttga ttctcagaca    1500

aacgtgagcc agtccaagga cagcgacgtg tacatcaccg acaagacagt gctggatatg    1560

cggagcatgg acttcaagtc taacagcgcc gtggcctgga gcaataagtc cgatttcgcc    1620
```

```
tgcgccaatg cctttaacaa ttccatcatc cctgaggata ccttctttcc atctcccgag   1680

agctcctgtg acgtgaagct ggtggagaag tctttcgaga ccgatacaaa cctgaatttt   1740

cagaacctga gcgtgatcgg cttccggatc ctgctgctga aggtggccgg cttcaatctg   1800

ctgatgacac tgagactgtg gtctagctga tga                                1833
```

<210> SEQ ID NO 61
<211> LENGTH: 9
<212> TYPE: PRT
<213> ORGANISM: Artificial
<220> FEATURE:
<223> OTHER INFORMATION: Synthetic polypeptide

<400> SEQUENCE: 61

```
Leu Ala Gly Val Val Asn Leu Pro Lys
1               5
```

<210> SEQ ID NO 62
<211> LENGTH: 9
<212> TYPE: PRT
<213> ORGANISM: Artificial
<220> FEATURE:
<223> OTHER INFORMATION: Synthetic polypeptide

<400> SEQUENCE: 62

```
Leu Ala Gly Ala Val Asn Leu Pro Lys
1               5
```

<210> SEQ ID NO 63
<211> LENGTH: 9
<212> TYPE: PRT
<213> ORGANISM: Artificial
<220> FEATURE:
<223> OTHER INFORMATION: Synthetic polypeptide

<400> SEQUENCE: 63

```
Leu Ala Gly Cys Val Asn Leu Pro Lys
1               5
```

<210> SEQ ID NO 64
<211> LENGTH: 9
<212> TYPE: PRT
<213> ORGANISM: Artificial
<220> FEATURE:
<223> OTHER INFORMATION: Synthetic polypeptide

<400> SEQUENCE: 64

```
Leu Ala Gly Ser Val Asn Leu Pro Lys
1               5
```

<210> SEQ ID NO 65
<211> LENGTH: 9
<212> TYPE: PRT
<213> ORGANISM: Homo sapiens

<400> SEQUENCE: 65

```
Leu Ala Gly Gly Val Asn Leu Pro Lys
1               5
```

<210> SEQ ID NO 66
<211> LENGTH: 81
<212> TYPE: PRT
<213> ORGANISM: Artificial
<220> FEATURE:
<223> OTHER INFORMATION: Synthetic polypeptide

```
<400> SEQUENCE: 66

Lys Glu Ser Ser Lys Phe Pro Phe Gly Ile Ser Pro Ala Gln Ser His
1               5                   10                  15

Arg Asn Ile Lys Ile Leu Glu Asp Glu Pro Pro Thr Val Arg Met Arg
            20                  25                  30

Pro His Cys Val Pro Phe Trp Thr Gly Arg Ile Leu Leu Pro Ser Ala
        35                  40                  45

Ala Ser Val Cys Pro Ile Pro Phe Glu Ala Cys His Leu Cys Gln Ala
    50                  55                  60

Met Thr Leu Arg Cys Pro Asn Thr Gln Gly Cys Cys Ser Ser Trp Ala
65                  70                  75                  80

Ser


<210> SEQ ID NO 67
<211> LENGTH: 81
<212> TYPE: PRT
<213> ORGANISM: Homo sapiens

<400> SEQUENCE: 67

Lys Glu Ser Ser Lys Phe Pro Phe Gly Ile Ser Pro Ala Gln Ser His
1               5                   10                  15

Arg Asn Ile Lys Ile Leu Glu Asp Glu Pro His Ser Lys Asp Glu Thr
            20                  25                  30

Pro Leu Cys Thr Leu Leu Asp Trp Gln Asp Ser Leu Ala Lys Arg Cys
        35                  40                  45

Val Cys Val Ser Asn Thr Ile Arg Ser Leu Ser Phe Val Pro Gly Asn
    50                  55                  60

Asp Phe Glu Met Ser Lys His Pro Gly Leu Leu Leu Ile Leu Gly Lys
65                  70                  75                  80

Leu


<210> SEQ ID NO 68
<211> LENGTH: 15
<212> TYPE: PRT
<213> ORGANISM: Artificial
<220> FEATURE:
<223> OTHER INFORMATION: Synthetic polypeptide

<400> SEQUENCE: 68

Ile Leu Glu Asp Glu Pro Pro Thr Val Arg Met Arg Pro His Cys
1               5                   10                  15


<210> SEQ ID NO 69
<211> LENGTH: 22
<212> TYPE: PRT
<213> ORGANISM: Porcine teschovirus-1

<400> SEQUENCE: 69

Gly Ser Gly Ala Thr Asn Phe Ser Leu Leu Lys Gln Ala Gly Asp Val
1               5                   10                  15

Glu Glu Asn Pro Gly Pro
            20


<210> SEQ ID NO 70
<211> LENGTH: 21
<212> TYPE: PRT
<213> ORGANISM: Thosea asigna virus

<400> SEQUENCE: 70
```

```
Gly Ser Gly Glu Gly Arg Gly Ser Leu Leu Thr Cys Gly Asp Val Glu
1               5                   10                  15

Glu Asn Pro Gly Pro
            20


<210> SEQ ID NO 71
<211> LENGTH: 23
<212> TYPE: PRT
<213> ORGANISM: Equine rhinitis A virus

<400> SEQUENCE: 71

Gly Ser Gly Gln Cys Thr Asn Tyr Ala Leu Leu Lys Leu Ala Gly Asp
1               5                   10                  15

Val Glu Ser Asn Pro Gly Pro
            20


<210> SEQ ID NO 72
<211> LENGTH: 25
<212> TYPE: PRT
<213> ORGANISM: Foot-and-mouth disease virus

<400> SEQUENCE: 72

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25


<210> SEQ ID NO 73
<211> LENGTH: 4
<212> TYPE: PRT
<213> ORGANISM: Artificial
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Xaa = any amino acid

<400> SEQUENCE: 73

Arg Xaa Lys Arg
1


<210> SEQ ID NO 74
<211> LENGTH: 4
<212> TYPE: PRT
<213> ORGANISM: Artificial
<220> FEATURE:
<223> OTHER INFORMATION: Synthetic polypeptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 74

Arg Xaa Arg Arg
1


<210> SEQ ID NO 75
<211> LENGTH: 5
<212> TYPE: PRT
<213> ORGANISM: Artificial
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa = Lys or Arg
```

<220> FEATURE:
<221> NAME/KEY: MISC_FEATURE
<222> LOCATION: (3)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = Lys or Arg

<400> SEQUENCE: 75

Xaa Arg Xaa Xaa Arg
1               5

<210> SEQ ID NO 76
<211> LENGTH: 4
<212> TYPE: PRT
<213> ORGANISM: Artificial
<220> FEATURE:
<223> OTHER INFORMATION: Synthetic polypeptide
<220> FEATURE:
<221> NAME/KEY: misc_feature
<222> LOCATION: (2)..(3)
<223> OTHER INFORMATION: Xaa can be any naturally occurring amino acid

<400> SEQUENCE: 76

Arg Xaa Xaa Arg
1

<210> SEQ ID NO 77
<211> LENGTH: 4
<212> TYPE: PRT
<213> ORGANISM: Artificial
<220> FEATURE:
<223> OTHER INFORMATION: Synthetic polypeptide

<400> SEQUENCE: 77

Arg Gln Lys Arg
1

<210> SEQ ID NO 78
<211> LENGTH: 912
<212> TYPE: DNA
<213> ORGANISM: Artificial
<220> FEATURE:
<223> OTHER INFORMATION: Synthetic oligonucleotide

<400> SEQUENCE: 78
atgggcttca ggctcctctg ctgtgtggcc ttttgtctcc tgggagcagg cccagtggat     60
tctggagtca cacaaacccc aaagcacctg atcacagcaa ctggacagca agtgacgctg    120
agatgctccc ctaggtctgg agacctctct gtgtactggt accaacagag cctggaccag    180
ggcctccagt tcctcattca gtattataat ggagaagaga gagcaaaagg aaacattctt    240
gaacgattct ccgcacaaca gttccctgac ttgcactctg aactaaacct gagctctctg    300
gagctggggg actcagcttt gtatttctgt gccagcagcg cggcagttca ctatggctac    360
accttcggtt cggggaccag gttaaccgtt gtagaggacc tgagaaacgt gacacccccct   420 aaggtgagcc tgttcgagcc ctccaaggcc gagatcgcca ataagcagaa ggccaccctg    480
gtgtgcctgg caaggggctt ctttcctgat cacgtggagc tgtcttggtg ggtgaacggc    540
aaggaggtgc acagcggcgt gtgcaccgac ccacaggcct ataaggagag caattattcc    600
tactgtctgt ctagccggct gagagtgagc gccacatttt ggcacaaccc tcggaatcac    660
ttcagatgcc aggtgcagtt tcacggcctg tctgaggagg ataagtggcc agagggcagc    720
ccaaagccag tgacccagaa catctccgcc gaggcatggg gaagagcaga ctgtggcatc    780

```
accagcgcct cctaccagca gggcgtgctg tccgccacaa tcctgtatga gatcctgctg    840

ggcaaggcca ccctgtacgc cgtgctggtg agcacactgg tggtcatggc tatggtgaag    900

aggaagaact cc                                                         912
```

<210> SEQ ID NO 79
<211> LENGTH: 819
<212> TYPE: DNA
<213> ORGANISM: Artificial
<220> FEATURE:
<223> OTHER INFORMATION: Synthetic oligonucleotide

<400> SEQUENCE: 79

```
atgtcacttt ctagcctgct gaaggtggtc acagcttcac tgtggctagg acctggcatt     60

gcccagaaga taactcaaac ccaaccagga atgttcgtgc aggaaaagga ggctgtgact    120

ctggactgca catatgacac cagtgatcaa agttatggtc tcttctggta caagcagccc    180

agcagtgggg aaatgatttt tcttatttat caggggtctt atgacgagca aaatgcaaca    240

gaaggtcgct actcattgaa tttccagaag gcaagaaaat ccgccaacct tgtcatctcc    300

gcttcacaac tgggggactc agcaatgtat ttctgtgcaa tgagagagca gggagcccag    360

aagctggtat ttggccaagg aaccaggctg actatcaacc caaacatcca gaatccagag    420

cccgccgtgt atcagctgaa ggacccaaga tcccaggatt ctaccctgtg cctgttcaca    480

gactttgatt ctcagatcaa tgtgcccaag acaatggaga gcggcacctt catcacagac    540

aagtgcgtgc tggatatgaa ggctatggac tccaagtcta acggcgccat cgcctggagc    600

aatcagacct ccttcacatg ccaggatatc tttaaggaga caaacgccac atacccttct    660

agcgacgtgc catgtgatgc caccctgaca gagaagagct tcgagacaga catgaacctg    720

aattttcaga atctgctggt catcgtgctg cggatcctgc tgctgaaggt ggctgggttt    780

aatctgctga tgacactgcg actgtggagt agctgatga                            819
```

<210> SEQ ID NO 80
<211> LENGTH: 912
<212> TYPE: DNA
<213> ORGANISM: Artificial
<220> FEATURE:
<223> OTHER INFORMATION: Synthetic oligonucleotide

<400> SEQUENCE: 80

```
atgggcttcc ggctgctgtg ctgcgtggca ttttgcctgc tgggagcagg acctgtggat     60

agcggcgtga cccagacacc aaagcacctg atcaccgcaa caggacagca ggtgaccctg    120

aggtgttccc caagatctgg cgatctgtcc gtgtactggt atcagcagtc tctggaccag    180

ggcctgcagt tcctgatcca gtactataac ggcgaggagc gggccaaggg caatatcctg    240

gagagattca gcgcccagca gtttcctgat ctgcactccg agctgaatct gagctccctg    300

gagctgggcg actccgccct gtacttctgc gcctctagcg ccgcagtgca ctacggctat    360

acctttggct ctggcaccag gctgacagtg gtggaggacc tgcgcaatgt gacaccccct    420

aaggtgtctc tgttcgagcc cagcaaggcc gagatcgcca acaagcagaa ggccaccctg    480

gtgtgcctgg cccggggctt ctttcctgat cacgtggagc tgtcctggtg ggtgaatggc    540

aaggaggtgc actctggcgt gtgcaccgac ccacaggcct acaaggagag caactactcc    600

tattgtctgt cctctcggct gagagtgagc gccacatttt ggcacaaccc taggaatcac    660

ttccgctgcc aggtgcagtt tcacggcctg tctgaggagg ataagtggcc agagggaagc    720
```

```
ccaaagccag tgacccagaa tatctccgcc gaggcatggg gaagggcaga ctgtggaatc    780

acctctgcca gctatcagca gggcgtgctg tccgccacaa tcctgtacga gatcctgctg    840

ggcaaggcca ccctgtatgc cgtgctggtg tccacactgg tggtcatggc tatggtgaag    900

aggaagaaca gc                                                        912


<210> SEQ ID NO 81
<211> LENGTH: 819
<212> TYPE: DNA
<213> ORGANISM: Artificial
<220> FEATURE:
<223> OTHER INFORMATION: Synthetic oligonucleotide

<400> SEQUENCE: 81

atgtctctga gctccctgct gaaggtcgtg acagcaagcc tgtggctggg accaggaatc     60

gcacagaaga tcacccagac acagcctggc atgtttgtgc aggagaagga ggccgtgacc    120

ctggactgca cctacgacac atctgatcag agctacggcc tgttctggta taagcagcca    180

tctagcggcg agatgatctt tctgatctac cagggcagct atgatgagca gaacgccaca    240

gagggccggt actctctgaa tttccagaag gccagaaaga gcgccaacct ggtcatcagc    300

gcctcccagc tgggcgactc cgccatgtat ttctgtgcca tgagggagca gggcgcccag    360

aagctggtgt ttggccaggg cacccgcctg acaatcaacc caaatatcca gaatcccgag    420

cctgccgtgt accagctgaa ggaccccaga tcccaggatt ctaccctgtg cctgttcaca    480

gactttgata gccagatcaa cgtgcccaag acaatggagt ccggcacctt catcacagac    540

aagtgcgtgc tggacatgaa ggctatggac tctaagagca acggcgccat cgcctggagc    600

aatcagacct ccttcacatg ccaggatatc tttaaggaga ccaacgccac atatccatcc    660

tctgacgtgc cctgtgatgc caccctgaca gagaagtcct tcgagaccga catgaacctg    720

aattttcaga atctgctggt catcgtgctg cggatcctgc tgctgaaggt ggccggcttt    780

aacctgctga tgacactgag actgtggagc tcctgatga                           819


<210> SEQ ID NO 82
<211> LENGTH: 924
<212> TYPE: DNA
<213> ORGANISM: Homo sapiens

<400> SEQUENCE: 82

atgggcttca ggctcctctg ctgtgtggcc ttttgtctcc tgggagcagg cccagtggat     60

tctggagtca cacaaacccc aaagcacctg atcacagcaa ctggacagca agtgacgctg    120

agatgctccc ctaggtctgg agacctctct gtgtactggt accaacagag cctggaccag    180

ggcctccagt tcctcattca gtattataat ggagaagaga gagcaaaagg aaacattctt    240

gaacgattct ccgcacaaca gttccctgac ttgcactctg aactaaacct gagctctctg    300

gagctggggg actcagcttt gtatttctgt gccagcagcg cggcagttca ctatggctac    360

accttcggtt cggggaccag gttaaccgtt gtagaggacc tgaacaaggt gttcccaccc    420

gaggtcgctg tgtttgagcc atcagaagca gagatctccc acacccaaaa ggccacactg    480

gtgtgcctgg ccacaggctt cttccccgac cacgtggagc tgagctggtg ggtgaatggg    540

aaggaggtgc acagtggggt cagcacggac ccgcagcccc tcaaggagca gcccgccctc    600

aatgactcca gatactgcct gagcagccgc ctgagggtct cggccacctt ctggcagaac    660

ccccgcaacc acttccgctg tcaagtccag ttctacgggc tctcggagaa tgacgagtgg    720

acccaggata gggccaaacc cgtcacccag atcgtcagcg ccgaggcctg gggtagagca    780
```

gactgtggct ttacctcggt gtcctaccag caaggggtcc tgtctgccac catcctctat 840
gagatcctgc tagggaaggc caccctgtat gctgtgctgg tcagcgccct tgtgttgatg 900
gccatggtca agagaaagga tttc 924

<210> SEQ ID NO 83
<211> LENGTH: 831
<212> TYPE: DNA
<213> ORGANISM: Homo sapiens

<400> SEQUENCE: 83
atgtcacttt ctagcctgct gaaggtggtc acagcttcac tgtggctagg acctggcatt 60
gcccagaaga taactcaaac ccaaccagga atgttcgtgc aggaaaagga ggctgtgact 120
ctggactgca catatgacac cagtgatcaa agttatggtc tcttctggta caagcagccc 180
agcagtgggg aaatgatttt tcttatttat caggggtctt atgacgagca aaatgcaaca 240
gaaggtcgct actcattgaa tttccagaag gcaagaaaat ccgccaacct tgtcatctcc 300
gcttcacaac tgggggactc agcaatgtat ttctgtgcaa tgagagagca gggagcccag 360
aagctggtat ttggccaagg aaccaggctg actatcaacc caaatatcca gaaccctgac 420
cctgccgtgt accagctgag agactctaaa tccagtgaca agtctgtctg cctattcacc 480
gattttgatt ctcaaacaaa tgtgtcacaa agtaaggatt ctgatgtgta tatcacagac 540
aaaactgtgc tagacatgag gtctatggac ttcaagagca acagtgctgt ggcctggagc 600
aacaaatctg actttgcatg tgcaaacgcc ttcaacaaca gcattattcc agaagacacc 660
ttcttcccca gcccagaaag ttcctgtgat gtcaagctgg tcgagaaaag ctttgaaaca 720
gatacgaacc taaactttca aaacctgtca gtgattgggt tccgaatcct cctcctgaaa 780
gtggccgggt ttaatctgct catgacgctg cggctgtggt ccagctgatg a 831

<210> SEQ ID NO 84
<211> LENGTH: 924
<212> TYPE: DNA
<213> ORGANISM: Artificial
<220> FEATURE:
<223> OTHER INFORMATION: Synthetic oligonucleotide

<400> SEQUENCE: 84
atgggcttcc ggctgctgtg ctgcgtggca ttttgcctgc tgggagcagg acctgtggat 60
agcggcgtga cccagacacc aaagcacctg atcaccgcaa caggacagca ggtgaccctg 120
aggtgttccc caagatctgg cgatctgtcc gtgtactggt atcagcagtc tctggaccag 180
ggcctgcagt tcctgatcca gtactataac ggcgaggagc gggccaaggg caatatcctg 240
gagagattca gcgcccagca gtttcctgat ctgcactccg agctgaatct gagctccctg 300
gagctgggcg actccgccct gtacttctgc gcctctagcg ccgcagtgca ctacggctat 360
acctttggct ctggcaccag gctgacagtg gtggaggacc tgaataaggt gttcccccct 420
gaggtggccg tgtttgagcc ttccgaggcc gagatctctc acacccagaa ggccaccctg 480
gtgtgcctgg caaccggctt ctttccagat cacgtggagc tgagctggtg ggtgaacggc 540
aaggaggtgc acagcggcgt gtccaccgac ccacagcccc tgaaggagca gcccgccctg 600
aatgatagca gatattgcct gtctagccgg ctgagagtgt ccgccacctt ttggcagaac 660
cctcggaatc acttcagatg tcaggtgcag ttttacggcc tgagcgagaa tgacgagtgg 720
acccaggata gggccaagcc cgtgacacag atcgtgtccg ccgaggcatg gggaagggca 780
gactgcggct tcacatccgt gtcttatcag cagggcgtgc tgagcgccac catcctgtat 840
gagatcctgc tgggcaaggc cacactgtac gccgtgctgg tgtccgccct ggtgctgatg 900
gctatggtga agcggaagga cttt 924

<210> SEQ ID NO 85
<211> LENGTH: 831
<212> TYPE: DNA
<213> ORGANISM: Artificial
<220> FEATURE:
<223> OTHER INFORMATION: Synthetic oligonucleotide

<400> SEQUENCE: 85
atgtctctga gctccctgct gaaggtcgtg acagcaagcc tgtggctggg accaggaatc 60
gcacagaaga tcacccagac acagcctggc atgtttgtgc aggagaagga ggccgtgacc 120
ctggactgca cctacgacac atctgatcag agctacggcc tgttctggta taagcagcca 180
tctagcggcg agatgatctt tctgatctac cagggcagct atgatgagca gaacgccaca 240
gagggccggt actctctgaa tttccagaag gccagaaaga gcgccaacct ggtcatcagc 300
gcctcccagc tgggcgactc cgccatgtat ttctgtgcca tgagggagca gggcgcccag 360
aagctggtgt ttggccaggg cacccgcctg acaatcaacc caaacatcca gaatcccgac 420
cctgccgtgt atcagctgag ggactccaag tcctctgata agagcgtgtg cctgttcacc 480
gactttgatt ctcagacaaa cgtgagccag tccaaggaca gcgacgtgta catcaccgac 540
aagacagtgc tggatatgcg gagcatggac ttcaagtcta acagcgccgt ggcctggagc 600
aataagtccg atttcgcctg cgccaatgcc tttaacaatt ccatcatccc tgaggatacc 660
ttctttccat ctcccgagag ctcctgtgac gtgaagctgg tggagaagtc tttcgagacc 720
gatacaaacc tgaattttca gaacctgagc gtgatcggct tccggatcct gctgctgaag 780
gtggccggct tcaatctgct gatgacactg agactgtggt ctagctgatg a 831

<210> SEQ ID NO 86
<211> LENGTH: 915
<212> TYPE: DNA
<213> ORGANISM: Homo sapiens

<400> SEQUENCE: 86
atgactatca ggctcctctg ctacatgggc ttttattttc tgggggcagg cctcatggaa 60
gctgacatct accagacccc aagatacctt gttataggga caggaaagaa gatcactctg 120
gaatgttctc aaaccatggg ccatgacaaa atgtactggt atcaacaaga tccaggaatg 180
gaactacacc tcatccacta ttcctatgga gttaattcca cagagaaggg agatctttcc 240
tctgagtcaa cagtctccag aataaggacg gagcattttc ccctgaccct ggagtctgcc 300
aggccctcac atacctctca gtacctctgt gccagcagtc cgccgggaca gccttacgag 360
cagtacttcg ggccgggcac caggctcacg gtcacagagg acctgagaaa cgtgacaccc 420
cctaaggtga gcctgttcga gccctccaag gccgagatcg ccaataagca gaaggccacc 480
ctggtgtgcc tggcaagggg cttctttcct gatcacgtgg agctgtcttg gtgggtgaac 540
ggcaaggagg tgcacagcgg cgtgtgcacc gacccacagg cctataagga gagcaattat 600
tcctactgtc tgtctagccg gctgagagtg agcgccacat tttggcacaa ccctcggaat 660
cacttcagat gccaggtgca gtttcacggc ctgtctgagg aggataagtg gccagagggc 720
agcccaaagc cagtgaccca gaacatctcc gccgaggcat ggggaagagc agactgtggc 780
atcaccagcg cctcctacca gcagggcgtg ctgtccgcca caatcctgta tgagatcctg 840
ctgggcaagg ccaccctgta cgccgtgctg gtgagcacac tggtggtcat ggctatggtg 900
aagaggaaga actcc 915

<210> SEQ ID NO 87
<211> LENGTH: 813
<212> TYPE: DNA
<213> ORGANISM: Homo sapiens

<400> SEQUENCE: 87
atggagaaaa tgttggagtg tgcattcata gtcttgtggc ttcagcttgg ctggttgagt 60
ggagaagacc aggtgacgca gagtcccgag gccctgagac tccaggaggg agagagtagc 120
agtctcaact gcagttacac agtcagcggt ttaagagggc tgttctggta taggcaagat 180
cctgggaaag gccctgaatt cctcttcacc ctgtattcag ctggggaaga aaaggagaaa 240
gaaaggctaa aagccacatt aacaaagaag gaaagctttc tgcacatcac agcccctaaa 300
cctgaagact cagccactta tctctgtgct gtgcggatga acacaggctt tcagaaactt 360
gtatttggaa ctggcacccg acttctggtc agtccaaaca tccagaatcc agagcccgcc 420
gtgtatcagc tgaaggaccc aagatcccag gattctaccc tgtgcctgtt cacagacttt 480
gattctcaga tcaatgtgcc caagacaatg gagagcggca ccttcatcac agacaagtgc 540
gtgctggata tgaaggctat ggactccaag tctaacggcg ccatcgcctg gagcaatcag 600
acctccttca catgccagga tatctttaag gagacaaacg ccacataccc ttctagcgac 660
gtgccatgtg atgccaccct gacagagaag agcttcgaga cagacatgaa cctgaatttt 720
cagaatctgc tggtcatcgt gctgcggatc ctgctgctga aggtggctgg gtttaatctg 780
ctgatgacac tgcgactgtg gagtagctga tga 813

<210> SEQ ID NO 88
<211> LENGTH: 915
<212> TYPE: DNA
<213> ORGANISM: Artificial
<220> FEATURE:
<223> OTHER INFORMATION: Synthetic oligonucleotide

<400> SEQUENCE: 88
atgaccatcc ggctgctgtg ctacatgggc ttctattttc tgggcgccgg cctgatggag 60
gccgatatct accagacccc cagatacctg gtcatcggca ccggcaagaa gatcacactg 120
gagtgttccc agacaatggg ccacgataag atgtactggt atcagcagga ccctggcatg 180
gagctgcacc tgatccacta ctcctatggc gtgaactcta ccgagaaggg cgacctgagc 240
tccgagtcca ccgtgtctcg gatcagaaca gagcacttcc cactgaccct ggagagcgcc 300
aggcctagcc acacatccca gtacctgtgc gcctctagcc cacctggaca gccttacgag 360
cagtatttcg gcccaggcac caggctgacc gtgacagagg atctgcgcaa cgtgacacca 420
cccaaggtga gcctgtttga gccctccaag gccgagatcg ccaataagca gaaggccacc 480
ctggtgtgcc tggcccgcgg cttctttcct gatcacgtgg agctgtcctg gtgggtgaac 540
ggcaaggagg tgcactctgg cgtgtgcacc gacccacagg cctataagga gtctaattac 600
agctattgtc tgtcctctag gctgcgcgtg tccgccacat tctggcacaa ccctaggaat 660
cacttccgct gccaggtgca gtttcacggc ctgtccgagg aggataagtg gccagagggc 720
tctcctaagc cagtgaccca gaatatcagc gccgaggcat ggggaagggc agactgtgga 780
atcacctccg cctcttacca gcagggcgtg ctgagcgcca caatcctgta cgagatcctg 840

```
ctgggcaagg ccacactgta tgccgtgctg gtgtccaccc tggtggtcat ggctatggtg    900

aagcgcaaga actct                                                     915


<210> SEQ ID NO 89
<211> LENGTH: 813
<212> TYPE: DNA
<213> ORGANISM: Artificial
<220> FEATURE:
<223> OTHER INFORMATION: Synthetic oligonucleotide

<400> SEQUENCE: 89

atggagaaga tgctggagtg cgcctttatc gtgctgtggc tgcagctggg atggctgtct     60

ggagaggacc aggtgaccca gagcccagag gccctgaggc tgcaggaggg agagagctcc    120

tctctgaatt gtagctacac agtgtccggc ctgcggggcc tgttctggta tagacaggat    180

cccggcaagg gccctgagtt cctgtttacc ctgtactccg ccggcgagga gaaggagaag    240

gagagactga aggccaccct gacaaagaag gagtcttttc tgcacatcac agccccaaag    300

cccgaggaca gcgccaccta tctgtgcgcc gtgcggatga acacaggctt ccagaagctg    360

gtgtttggca ccggcacaag actgctggtg agcccaaaca tccagaatcc tgagccagcc    420

gtgtaccagc tgaaggaccc ccggtcccag gattctaccc tgtgcctgtt cacagacttt    480

gatagccaga tcaacgtgcc caagacaatg gagtccggca ccttcatcac agacaagtgc    540

gtgctggaca tgaaggctat ggactctaag agcaacggcg ccatcgcctg gtctaatcag    600

accagcttca catgccagga tatctttaag gagaccaatg ccacataccc aagctccgac    660

gtgccctgtg atgccaccct gacagagaag agcttcgaga ccgacatgaa cctgaatttt    720

cagaacctgc tggtcatcgt gctgaggatc ctgctgctga aggtggccgg ctttaatctg    780

ctgatgacac tgcgcctgtg gtctagctga tga                                 813


<210> SEQ ID NO 90
<211> LENGTH: 927
<212> TYPE: DNA
<213> ORGANISM: Homo sapiens

<400> SEQUENCE: 90

atgactatca ggctcctctg ctacatgggc ttttattttc tgggggcagg cctcatggaa     60

gctgacatct accagacccc aagatacctt gttataggga caggaaagaa gatcactctg    120

gaatgttctc aaaccatggg ccatgacaaa atgtactggt atcaacaaga tccaggaatg    180

gaactacacc tcatccacta ttcctatgga gttaattcca cagagaaggg agatctttcc    240

tctgagtcaa cagtctccag aataaggacg gagcattttc ccctgaccct ggagtctgcc    300

aggccctcac atacctctca gtacctctgt gccagcagtc cgccgggaca gccttacgag    360

cagtacttcg ggccgggcac caggctcacg gtcacagagg acctgaacaa ggtgttccca    420

cccgaggtcg ctgtgtttga gccatcagaa gcagagatct cccacaccca aaaggccaca    480

ctggtgtgcc tggccacagg cttcttcccc gaccacgtgg agctgagctg gtgggtgaat    540

gggaaggagg tgcacagtgg ggtcagcacg gacccgcagc ccctcaagga gcagcccgcc    600

ctcaatgact ccagatactg cctgagcagc cgcctgaggg tctcggccac cttctggcag    660

aacccccgca accacttccg ctgtcaagtc cagttctacg ggctctcgga gaatgacgag    720

tggacccagg atagggccaa acccgtcacc cagatcgtca gcgccgaggc ctggggtaga    780

gcagactgtg gctttacctc ggtgtcctac cagcaagggg tcctgtctgc caccatcctc    840

tatgagatcc tgctagggaa ggccaccctg tatgctgtgc tggtcagcgc ccttgtgttg    900
```

atggccatgg tcaagagaaa ggatttc 927

<210> SEQ ID NO 91
<211> LENGTH: 825
<212> TYPE: DNA
<213> ORGANISM: Homo sapiens

<400> SEQUENCE: 91
atggagaaaa tgttggagtg tgcattcata gtcttgtggc ttcagcttgg ctggttgagt 60
ggagaagacc aggtgacgca gagtcccgag gccctgagac tccaggaggg agagagtagc 120
agtctcaact gcagttacac agtcagcggt ttaagagggc tgttctggta taggcaagat 180
cctgggaaag gccctgaatt cctcttcacc ctgtattcag ctggggaaga aaaggagaaa 240
gaaaggctaa aagccacatt aacaaagaag gaaagctttc tgcacatcac agcccctaaa 300
cctgaagact cagccactta tctctgtgct gtgcggatga acacaggctt tcagaaactt 360
gtatttggaa ctggcacccg acttctggtc agtccaaata tccagaaccc tgaccctgcc 420
gtgtaccagc tgagagactc taaatccagt gacaagtctg tctgcctatt caccgatttt 480
gattctcaaa caaatgtgtc acaaagtaag gattctgatg tgtatatcac agacaaaact 540
gtgctagaca tgaggtctat ggacttcaag agcaacagtg ctgtggcctg gagcaacaaa 600
tctgactttg catgtgcaaa cgccttcaac aacagcatta ttccagaaga caccttcttc 660
cccagcccag aaagttcctg tgatgtcaag ctggtcgaga aaagctttga aacagatacg 720
aacctaaact ttcaaaacct gtcagtgatt gggttccgaa tcctcctcct gaaagtggcc 780
gggtttaatc tgctcatgac gctgcggctg tggtccagct gatga 825

<210> SEQ ID NO 92
<211> LENGTH: 927
<212> TYPE: DNA
<213> ORGANISM: Artificial
<220> FEATURE:
<223> OTHER INFORMATION: Synthetic oligonucleotide

<400> SEQUENCE: 92
atgaccatcc ggctgctgtg ctacatgggc ttctattttc tgggcgccgg cctgatggag 60
gccgatatct accagacccc cagatacctg gtcatcggca ccggcaagaa gatcacactg 120
gagtgttccc agacaatggg ccacgataag atgtactggt atcagcagga ccctggcatg 180
gagctgcacc tgatccacta ctcctatggc gtgaactcta ccgagaaggg cgacctgagc 240
tccgagtcca ccgtgtctcg gatcagaaca gagcacttcc cactgaccct ggagagcgcc 300
aggcctagcc acacatccca gtacctgtgc gcctctagcc cacctggaca gccttacgag 360
cagtatttcg gcccaggcac caggctgacc gtgacagagg acctgaataa ggtgttcccc 420
cctgaggtgg ccgtgtttga gccttccgag gccgagatct ctcacaccca gaaggccacc 480
ctggtgtgcc tggcaaccgg cttctttcca gatcacgtgg agctgagctg gtgggtgaac 540
ggcaaggagg tgcacagcgg cgtgtccacc gacccacagc ccctgaagga gcagcccgcc 600
ctgaatgata gcagatattg cctgtctagc cggctgagag tgtccgccac cttttggcag 660
aaccctcgga atcacttcag atgtcaggtg cagttttacg gcctgagcga gaatgacgag 720
tggacccagg atagggccaa gcccgtgaca cagatcgtgt ccgccgaggc atggggaagg 780
gcagactgcg gcttcacatc cgtgtcttat cagcagggcg tgctgagcgc caccatcctg 840
tatgagatcc tgctgggcaa ggccacactg tacgccgtgc tggtgtccgc cctggtgctg 900
atggctatgg tgaagcggaa ggacttt 927

<210> SEQ ID NO 93
<211> LENGTH: 754
<212> TYPE: DNA
<213> ORGANISM: Artificial
<220> FEATURE:
<223> OTHER INFORMATION: Synthetic oligonucleotide

<400> SEQUENCE: 93
ggtgacccag agcccagagg ccctgaggct gcaggaggga gagagctcct ctctgaattg 60
tagctacaca gtgtccggcc tgcggggcct gttctggtat agacaggatc ccggcaaggg 120
ccctgagttc ctgtttaccc tgtactccgc cggcgaggag aaggagaagg agagactgaa 180
ggccaccctg acaaagaagg agtcttttct gcacatcaca gccccaaagc ccgaggacag 240
cgccacctat ctgtgcgccg tgcggatgaa cacaggcttc cagaagctgg tgtttggcac 300
cggcacaaga ctgctggtga gcccaaacat ccagaatccc gaccctgccg tgtatcagct 360
gagggactcc aagtcctctg ataagagcgt gtgcctgttc accgactttg attctcagac 420
aaacgtgagc cagtccaagg acagcgacgt gtacatcacc gacaagacag tgctggatat 480
gcggagcatg gacttcaagt ctaacagcgc cgtggcctgg agcaataagt ccgatttcgc 540
ctgcgccaat gcctttaaca attccatcat ccctgaggat accttctttc catctcccga 600
gagctcctgt gacgtgaagc tggtggagaa gtctttcgag accgatacaa acctgaattt 660
tcagaacctg agcgtgatcg gcttccggat cctgctgctg aaggtggccg gcttcaatct 720
gctgatgaca ctgagactgt ggtctagctg atga 754

<210> SEQ ID NO 94
<211> LENGTH: 28
<212> TYPE: PRT
<213> ORGANISM: Artificial
<220> FEATURE:
<223> OTHER INFORMATION: Synthetic polypeptide

<400> SEQUENCE: 94

```
Asn Ile Lys Ile Leu Glu Asp Glu Pro Pro Thr Val Arg Met Arg Pro
1               5                   10                  15

His Cys Val Pro Phe Trp Thr Gly Arg Ile Leu Leu
            20                  25
```

<210> SEQ ID NO 95
<211> LENGTH: 27
<212> TYPE: PRT
<213> ORGANISM: Porcine teschovirus-1

<400> SEQUENCE: 95

```
Arg Ala Lys Arg Ser Gly Ser Gly Ala Thr Asn Phe Ser Leu Leu Lys
1               5                   10                  15

Gln Ala Gly Asp Val Glu Glu Asn Pro Gly Pro
            20                  25
```

T CELL RECEPTORS TARGETING DEFECTIVE DNA REPAIR PROTEINS

CLAIM OF PRIORITY

This application is a national stage application under 35 U.S.C. § 371 of International Application No. PCT/US2021/016883, having an international filing date of Feb. 5, 2021, which claims priority to U.S. Provisional Application No. 62/971,057, filed on Feb. 6, 2020, the entire contents of which is hereby incorporated by reference.

SEQUENCE LISTING

This document contains a sequence listing that has been submitted electronically as an ASCII text file. The ASCII text file, created on Apr. 7, 2022, is 110 kilobytes in size. The material in the ASCII text file is hereby incorporated by reference in its entirety.

BACKGROUND

1. Technical Field

This document relates to isolated immune cells that include an exogenous T cell receptor (TCR) having affinity for an Ataxia-Telangiesctasia Mutated (ATM) peptide and/or an exogenous TCR having affinity for an AT-rich interactive domain-containing protein 1A (ARID1A) peptide, as well as methods and materials for making such immune cells. For example, this document provides isolated immune cells that included an exogenous TCR having affinity for a mutant ATM peptide and/or an exogenous TCR having affinity for a mutant ARID1A peptide, methods and materials for making such immune cells, and methods and materials for using such immune cells to treat mammals (e.g., a human having cancer).

2. Background Information

Defective DNA repair is a hallmark of cancer and results in genomic instability and accumulation of other genetic abnormalities. Ataxia-Telangiesctasia Mutated (ATM) is a PI3K-related serine/threonine protein kinase (PIKK) that plays a role in the repair of DNA double-strand breaks. The PIKK domain of ATM recognizes serine-glutamine and threonine-glutamine motifs of many proteins, including ones involved in cell-cycle checkpoint arrest (e.g., Chk1 and Chk2), DNA repair (BRCA1 and RAD51), and apoptosis (p53). See, e.g., Choi, et al., *Mol. Cancer Ther.,* 15(8):1781-91 (2016). The AT-rich interactive domain-containing protein 1A (ARID1A, also known as BAF250a) is a subunit of the SWI/SNF chromatin remodeling complex, which helps regulate gene transcription by changing chromatin structure. See, Bitler, et al., *Nat. Cell Biol.,* 19(8):962-973 (2019). The gene encoding ATM and the gene encoding ARID1A are frequently mutated in a wide variety of cancers including ovarian, endometrial, kidney, pancreas, stomach, bladder, lung, breast, brain, and hematological malignancies.

SUMMARY

This document is based, at least in part, on the discoveries of TCRs having affinity for an ATM (Ataxia-Telangiesctasia Mutated) peptide, e.g., a mutant ATM peptide, and TCRs having affinity for an ARID1A (AT-rich interactive domain-containing protein 1A) peptide, e.g., a mutant ARID1A peptide. As described herein, TCRs provided herein have an alpha chain and a beta chain. In some cases, a TCR provided herein can bind to a mutant ATM peptide (within the context of an MHC molecule such as HLA A*03:01). In some cases, a TCR provided herein can bind to a mutant ARID1A peptide (within the context of an MHC molecule such as HLA A*02:01).

In some cases, a TCR provided herein that has affinity for an ATM peptide can have an alpha chain that includes (i) the amino acid sequences set forth in SEQ ID NO:10, SEQ ID NO:11, and SEQ ID NO:12, or (ii) the amino acid sequences set forth in SEQ ID NO:10 and SEQ ID NO:11 with no more than one amino acid modification, and the amino acid sequence set forth in SEQ ID NO:12 with no more than two amino acid modifications, and a beta chain that includes (i) the amino acid sequences set forth in SEQ ID NO:1, SEQ ID NO:2, and SEQ ID NO:3, or (ii) the amino acid sequences set forth in SEQ ID NO:1 and SEQ ID NO:2 with no more than one amino acid modification, and the amino acid sequence set forth in SEQ ID NO:3 with no more than two amino acid modifications. The amino acid modifications can be an amino acid substitution, an amino acid deletion, or an amino acid addition.

In some cases, a TCR provided herein that has affinity for an ARID1A peptide can have an alpha chain that includes (i) the amino acid sequences set forth in SEQ ID NO:32, SEQ ID NO:33, and SEQ ID NO:34, or (ii) the amino acid sequences set forth in SEQ ID NO:32 and SEQ ID NO:33 with no more than one amino acid modification and the amino acid sequence set forth in SEQ ID NO:34 with no more than two amino acid modifications, and an beta chain that includes (i) the amino acid sequences set forth in SEQ ID NO:23, SEQ ID NO:24, and SEQ ID NO:25, or (ii) the amino acid sequences set forth in SEQ ID NO:23 and SEQ ID NO:24 with no more than one amino acid modification, and the amino acid sequence set forth in SEQ ID NO:25 with no more than two amino acid modifications. The amino acid modifications can be an amino acid substitution, an amino acid deletion, or an amino acid addition.

Immune cells (e.g., T cells) modified to include an exogenous TCR having affinity for an ATM peptide (e.g., a mutant ATM peptide), an exogenous TCR having affinity for an ARID1A peptide (e.g., a mutant ARID1A peptide), or both an exogenous TCR having affinity for an ATM peptide (e.g., a mutant ATM peptide) and an exogenous TCR having affinity for an ARID1A peptide (e.g., a mutant ARID1A peptide) as described herein can be used to treat a mammal having cancer. Mutations in ATM and ARID1A are commonly found, for example, in ovarian, endometrial, kidney, pancreas, gastric, bladder, lung, breast, brain, liver, cervical, uterine, prostate, or hematopoietic malignancies.

In one aspect, this document features an isolated immune cell (e.g., a T cell) comprising an exogenous TCR having affinity for an ATM peptide (e.g., a mutant ATM peptide comprising a valine, alanine, cysteine, or serine at the position corresponding to 2695 in the human ATM protein). The exogenous TCR includes an alpha chain and a beta chain, where the alpha chain includes (i) the amino acid sequences set forth in SEQ ID NO:10, SEQ ID NO:11, and SEQ ID NO:12, or (ii) the amino acid sequences set forth in SEQ ID NO:10 and SEQ ID NO:11 with no more than one amino acid modification and the amino acid sequence set forth in SEQ ID NO:12 with no more than two amino acid modifications, wherein the amino acid modifications are selected from the group consisting of amino acid substitutions, amino acid deletions, and amino acid additions, and the beta chain includes (i) the amino acid sequences set forth in SEQ ID NO:1, SEQ ID NO:2, and SEQ ID NO:3, or (ii) the amino acid sequences set forth in SEQ ID NO:1 and SEQ ID NO:2 with no more than one amino acid modification and the amino acid sequence set forth in SEQ ID NO:3 with no more than two amino acid modifications, wherein the amino acid modifications are selected from the group consisting of amino acid substitutions, amino acid deletions, and amino acid additions.

In some cases, the alpha chain includes an amino sequence having at least 80 percent identity, at least 90 percent identity, or at least 95 percent identity to the amino acid sequence set forth in SEQ ID NO:18 or SEQ ID NO:22. In some cases, the alpha chain comprises the amino acid sequence set forth in SEQ ID NO:10. In some cases, the alpha chain includes the amino acid sequence set forth in SEQ ID NO:11. In some cases, the alpha chain includes the amino acid sequence set forth in SEQ ID NO:12. In some cases, the alpha chain includes the amino acid sequence set forth in SEQ ID NO:10, SEQ ID NO: 11, and SEQ ID NO:12.

In some cases, the beta chain includes an amino acid sequence having at least 80 percent identity, at least 90 percent identity, or at least 95 percent identity to the amino acid sequence set forth in SEQ ID NO:9 or SEQ ID NO:20. In some cases, the beta chain includes the amino acid sequence set forth in SEQ ID NO:1. In some cases, the beta chain includes the amino acid sequence set forth in SEQ ID NO:2. In some cases, the beta chain includes the amino acid sequence set forth in SEQ ID NO:3. In some cases, the beta chain comprises the amino acid sequence set forth in SEQ ID NO:1, SEQ ID NO: 2 and SEQ ID NO:3.

In one aspect, this document features an isolated immune cell (e.g., a T cell) comprising an exogenous TCR having affinity for an ARID1A peptide (e.g., a mutant ARID1A peptide containing a frameshift at the position corresponding to 1960 in the human ARID1A protein). The exogenous TCR includes an alpha chain and a beta chain, where the alpha chain includes (i) the amino acid sequences set forth in SEQ ID NO:32, SEQ ID NO:33, and SEQ ID NO:34, or (ii) the amino acid sequences set forth in SEQ ID NO:32 and SEQ ID NO:33 with no more than one amino acid modification and the amino acid sequence set forth in SEQ ID NO:34 with no more than two amino acid modifications, wherein the amino acid modifications are selected from the group consisting of amino acid substitutions, amino acid deletions, and amino acid additions, and the beta chain includes (i) the amino acid sequences set forth in SEQ ID NO:23, SEQ ID NO:24, and SEQ ID NO:25, or (ii) the amino acid sequences set forth in SEQ ID NO:23 and SEQ ID NO:24 with no more than one amino acid modification and the amino acid sequence set forth in SEQ ID NO:25 with no more than two amino acid modifications, wherein the amino acid modifications are selected from the group consisting of amino acid substitutions, amino acid deletions, and amino acid additions.

In some cases, the alpha chain includes an amino sequence having at least 80 percent identity, at least 90 percent identity, or at least 95 percent identity to the amino acid sequence set forth in SEQ ID NO:40 or SEQ ID NO:44. In some cases, the alpha chain includes the amino acid sequence set forth in SEQ ID NO:32. In some cases, the alpha chain includes the amino acid sequence set forth in SEQ ID NO:33. In some cases, the alpha chain includes the amino acid sequence set forth in SEQ ID NO:34. In some cases, the alpha chain includes the amino acid sequence set forth in SEQ ID NO:32, SEQ ID NO:33, and SEQ ID NO:34.

In some cases, the beta chain includes an amino acid sequence having at least 80 percent identity, at least 90 percent identity, or at least 95 percent identity to the amino acid sequence set forth in SEQ ID NO:31 or SEQ ID NO:42. In some cases, the beta chain includes the amino acid sequence set forth in SEQ ID NO:23. In some cases, the beta chain includes the amino acid sequence set forth in SEQ ID NO:24. In some cases, the beta chain includes the amino acid sequence set forth in SEQ ID NO:25. In some cases, the beta chain includes the amino acid sequence set forth in SEQ ID NO:23, SEQ ID NO: 24 and SEQ ID NO:25.

In any of the embodiments, the immune cell can be a T cell. Expression of the endogenous TCR alpha and beta chain coding sequences can be downregulated in the T cell.

This document also features a nucleic acid molecule that includes a nucleic acid sequence encoding an alpha chain of a TCR having affinity for an ATM peptide and a nucleic acid sequence encoding a beta chain of the TCR. In some cases, the alpha chain includes (i) the amino acid sequences set forth in SEQ ID NO:10, SEQ ID NO:11, and SEQ ID NO:12, or (ii) the amino acid sequences set forth in SEQ ID NO:10 and SEQ ID NO:11 with no more than one amino acid modification and the amino acid sequence set forth in SEQ ID NO:12 with no more than two amino acid modifications, wherein the amino acid modifications are selected from the group consisting of amino acid substitutions, amino acid deletions, and amino acid additions, and the beta chain includes (i) the amino acid sequences set forth in SEQ ID NO:1, SEQ ID NO:2, and SEQ ID NO:3, or (ii) the amino acid sequences set forth in SEQ ID NO:1 and SEQ ID NO:2 with no more than one amino acid modification and the amino acid sequence set forth in SEQ ID NO:3 with no more than two amino acid modifications, wherein the amino acid modifications are selected from the group consisting of amino acid substitutions, amino acid deletions, and amino acid additions.

In some cases, the alpha chain comprises an amino sequence having at least 80 percent identity, at least 90 percent identity, or at least 95 percent identity to the amino acid sequence set forth in SEQ ID NO:18 or SEQ ID NO:22. In some cases, the alpha chain includes the amino acid sequence set forth in SEQ ID NO:10. In some cases, the alpha chain includes the amino acid sequence set forth in SEQ ID NO:11. In some cases, the alpha chain includes the amino acid sequence set forth in SEQ ID NO:12. In some cases, the alpha chain includes the amino acid sequence set forth in SEQ ID NO:10, SEQ ID NO: 11, and SEQ ID NO:12. In some cases, the beta chain comprises an amino acid sequence having at least 80 percent identity, at least 90 percent identity, or at least 95 percent identity to the amino acid sequence set forth in SEQ ID NO:9 or SEQ ID NO:20. In some cases, the beta chain includes the amino acid sequence set forth in SEQ ID NO:1. In some cases, the beta chain includes the amino acid sequence set forth in SEQ ID NO:2. In some cases, the beta chain includes the amino acid sequence set forth in SEQ ID NO:3. In some cases, the beta chain comprises the amino acid sequence set forth in SEQ ID NO:1, SEQ ID NO: 2 and SEQ ID NO:3.

This document also features a nucleic acid molecule that includes a nucleic acid sequence encoding an alpha chain of a TCR having affinity for an ARID1A peptide and a nucleic acid sequence encoding a beta chain of the TCR. In some cases, the alpha chain includes (i) the amino acid sequences set forth in SEQ ID NO:32, SEQ ID NO:33, and SEQ ID NO:34, or (ii) the amino acid sequences set forth in SEQ ID NO:32 and SEQ ID NO:33 with no more than one amino acid modification and the amino acid sequence set forth in SEQ ID NO:34 with no more than two amino acid modifications, wherein the amino acid modifications are selected from the group consisting of amino acid substitutions, amino acid deletions, and amino acid additions; and the beta chain includes (i) the amino acid sequences set forth in SEQ ID NO:23, SEQ ID NO:24, and SEQ ID NO:25, or (ii) the amino acid sequences set forth in SEQ ID NO:23 and SEQ ID NO:24 with no more than one amino acid modification and the amino acid sequence set forth in SEQ ID NO:25 with no more than two amino acid modifications, wherein the amino acid modifications are selected from the group consisting of amino acid substitutions, amino acid deletions, and amino acid additions.

In some cases, the alpha chain includes an amino sequence having at least 80 percent identity, at least 90 percent identity, or at least 95 percent identity to the amino acid sequence set forth in SEQ ID NO:40 or SEQ ID NO:44. In some cases, the alpha chain includes the amino acid sequence set forth in SEQ ID NO:32. In some cases, the alpha chain includes the amino acid sequence set forth in SEQ ID NO:33. In some cases, the alpha chain includes the amino acid sequence set forth in SEQ ID NO:34. In some cases, the alpha chain includes the amino acid sequence set forth in SEQ ID NO:32, SEQ ID NO:33, and SEQ ID NO:34. In some cases, the beta chain includes an amino acid sequence having at least 80 percent identity, at least 90 percent identity, or at least 95 percent identity to the amino acid sequence set forth in SEQ ID NO:31 or SEQ ID NO:42. In some cases, the beta chain includes the amino acid sequence set forth in SEQ ID NO:23. In some cases, the beta chain includes the amino acid sequence set forth in SEQ ID NO:24. In some cases, the beta chain includes the amino acid sequence set forth in SEQ ID NO:25. In some cases, the beta chain includes the amino acid sequence set forth in SEQ ID NO:23, SEQ ID NO:24 and SEQ ID NO:25.

In any of the embodiments, the nucleic acid can include a promotor 5' of the nucleic acid sequence encoding the alpha chain and/or can include a promoter 5' of the nucleic acid sequence encoding the beta chain. The promoter can be a viral 5' long terminal repeat or a viral 3' long terminal repeat.

In any of the embodiments, the nucleic acid can be a vector, e.g., a viral vector such as a retroviral vector or a lentiviral vector.

In any of the embodiments, the nucleic acid further can include a nucleic acid sequence encoding a linker. In some cases, the linker can be 3' of the nucleic acid sequence encoding the alpha chain and 5' of the nucleic acid sequence encoding the beta chain. In some cases, the linker can be 3' of the nucleic acid sequence encoding the beta chain and 5' of the nucleic acid sequence encoding the alpha chain. In some cases, the linker is a self-cleaving peptide (e.g., a self-cleaving peptide of a foot-and-mouth disease virus (FMDV), an equine rhinitis A virus (ERAVO, a *Thosea asigna* virus (TaV), or a porcine tescho virus-1 (PTV-1)). In some cases, the self-cleaving peptide is a P2A peptide. In some cases, the linker includes a furin cleavage site.

This document also features a method of making an immune cell (e.g., a T cell) that includes an exogenous TCR having affinity for an ATM peptide and/or an exogenous TCR having affinity an ARID1A peptide. The method includes introducing, into the immune cell, a nucleic acid molecule that includes a nucleic acid sequence encoding an alpha chain of a TCR having affinity for an ATM peptide and a nucleic acid sequence encoding a beta chain of the TCR, and/or introducing a nucleic acid molecule that includes a nucleic acid sequence encoding an alpha chain of a TCR having affinity for an ARID1A peptide and a nucleic acid sequence encoding a beta chain of the TCR, wherein the exogenous TCR having affinity for the ATM peptide and/or the exogenous TCR having affinity for the ARID1A peptide is expressed from the nucleic acid in the immune cell.

In another aspect, this document features an isolated immune cell that includes a nucleic acid molecule and includes an exogenous TCR having affinity for an ATM peptide and/or an exogenous TCR having affinity for an ARID1A peptide. The nucleic acid molecule includes a nucleic acid sequence encoding an alpha chain of a TCR having affinity for an ATM peptide and a nucleic acid sequence encoding a beta chain of the TCR, and/or a nucleic acid sequence encoding an alpha chain of a TCR having affinity for an ARID1A peptide and a nucleic acid sequence encoding a beta chain of the TCR.

This document also features a population of cells that include at least one isolated immune cell, where the isolated immune cell includes a nucleic acid molecule and includes an exogenous TCR having affinity for an ATM peptide and/or an exogenous TCR having affinity for an ARID1A peptide. This document also features a pharmaceutical composition that includes the population of cells and a pharmaceutically acceptable carrier. A method for treating a mammal (e.g., a human) in need thereof also is provided that includes administering to the mammal an effective amount of the pharmaceutical composition. The mammal can have cancer (e.g., a cancer selected from the group consisting of melanoma, chronic lymphocytic leukemia, a myelodysplastic syndrome, and breast cancer). The immune cells can be autologous to the mammal.

In another aspect, this document features a method for providing a mammal (e.g., a human) with immune cells that include an exogenous TCR having affinity for an ATM peptide and/or an exogenous TCR having affinity for an ARID1A peptide. The method includes administering, to the mammal, the population of cells. The mammal can have cancer (e.g., ovarian, endometrial, kidney, pancreas, gastric, bladder, lung, breast, brain, liver, cervical, uterine, prostate, or a hematopoietic malignancy). The immune cells can be autologous to the mammal.

A method for providing a mammal (e.g., a human) with cells comprising a TCR having affinity for an ATM peptide and/or ARID1A peptide also is provided. The method includes delivering, to the mammal, a nucleic acid molecule that includes a nucleic acid sequence encoding an alpha chain of a TCR having affinity for an ATM peptide and a nucleic acid sequence encoding a beta chain of the TCR, and/or a nucleic acid sequence encoding an alpha chain of a TCR having affinity for an ARID1A peptide and a nucleic acid sequence encoding a beta chain of the TCR, wherein the nucleic acid is expressed in cells of the mammal. The mammal can have cancer (e.g., ovarian, endometrial, kidney, pancreas, gastric, bladder, lung, breast, brain, liver, cervical, uterine, prostate, or a hematopoietic malignancy). The immune cells can be autologous to the mammal.

In another aspect, this document features a method for treating a mammal (e.g., a human) having cancer. The method includes administering, to the mammal, a population of cells that include at least one isolated immune cell, where the isolated immune cell includes a nucleic acid molecule and includes an exogenous TCR having affinity for an ATM peptide and/or an exogenous TCR having affinity for an ARID1A peptide, or administering a nucleic acid molecule that includes a nucleic acid sequence encoding an alpha chain of a TCR having affinity for an ATM peptide and a nucleic acid sequence encoding a beta chain of the TCR, and/or a nucleic acid sequence encoding an alpha chain of a TCR having affinity for an ARID1A peptide and a nucleic acid sequence encoding a beta chain of the TCR. The immune cells can be autologous to the mammal.

Unless otherwise defined, all technical and scientific terms used herein have the same meaning as commonly understood by one of ordinary skill in the art to which this disclosure pertains. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A contains an alignment of mutant ATM peptides containing either a valine, alanine, cysteine, or serine at the position corresponding to 2695 (SEQ ID NOs:61-64) in the human ATM protein and a wild-type ATM peptide containing a glycine at the position corresponding to 2695 (SEQ ID NO:65) in the human ATM protein (NCBI Reference Sequence: NP_000042.3).

FIG. 1B contains an alignment of a mutant ARID1A peptide containing a frameshift at the position corresponding to 1960 (1960fs) (SEQ ID NO:66) in the human ARID1A protein and a wild-type ARID1A peptide containing a histidine at the position corresponding to 1960 (SEQ ID NO:67) in the human ARID1A protein (NCBI Reference Sequence: NP_006006.3).

FIG. 1C contains the nucleotide sequence encoding the TRBV9*01+TRAV14/DV4 chimeric TCR (SEQ ID NO:49) and the amino acid sequence of the TRBV9*01+TRAV14/DV4 chimeric TCR (SEQ ID NO:50).

FIG. 2 contains an exemplary codon optimized nucleotide sequence encoding the TRBV9*01+TRAV14/DV4 chimeric TCR (SEQ ID NO:51) and the amino acid sequence of the TRBV9*01+TRAV14/DV4 chimeric TCR (SEQ ID NO:50).

FIG. 3 contains the nucleotide sequence encoding a human TRBV9*01+TRAV14/DV4 TCR (SEQ ID NO:52) and the amino acid sequence of the human TRBV9*01+TRAV14/DV4 TCR (SEQ ID NO:53).

FIG. 4 contains an exemplary codon optimized nucleotide sequence encoding the human TRBV9*01+TRAV14/DV4 TCR (SEQ ID NO:54) and the amino acid sequence of the human TRBV9*01+TRAV14/DV4 TCR (SEQ ID NO:53).

FIG. 5 contains the nucleotide sequence encoding a TRBV25-1+TRAV20 chimeric TCR (SEQ ID NO:55) and the amino acid sequence of the TRBV25-1+TRAV20 chimeric TCR (SEQ ID NO:56).

FIG. 6 contains an exemplary codon optimized nucleotide sequence encoding the TRBV25-1+TRAV20 chimeric TCR (SEQ ID NO:57) and the amino acid sequence of the TRBV25-1+TRAV20 chimeric TCR (SEQ ID NO:56).

FIG. 7 contains the nucleotide sequence encoding the human TRBV25-1+TRAV20 (SEQ ID NO:58) TCR and the amino acid sequence of the human TRBV25-1+TRAV20 TCR (SEQ ID NO:59).

FIG. 8 contains an exemplary codon optimized nucleotide sequence encoding a human TRBV25-1+TRAV20 TCR (SEQ ID NO:60) and the amino acid sequence of the human TRBV25-1+TRAV20 TCR (SEQ ID NO:59).

FIG. 10 contains the amino acid sequences set forth in Table 3.

FIG. 11A contains the nucleotide sequence encoding the beta chain of TRBV9*01+TRAV14/DV4 chimeric TCR, with human beta variable region in larger font, CDR1, CDR2, CDR3 underlined, and mouse beta constant in italics (SEQ ID NO:78).

FIG. 11B contains the nucleotide sequence encoding the alpha chain of TRBV9*01+TRAV14/DV4 chimeric TCR, with human alpha variable region in larger font, CDR1, CDR2, CDR3 underlined, and mouse alpha constant in italics (SEQ ID NO:79).

FIG. 12A contains the codon optimized nucleotide sequence encoding the beta chain of TRBV9*01+TRAV14/DV4 chimeric TCR, with human beta variable region in larger font, CDR1, CDR2, CDR3 underlined, and mouse beta constant in italics (SEQ ID NO:80).

FIG. 12B contains the codon optimized nucleotide sequence encoding the alpha chain of TRBV9*01+TRAV14/DV4 chimeric TCR, with human alpha variable region in larger font, CDR1, CDR2, CDR3 underlined, and mouse alpha constant in italics (SEQ ID NO:81).

FIG. 13A contains the nucleotide sequence encoding the beta chain of TRBV9*01+TRAV14/DV4 human TCR, with human beta variable region in larger font, CDR1, CDR2, CDR3 underlined, and human beta constant in italics (SEQ ID NO:82).

FIG. 13B contains the nucleotide sequence encoding the alpha chain of TRBV9*01+TRAV14/DV4 human TCR, with human alpha variable region in larger font, CDR1, CDR2, CDR3 underlined, and human alpha constant in italics (SEQ ID NO:83).

FIG. 14A contains the codon optimized nucleotide sequence encoding the beta chain of TRBV9*01+TRAV14/DV4 human TCR, with human beta variable region in larger font, CDR1, CDR2, CDR3 underlined, and human beta constant in italics (SEQ ID NO:84).

FIG. 14B contains the codon optimized nucleotide sequence encoding the alpha chain of TRBV9*01+TRAV14/DV4 human TCR, with human alpha variable region in larger font, CDR1, CDR2, CDR3 underlined, and human alpha constant in italics (SEQ ID NO:85).

FIG. 15A contains the nucleotide sequence encoding the beta chain of TRBV25-1+TRAV20 chimeric TCR with human beta variable region in larger font, CDR1, CDR2, CDR3 underlined, and mouse beta constant (codon optimized) in italics (SEQ ID NO:86).

FIG. 15B contains the nucleotide sequence encoding the alpha chain of TRBV25-1+TRAV20 chimeric TCR, with the human variable region in larger font, CDR1, CDR2, CDR3 underlined, and mouse alpha constant (codon optimized) in italics (SEQ ID NO:87).

FIG. 16A contains the codon optimized nucleotide sequence encoding the beta chain of TRBV25-1+TRAV20 chimeric TCR, with human variable region in larger font, CDR1, CDR2, CDR3 underlined, and mouse beta constant in italics (SEQ ID NO:88).

FIG. 16B contains the codon optimized nucleotide sequence encoding the alpha chain of TRBV25-1+TRAV20 chimeric TCR, with human variable region in larger font, CDR1, CDR2, CDR3 underlined, and mouse alpha constant in italics (SEQ ID NO:89).

FIG. 17A contains the nucleotide sequence encoding the beta chain of TRBV25-1+TRAV20 human TCR, with human variable region in larger font, CDR1, CDR2, CDR3 underlined, and human beta constant in italics (SEQ ID NO:90).

FIG. 17B contains the nucleotide sequence encoding the alpha chain of TRBV25-1+TRAV20 human TCR, with human variable region in larger font, CDR1, CDR2, CDR3 underlined, and human alpha constant in italics (SEQ ID NO:91).

FIG. 18A contains the codon-optimized nucleotide sequence encoding the beta chain of TRBV25-1+TRAV20 human TCR, with human variable region in larger font, CDR1, CDR2, CDR3 underlined, and human beta constant in italics (SEQ ID NO:92).

FIG. 18B contains the codon-optimized nucleotide sequence encoding the alpha chain of TRBV25-1+TRAV20 human TCR, with the human variable region in larger font, CDR1, CDR2, CDR3 underlined, and human alpha constant in italics (SEQ ID NO:93).

DETAILED DESCRIPTION

Figure 9A:
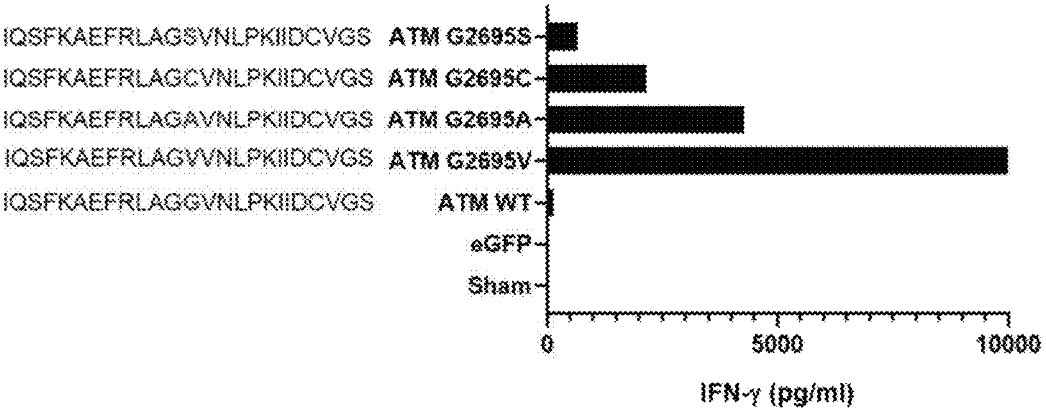
FIG. 9A contains a graph of interferon gamma (IFNγ) (pg/mL) in the supernatant after TCR-transduced T cells were co-cultured overnight with dendritic cells expressing wildtype (wt) ATM or mutated forms of ATM (G2695V, G2695A, G2695C, or G2695S).

In one aspect, this document provides TCRs having affinity for an ATM peptide, e.g., a mutant ATM peptide (within the context of an MHC molecule presenting that ATM peptide). In another aspect, this document provides TCRs having affinity for an ARID1A peptide, e.g., a mutant ARID1A peptide (within the context of an MHC molecule presenting that ARID1A peptide). The amino acid sequence of human ATM is set forth in NCBI Reference Sequence: NP_000042.3 or UniProt KB-Q13315 (ATM_HUMAN), and the amino acid sequence of human ARID1A is set forth in NCBI Reference Sequence: NP_006006.3 or UniProtKB-O14497 (ARI1A HUMAN). See also Gene ID 472 for the human ATM gene and Gene ID 8289 for the human ARID1A gene. Mutations in ATM and ARID1A are commonly found, for example, in ovarian, endometrial, kidney, pancreas, gastric, bladder, lung, breast, brain, liver, cervical, uterine, prostate, and hematopoietic malignancies.

In some cases, a TCR provided herein can have specific affinity for a mutant ATM peptide (e.g., a mutant ATM peptide comprising a valine at the position corresponding to 2695 in the human ATM protein) within the context of an MHC molecule (e.g., HLA A*03:01) presenting that ATM peptide. For example, a TCR provided herein, and cells expressing such a TCR (e.g., immune cells), can have reactivity against a mutant ATM peptide comprising a valine, alanine, cysteine, or serine at the position corresponding to 2695 in the human ATM protein without having reactivity to the wild-type of ATM (e.g., having a glycine at the position corresponding to 2695 in the human ATM protein). See FIG. 1A for an alignment of mutant ATM peptides comprising a valine, alanine, cysteine, or serine at the position corresponding to 2695 in the human ATM protein (SEQ ID NOs:61-64, respectively) and a wild-type ATM peptide (SEQ ID NO:65) having a glycine at the position corresponding to 2695 in the human ATM protein.

In some cases, a TCR provided herein can have specific affinity for a mutant ARID1A peptide (e.g., a mutant ARID1A peptide comprising a frameshift at the position corresponding to 1960 in the human ARID1A protein) within the context of an MHC molecule (e.g., HLA A*02:01) presenting that ARID1A peptide. For example, a TCR provided herein, and cells expressing such a TCR (e.g., immune cells), can have reactivity against a mutant ARID1A peptide comprising a frameshift at the position corresponding to 1960 in the human ARID1A protein without having reactivity to the wild-type of ARID1A (e.g., having a histidine at the position corresponding to 1960 in the human ARID1A protein). See FIG. 1B for an alignment of a mutant ARID1A peptide (SEQ ID NO:66) comprising a frameshift at the position corresponding to 1960 in the human ARID1A protein and a wild-type ARID1A peptide (SEQ ID NO:67) having a histidine at the position corresponding to 1960 in the human ARID1A protein.

A mutant ATM peptide or a mutant ARID1A peptide can be, for example, from 8 to 30 amino acids in length. Examples of mutant ATM peptides that can be recognized by a TCR provided herein are set forth in Table 1. Examples of mutant ARID1A peptides that can be recognized by a TCR provided herein are set forth in Table 2.

TABLE 1

Exemplary mutant ATM peptides

| Sequence | SEQ ID NO: |
|---|---|
| LAGVVNLPK | 61 |
| LAGAVNLPK | 62 |
| LAGCVNLPK | 63 |
| LAGSVNLPK | 64 |

TABLE 2

Exemplary mutant ARID1A peptide

| Sequence | SEQ ID NO: |
|---|---|
| ILEDEPPTVRMRPHC | 68 |
| KESSKFPFGISPAQSHRNIKILEDE PPTVRMRPHCVPFWTGRILLPSAAS VCPIPFEACHLCQAMTLRCPNTQGC CSSWAS | 66 |
| NIKILEDEPPTVRMRPHCVPFWTGR ILL | 94 |

In some cases, immune cells that include an exogenous TCR provided herein (e.g., a TCR having affinity for a mutant ATM peptide, a TCR having affinity for an ARID1A peptide, or both a TCR having affinity for a mutant ATM peptide and a TCR having affinity for an ARID1A peptide) can be used to treat mammals (e.g., humans having cancer) who harbor the same or similar ATM and/or ARID1A mutations. For example, immune cells that include an exogenous TCR provided herein can be used to treat a subject with a cancer such as ovarian, endometrial, kidney, pancreas, gastric, bladder, lung, breast, brain, liver, cervical, uterine, prostate, or a hematopoietic malignancy.

A TCR is a heterodimeric cell surface protein and is involved in mediating signal transduction. The extracellular portion of a native heterodimeric TCR includes two polypeptide chains, each of which has a membrane-proximal constant domain, and a membrane-distal variable domain. The variable domains contain highly polymorphic loops analogous to the complementarity determining regions (CDRs) of antibodies.

In general, the TCRs provided herein include an alpha chain polypeptide and a beta chain polypeptide, where the alpha chain and the beta chain each include three CDRs and a constant region. In some cases, the alpha chain polypeptide of a TCR having affinity for an ATM peptide (e.g., a mutant ATM peptide) can include a CDR1 having the amino acid sequence set forth in SEQ ID NO:10 (or a variant with one, two, or three amino acid modifications), a CDR2 having the amino acid sequence set forth in SEQ ID NO:11 (or a variant with one, two, or three amino acid modifications), and a CDR3 having the amino acid sequence set forth in SEQ ID NO:12 (or a variant with one, two, or three amino acid modifications), and the beta chain polypeptide can include a CDR1 having the amino acid sequence set forth in SEQ ID NO:1 (or a variant with one, two, or three amino acid modifications), a CDR2 having the amino acid sequence set forth in SEQ ID NO:2 (or a variant with one, two, or three amino acid modifications), and a CDR3 having the amino acid sequence set forth in SEQ ID NO:3 (or a variant with one, two, or three amino acid modifications).

In some cases, the alpha chain polypeptide of a TCR having affinity for an ARID1A peptide (e.g., a mutant ARID1A peptide) can include a CDR1 having the amino acid sequence set forth in SEQ ID NO:32 (or a variant with one, two, or three amino acid modifications), a CDR2 having the amino acid sequence set forth in SEQ ID NO:33 (or a variant with one, two, or three amino acid modifications), and a CDR3 having the amino acid sequence set forth in SEQ ID NO:34 (or a variant with one, two, or three amino acid modifications), and the beta chain polypeptide can include a CDR1 having the amino acid sequence set forth in SEQ ID NO:23 (or a variant with one, two, or three amino acid modifications), a CDR2 having the amino acid sequence set forth in SEQ ID NO:24 (or a variant with one, two, or three amino acid modifications), and a CDR3 having the amino acid sequence set forth in SEQ ID NO:25 (or a variant with one, two, or three amino acid modifications).

Examples of amino acid modifications with respect to the amino acid sequence set forth in SEQ ID NOs:1, 2, 3, 10, 11, 12, 23, 24, 25, 32, 33, and 34 include, without limitation, amino acid substitutions, amino acid deletions, and amino acid additions. In some cases, a variant of SEQ ID NOs:3, 12, 25, or 34 can include no more than one amino acid modification. Amino acid modifications can be made, for example, to improve the binding and/or contact with the ATM or ARID1A peptide.

In some cases, an amino acid substitution that can be engineered into a TCR containing the sequence set forth in SEQ ID NO:1, 2, 3, 10, 11, 12, 23, 24, 25, 32, 33, or 34 can be a conservative amino acid substitution. For example, conservative amino acid substitutions can be made by substituting one amino acid residue for another amino acid residue having a similar side chain. Families of amino acid residues having similar side chains can include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine).

In some cases, an amino acid substitution that can be engineered into a TCR containing the sequence set forth in SEQ ID NO:1, 2, 3, 10, 11, 12, 23, 24, 25, 32, 33, or 34 can be a non-conservative amino acid substitution. Non-conservative amino acid substitutions can be made by substituting one amino acid residue for another amino acid residue having a dis-similar side chain. Examples of non-conservative substitutions that can be used as described herein include, without limitation, substituting (a) a hydrophilic residue (e.g., serine or threonine) for a hydrophobic residue (e.g., leucine, isoleucine, phenylalanine, valine, or alanine); (b) a cysteine or proline for any other residue; (c) a residue having a basic side chain (e.g., lysine, arginine, or histidine) for a residue having an acidic side chain (e.g., aspartic acid or glutamic acid); and (d) a residue having a bulky side chain (e.g., phenylalanine) for glycine or other residue having a small side chain.

Methods for generating amino acid sequence variants can include site-specific mutagenesis or random mutagenesis (e.g., by PCR) of the nucleic acid encoding the alpha and/or beta chain polypeptide. See, for example, Zoller, *Curr. Opin. Biotechnol.* 3: 348-354 (1992). Both naturally occurring and non-naturally occurring amino acids (e.g., artificially-derivatized amino acids) can be used to generate amino acid sequence variants of the alpha and/or beta chain polypeptides provided herein.

In some cases, the constant region of an alpha chain polypeptide of a TCR provided herein having affinity for an ATM peptide can have an amino acid sequence having at least 80% identity to the amino acid sequence set forth in SEQ ID NO:17 or SEQ ID NO:21. For example, the constant region of an alpha chain polypeptide of a TCR provided herein can have an amino acid sequence having at least 82%, 83%, 84%, 85%, 86%, 87%, 88%, 89%, 90%, 91%, 92%, 93%, 94%, 95%, 96%, 97%, 98%, 99%, or 100% identity to the amino acid sequence set forth in SEQ ID NO:17 or SEQ ID NO:21.

In some cases, the variable region of an alpha chain polypeptide of a TCR provided herein having affinity for an ATM peptide can have an amino acid sequence having at least 80% identity to the amino acid sequence set forth in SEQ ID NO:45 provided that the alpha chain includes the appropriate combination of CDRs (or variants of the CDRs) described herein. For example, the variable region of an alpha chain of a TCR provided herein can have an amino acid sequence having at least 80%, 82%, 83%, 84%, 85%, 86%, 87%, 88%, 89%, 90%, 91%, 92%, 93%, 94%, 95%, 96%, 97%, 98%, 99%, or 100% identity to the amino acid sequence set forth in SEQ ID NO:45, provided that it includes (a) SEQ ID NO:10 (or SEQ ID NO:10 with no more than three, two, or one amino acid modifications), (b) SEQ ID NO:11 (or SEQ ID NO:11 with no more than three, two, or one amino acid modifications), and (c) SEQ ID NO:12 (or SEQ ID NO:12 with no more than three, two, or one amino acid modifications).

In some cases, the variable region of an alpha chain polypeptide of a TCR provided herein can include the amino acid sequence set forth in SEQ ID NO:45 (or a variant of SEQ ID NO:45 with one, two, three, four, five, six, seven, eight, nine, or 10 amino acid modifications, provided that the alpha chain includes the appropriate combination of CDRs (or variants of the CDRs) described herein). Amino acid modifications can be amino acid substitutions, amino acid deletions, or amino acid additions. Amino acid substitutions for SEQ ID NO:45 can be conservative amino acid substitutions or non-conservative amino acid substitutions as discussed above for SEQ ID NOs:1, 2, 3, 10, 11, 12, 23, 24, 25, 32, 33, and 34. In some cases, a variant of SEQ ID NO:45 can include no more than one, two, three, four, or five amino acid modifications.

In some cases, an alpha chain polypeptide of a TCR provided herein having affinity for an ATM peptide can have an amino acid sequence having at least 80% identity to the amino acid sequence set forth in SEQ ID NO:18 or SEQ ID NO:22, provided that the alpha chain includes the appropriate combination of CDRs (or variants of the CDRs) described herein. For example, an alpha chain of a TCR provided herein can have an amino acid sequence having at least 80%, 82%, 83%, 84%, 85%, 86%, 87%, 88%, 89%, 90%, 91%, 92%, 93%, 94%, 95%, 96%, 97%, 98%, 99%, or 100% identity to the amino acid sequence set forth in SEQ ID NO:18, provided that it includes (a) SEQ ID NO:10 (or SEQ ID NO:10 with no more than three, two, or one amino acid modifications), (b) SEQ ID NO:11 (or SEQ ID NO:11 with no more than three, two, or one amino acid modifications), and (c) SEQ ID NO:12 (or SEQ ID NO:12 with no more than three, two, or one amino acid modifications). In another example, an alpha chain of a TCR provided herein can have an amino acid sequence having at least 80%, 82%, 83%, 84%, 85%, 86%, 87%, 88%, 89%, 90%, 91%, 92%, 93%, 94%, 95%, 96%, 97%, 98%, 99%, or 100% identity to the amino acid sequence set forth in SEQ ID NO:22, provided that it includes (a) SEQ ID NO:10 (or SEQ ID NO:10 with no more than three, two, or one amino acid modifications), (b) SEQ ID NO:11 (or SEQ ID NO:11 with no more than three, two, or one amino acid modifications), and (c) SEQ ID NO:12 (or SEQ ID NO:12 with no more than three, two, or one amino acid modifications).

In some cases, an alpha chain polypeptide of a TCR provided herein can include the amino acid sequence set forth in SEQ ID NO:18 (or a variant of SEQ ID NO:18 with one, two, three, four, five, six, seven, eight, nine, or 10 amino acid modifications, provided that the alpha chain includes the appropriate combination of CDRs (or variants of the CDRs) described herein) or SEQ ID NO:22 (or a variant of SEQ ID NO:22 with one, two, three, four, five, six, seven, eight, nine, or 10 amino acid modifications, provided that the alpha chain includes the appropriate combination of CDRs (or variants of the CDRs) described herein). Amino acid modifications can be amino acid substitutions, amino acid deletions, or amino acid additions. Amino acid substitutions for SEQ ID NO:18 or SEQ ID NO:22 can be conservative amino acid substitutions or non-conservative amino acid substitutions as discussed above for SEQ ID NOs:1, 2, 3, 10, 11, 12, 23, 24, 25, 32, 33, and 34. In some cases, a variant of SEQ ID NO:18 or SEQ ID NO:22 can include no more than one, two, three, four, or five amino acid modifications.

In some cases, the constant region of a beta chain polypeptide of a TCR provided herein having affinity for an ATM peptide can have an amino acid sequence having at least 80% identity to the amino acid sequence set forth in SEQ ID NO:8 or SEQ ID NO:19. For example, the constant region of a beta chain polypeptide of a TCR provided herein can have an amino acid sequence having at least 82%, 83%, 84%, 85%, 86%, 87%, 88%, 89%, 90%, 91%, 92%, 93%, 94%, 95%, 96%, 97%, 98%, 99%, or 100% identity to the amino acid sequence set forth in SEQ ID NO:8 or SEQ ID NO:19.

In some cases, the variable region of a beta chain polypeptide of a TCR provided herein having affinity for an ATM peptide can have an amino acid sequence having at least 80% identity to the amino acid sequence set forth in SEQ ID NO:47, provided that the beta chain includes the appropriate combination of CDRs (or variants of the CDRs) described herein. For example, the variable region of a beta chain of a TCR provided herein can have an amino acid sequence having at least 80%, 82%, 83%, 84%, 85%, 86%, 87%, 88%, 89%, 90%, 91%, 92%, 93%, 94%, 95%, 96%, 97%, 98%, 99%, or 100% identity to the amino acid sequence set forth in SEQ ID NO:47, provided that it includes (a) SEQ ID NO:1 (or SEQ ID NO:1 with no more than three, two, or one amino acid modifications), (b) SEQ ID NO:2 (or SEQ ID NO:2 with no more than three, two, or one amino acid modifications), and (c) SEQ ID NO:3 (or SEQ ID NO:3 with no more than three, two, or one amino acid modifications).

In some cases, the variable region of a beta chain polypeptide of a TCR provided herein can include the amino acid sequence set forth in SEQ ID NO:47 (or a variant of SEQ ID NO:47 with one, two, three, four, five, six, seven, eight, nine, or 10 amino acid modifications, provided that the beta chain includes the appropriate combination of CDRs (or variants of the CDRs) described herein). Amino acid modifications can be amino acid substitutions, amino acid deletions, or amino acid additions. Amino acid substitutions for SEQ ID NO:47 can be conservative amino acid substitutions or non-conservative amino acid substitutions as discussed above for SEQ ID NOs:1, 2, 3, 10, 11, 12, 23, 24, 25, 32, 33, and 34. In some cases, a variant of SEQ ID NO:47 can include no more than one, two, three, four, or five amino acid modifications.

In some cases, a beta chain polypeptide of a TCR provided herein having affinity for an ATM peptide can have an amino acid sequence having at least 80% identity to the amino acid sequence set forth in SEQ ID NO:9 or SEQ ID NO:20, provided that the beta chain includes the appropriate combination of CDRs (or variants of the CDRs) described herein. For example, a beta chain of a TCR provided herein can have an amino acid sequence having at least 80%, 82%, 83%, 84%, 85%, 86%, 87%, 88%, 89%, 90%, 91%, 92%, 93%, 94%, 95%, 96%, 97%, 98%, 99%, or 100% identity to the amino acid sequence set forth in SEQ ID NO:9, provided that it includes (a) SEQ ID NO:1 (or SEQ ID NO:1 with no more than three, two, or one amino acid modifications), (b) SEQ ID NO:2 (or SEQ ID NO:2 with no more than three, two, or one amino acid modifications), and (c) SEQ ID NO:3 (or SEQ ID NO:3 with no more than three, two, or one amino acid modifications). In another example, a beta chain of a TCR provided herein can have an amino acid sequence having at least 80%, 82%, 83%, 84%, 85%, 86%, 87%, 88%, 89%, 90%, 91%, 92%, 93%, 94%, 95%, 96%, 97%, 98%, 99%, or 100% identity to the amino acid sequence set forth in SEQ ID NO:20, provided that it includes (a) SEQ ID NO:1 (or SEQ ID NO:1 with no more than three, two, or one amino acid modifications), (b) SEQ ID NO:2 (or SEQ ID NO:2 with no more than three, two, or one amino acid modifications), and (c) SEQ ID NO:3 (or SEQ ID NO:3 with no more than three, two, or one amino acid modifications).

In some cases, a beta chain polypeptide of a TCR provided herein can have an amino acid sequence having at least 80% identity to the amino acid sequence set forth the amino acid sequence set forth in SEQ ID NO:9 (or a variant of SEQ ID NO:9 with one, two, three, four, five, six, seven, eight, nine, or 10 amino acid modifications, provided that the beta chain includes the appropriate combination of CDRs (or variants of the CDRs) described herein) or SEQ ID NO:20 (or a variant of SEQ ID NO:20 with one, two, three, four, five, six, seven, eight, nine, or 10 amino acid modifications, provided that the beta chain includes the appropriate combination of CDRs (or variants of the CDRs) described herein). Amino acid modifications can be amino acid substitutions, amino acid deletions, or amino acid additions. Amino acid substitutions for SEQ ID NO:9 or SEQ ID NO:20 can be conservative amino acid substitutions or non-conservative amino acid substitutions as discussed above for SEQ ID NOs:1, 2, 3, 10, 11, 12, 23, 24, 25, 32, 33, and 34. In some cases, a variant of SEQ ID NO:9 or SEQ ID NO:20 can include no more than one, two, three, four, or five amino acid modifications.

In some cases, the constant region of an alpha chain polypeptide of a TCR provided herein having affinity for an ARID1A peptide can have an amino acid sequence having at least 80% identity to the amino acid sequence set forth in SEQ ID NO:39 or SEQ ID NO:43. For example, the constant region of an alpha chain polypeptide of a TCR provided herein can have an amino acid sequence having at least 80%, 82%, 83%, 84%, 85%, 86%, 87%, 88%, 89%, 90%, 91%, 92%, 93%, 94%, 95%, 96%, 97%, 98%, 99%, or 100% identity to the amino acid sequence set forth in SEQ ID NO:39 or SEQ ID NO:43.

In some cases, the variable region of an alpha chain polypeptide of a TCR provided herein having affinity for an ARID1A peptide can have an amino acid sequence having at least 80% identity to the amino acid sequence set forth in SEQ ID NO:46, provided that the alpha chain includes the appropriate combination of CDRs (or variants of the CDRs) described herein. For example, the variable region of an alpha chain of a TCR provided herein can have an amino acid sequence having at least 80%, 82%, 83%, 84%, 85%, 86%, 87%, 88%, 89%, 90%, 91%, 92%, 93%, 94%, 95%, 96%, 97%, 98%, 99%, or 100% identity to the amino acid sequence set forth in SEQ ID NO:46, provided that it includes (a) SEQ ID NO:32 (or SEQ ID NO:32 with no more than three, two, or one amino acid modifications), (b) SEQ ID NO:33 (or SEQ ID NO:33 with no more than three, two, or one amino acid modifications), and (c) SEQ ID NO:34 (or SEQ ID NO:34 with no more than three, two, or one amino acid modifications).

In some cases, the variable region of an alpha chain polypeptide of a TCR provided herein can include the amino acid sequence set forth in SEQ ID NO:46 (or a variant of SEQ ID NO:46 with one, two, three, four, five, six, seven, eight, nine, or 10 amino acid modifications, provided that the alpha chain includes the appropriate combination of CDRs (or variants of the CDRs) described herein). Amino acid modifications can be amino acid substitutions, amino acid deletions, or amino acid additions. Amino acid substitutions for SEQ ID NO:46 can be conservative amino acid substitutions or non-conservative amino acid substitutions as discussed above for SEQ ID NOs:1, 2, 3, 10, 11, 12, 23, 24, 25, 32, 33, and 34. In some cases, a variant of SEQ ID NO:46 can include no more than one, two, three, four, or five amino acid modifications.

In some cases, an alpha chain polypeptide of a TCR provided herein having affinity for an ARID1A peptide can have an amino acid sequence having at least 80% identity to the amino acid sequence set forth in SEQ ID NO:40 or SEQ ID NO:44, provided that the alpha chain includes the appropriate combination of CDRs (or variants of the CDRs) described herein. For example, an alpha chain of a TCR provided herein can have an amino acid sequence having at least 80%, 82%, 83%, 84%, 85%, 86%, 87%, 88%, 89%, 90%, 91%, 92%, 93%, 94%, 95%, 96%, 97%, 98%, 99%, or 100% identity to the amino acid sequence set forth in SEQ ID NO:40, provided that it includes (a) SEQ ID NO:32 (or SEQ ID NO:32 with no more than three, two, or one amino acid modifications), (b) SEQ ID NO:33 (or SEQ ID NO:33 with no more than three, two, or one amino acid modifications), and (c) SEQ ID NO:34 (or SEQ ID NO:34 with no more than three, two, or one amino acid modifications). In another example, an alpha chain of a TCR provided herein can have an amino acid sequence having at least 80%, 82%, 83%, 84%, 85%, 86%, 87%, 88%, 89%, 90%, 91%, 92%, 93%, 94%, 95%, 96%, 97%, 98%, 99%, or 100% identity to the amino acid sequence set forth in SEQ ID NO:44, provided that it includes (a) SEQ ID NO:32 (or SEQ ID NO:32 with no more than three, two, or one amino acid modifications), (b) SEQ ID NO:33 (or SEQ ID NO:33 with no more than three, two, or one amino acid modifications), and (c) SEQ ID NO:34 (or SEQ ID NO:34 with no more than three, two, or one amino acid modifications).

In some cases, an alpha chain polypeptide of a TCR provided herein having affinity for an ARID1A peptide can include the amino acid sequence set forth in SEQ ID NO:40 (or a variant of SEQ ID NO:40 with one, two, three, four, five, six, seven, eight, nine, or 10 amino acid modifications, provided that the alpha chain includes the appropriate combination of CDRs (or variants of the CDRs) described herein) or SEQ ID NO:44 (or a variant of SEQ ID NO:44 with one, two, three, four, five, six, seven, eight, nine, or 10 amino acid modifications, provided that the alpha chain includes the appropriate combination of CDRs (or variants of the CDRs) described herein). Amino acid modifications can be amino acid substitutions, amino acid deletions, or amino acid additions. Amino acid substitutions for SEQ ID NO:40 or SEQ ID NO:44 can be conservative amino acid substitutions or non-conservative amino acid substitutions as discussed above for SEQ ID NOs:1, 2, 3, 10, 11, 12, 23, 24, 25, 32, 33, and 34. In some cases, a variant of SEQ ID NO:40 or SEQ ID NO:44 can include no more than one, two, three, four, or five amino acid modifications.

In some cases, the constant region of a beta chain polypeptide of a TCR provided herein having affinity for an ARID1A peptide can have an amino acid sequence having at least 80% identity to the amino acid sequence set forth in SEQ ID NO:30 or SEQ ID NO:41. For example, the constant region of a beta chain polypeptide of a TCR provided herein can have an amino acid sequence having at least 80%, 82%, 83%, 84%, 85%, 86%, 87%, 88%, 89%, 90%, 91%, 92%, 93%, 94%, 95%, 96%, 97%, 98%, 99%, or 100% identity to the amino acid sequence set forth in SEQ ID NO:30 or SEQ ID NO:41.

In some cases, the variable region of a beta chain polypeptide of a TCR provided herein having affinity for an ARID1A peptide can have an amino acid sequence having at least 80% identity to the amino acid sequence set forth in SEQ ID NO:48, provided that the beta chain includes the appropriate combination of CDRs (or variants of the CDRs) described herein. For example, the variable region of a beta chain of a TCR provided herein can have an amino acid sequence having at least 80%, 82%, 83%, 84%, 85%, 86%, 87%, 88%, 89%, 90%, 91%, 92%, 93%, 94%, 95%, 96%, 97%, 98%, 99%, or 100% identity to the amino acid sequence set forth in SEQ ID NO:48, provided that it includes (a) SEQ ID NO:23 (or SEQ ID NO:23 with no more than three, two, or one amino acid modifications), (b) SEQ ID NO:24 (or SEQ ID NO:24 with no more than three, two, or one amino acid modifications), and (c) SEQ ID NO:25 (or SEQ ID NO:25 with no more than three, two, or one amino acid modifications).

In some cases, the variable region of a beta chain polypeptide of a TCR provided herein can include the amino acid sequence set forth in SEQ ID NO:48 (or a variant of SEQ ID NO:48 with one, two, three, four, five, six, seven, eight, nine, or 10 amino acid modifications, provided that the beta chain includes the appropriate combination of CDRs (or variants of the CDRs) described herein). Amino acid modifications can be amino acid substitutions, amino acid deletions, or amino acid additions. Amino acid substitutions for SEQ ID NO:48 can be conservative amino acid substitutions or non-conservative amino acid substitutions as discussed above for SEQ ID NOs:1, 2, 3, 10, 11, 12, 23, 24, 25, 32, 33, and 34. In some cases, a variant of SEQ ID NO:48 can include no more than one, two, three, four, or five amino acid modifications.

In some cases, a beta chain polypeptide of a TCR provided herein having affinity for an ARID1A peptide can have an amino acid sequence having at least 80% identity to the amino acid sequence set forth in SEQ ID NO:31 or SEQ ID NO:42, provided that the beta chain includes the appropriate combination of CDRs (or variants of the CDRs) described herein. For example, a beta chain of a TCR provided herein can have an amino acid sequence having at least 80%, 82%, 83%, 84%, 85%, 86%, 87%, 88%, 89%, 90%, 91%, 92%, 93%, 94%, 95%, 96%, 97%, 98%, 99%, or 100% identity to the amino acid sequence set forth in SEQ ID NO:31, provided that it includes (a) SEQ ID NO:23 (or SEQ ID NO:23 with no more than three, two, or one amino acid modifications), (b) SEQ ID NO:24 (or SEQ ID NO:24 with no more than three, two, or one amino acid modifications), and (c) SEQ ID NO:25 (or SEQ ID NO:25 with no more than three, two, or one amino acid modifications). In another example, a beta chain of a TCR provided herein can have an amino acid sequence having at least 80%, 82%, 83%, 84%, 85%, 86%, 87%, 88%, 89%, 90%, 91%, 92%, 93%, 94%, 95%, 96%, 97%, 98%, 99%, or 100% identity to the amino acid sequence set forth in SEQ ID NO:42, provided that it includes (a) SEQ ID NO:23 (or SEQ ID NO:23 with no more than three, two, or one amino acid modifications), (b) SEQ ID NO:24 (or SEQ ID NO:24 with no more than three, two, or one amino acid modifications), and (c) SEQ ID NO:25 (or SEQ ID NO:25 with no more than three, two, or one amino acid modifications).

In some cases, a beta chain polypeptide of a TCR provided herein having affinity for an ARID1A peptide can have an amino acid sequence having at least 80% identity to the amino acid sequence set forth the amino acid sequence set forth in SEQ ID NO:31 (or a variant of SEQ ID NO:31 with one, two, three, four, five, six, seven, eight, nine, or 10 amino acid modifications, provided that the beta chain includes the appropriate combination of CDRs (or variants of the CDRs) described herein) or SEQ ID NO:42 (or a variant of SEQ ID NO:42 with one, two, three, four, five, six, seven, eight, nine, or 10 amino acid modifications, provided that the beta chain includes the appropriate combination of CDRs (or variants of the CDRs) described herein). Amino acid modifications can be amino acid substitutions, amino acid deletions, or amino acid additions. Amino acid substitutions for SEQ ID NO:31 or SEQ ID NO:42 can be conservative amino acid substitutions or non-conservative amino acid substitutions as discussed above for SEQ ID NOs:1, 2, 3, 10, 11, 12, 23, 24, 25, 32, 33, and 34. In some cases, a variant of SEQ ID NO:31 or SEQ ID NO:42 can include no more than one, two, three, four, or five amino acid modifications.

In some cases, a TCR provided herein can include no more than four (e.g., four, three, two, or one) amino acid modifications (e.g., amino acid substitutions, amino acid deletions, or amino acid additions) in one, two, three, or all four of the framework regions (the regions between the CDRs). For example, a TCR provided herein that has affinity for a ATM peptide can include no more than four (e.g., four, three, two, or one) amino acid modifications in one, two, three, or all four of the alpha chain framework regions set forth in SEQ ID NOs:13, 14, 15, and 16 and/or the beta chain framework regions set forth in SEQ ID NOs:4, 5, 6, and 7. For example, a TCR provided herein that has affinity for a ARID1A peptide can include no more than four (e.g., four, three, two, or one) amino acid modifications in one, two, three, or all four of the alpha chain framework regions set forth in SEQ ID NOs:35, 36, 37, and 38 and/or the beta chain framework regions set forth in SEQ ID NOs:26, 27, 28, and 29. In some cases, a TCR provided herein can include no more than four (e.g., four, three, two, or one) amino acid modifications (e.g., amino acid substitutions, amino acid deletions, or amino acid additions) in one, two, three, or all four of the framework regions set forth in SEQ ID NOs:4, 5, 6, 7, 13, 14, 15, and 16 and (i) one, two, or three amino acid modifications in one, two, or all three CDRs of the alpha chain variable region having the amino acid sequences set forth in SEQ ID NOs:10, 11, and 12 and/or (ii) one, two, or three amino acid modifications in one, two, or all three CDRs of the beta chain variable region having the amino acid sequences set forth in SEQ ID NOs:1, 2, and 3. In some cases, a TCR provided herein can include no more than four (e.g., four, three, two, or one) amino acid modifications (e.g., amino acid substitutions, amino acid deletions, or amino acid additions) in one, two, three, or all four of the framework regions set forth in SEQ ID NOs:26, 27, 28, 29, 35, 36, 37, and 38 and (i) one, two, or three amino acid modifications in one, two, or all three CDRs of the alpha chain variable region having the amino acid sequences set forth in SEQ ID NOs:32, 33, and 34 and/or (ii) one, two, or three amino acid modifications in one, two, or all three CDRs of the beta chain variable region having the amino acid sequences set forth in SEQ ID NOs:23, 24, and 25.

In some cases, a TCR provided herein can have the sequences as set forth in Table 3 (see FIG. 10 for the sequences).

TABLE 3

Exemplary TCRs.

| TCR | SEQ ID NO of beta chain CDRs | SEQ ID NO of beta chain Framework regions | SEQ ID of constant region in beta chain | SEQ ID NO of variable region | SEQ ID NO of beta chain | SEQ ID NOs of alpha chain CDRs | SEQ ID NO of alpha chain Framework regions | SEQ ID of Constant region in alpha chain | SEQ ID NO of variable region | SEQ ID NO of alpha chain |
|---|---|---|---|---|---|---|---|---|---|---|
| TRBV9*01 + TRAV14/DV4 chimeric TCR | 1, 2, 3 | 4, 5, 6, 7 | 8 | 47 | 9 | 10, 11, 12 | 13, 14, 15, 16 | 17 | 45 | 18 |

TABLE 3-continued

Exemplary TCRs.

| TCR | SEQ ID NO of beta chain CDRs | SEQ ID NO of beta chain Framework regions | SEQ ID of constant region in beta chain | SEQ ID NO of variable region | SEQ ID NO of beta chain | SEQ ID NOs of alpha chain CDRs | SEQ ID NO of alpha chain Framework regions | SEQ ID of Constant region in alpha chain | SEQ ID NO of variable region | SEQ ID NO of alpha chain |
|---|---|---|---|---|---|---|---|---|---|---|
| TRBV9*01 + TRAV14/DV4 Human TCR | 1, 2, 3 | 4, 5, 6, 7 | 19 | 47 | 20 | 10, 11, 12 | 13, 14, 15, 16 | 21 | 45 | 22 |
| TRBV25-1 + TRAV20 Chimeric TCR | 23, 24, 25 | 26, 27, 28, 29 | 30 | 48 | 31 | 32, 33, 34 | 35, 36, 37, 38 | 39 | 46 | 40 |
| TRBV25-1 + TRAV20 Human TCR | 23, 24, 25 | 26, 27, 28, 29 | 41 | 48 | 42 | 32, 33, 34 | 35, 36, 37, 38 | 43 | 46 | 44 |

Figure 9B:
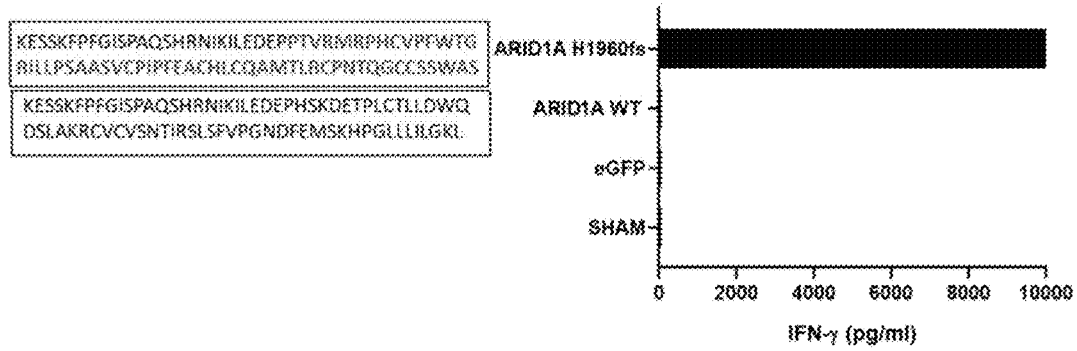
FIG. 9B contains a graph of interferon gamma (IFNγ) (pg/mL) in the supernatant after TCR-transduced T cells were co-cultured overnight with dendritic cells expressing wildtype (wt) ARID1A or mutated forms of ARID1A (1960fs).

This document also provides isolated nucleic acids that encode an alpha chain polypeptide of a TCR provided herein, a beta chain polypeptide of a TCR provided herein, or both an alpha chain polypeptide of a TCR provided herein and a beta chain polypeptide of a TCR provided herein. See, for example, FIG. 1C, FIG. 3, FIG. 5, FIG. 9, FIG. 11A, FIG. 11B, FIG. 13A, FIG. 13B, FIG. 15A, FIG. 15B, FIG. 17A, or FIG. 17B. In some cases, the nucleic acid sequence can be codon optimized for expression in a host cell (e.g., a human host cell). See, for example, FIG. 2, FIG. 4, FIG. 6, FIG. 8, FIG. 12A, FIG. 12B, FIG. 14A, FIG. 14B, FIG. 16A, FIG. 16B, FIG. 18A, or FIG. 18B. In addition, this document provides vectors containing one or more of such nucleic acids. The nucleic acids provided herein can be single stranded and double stranded nucleic acids of any appropriate type (e.g., DNA, RNA, or DNA/RNA hybrids). The nucleic acids provided herein can be used therapeutically or can be used in methods for producing a TCR.

In some cases, a nucleic acid provided herein includes a nucleic acid sequence that encodes an alpha chain of a TCR and a nucleic acid sequence that encodes a beta chain of a TCR. The nucleic acid also can include a nucleic acid sequence encoding a linker. The nucleic acid sequence encoding the linker can be between the nucleic acid encoding an alpha chain and the nucleic acid encoding the beta chain to allow the alpha and beta chains to be encoded by the same contiguous nucleic acid sequence. For example, the nucleic acid sequence encoding the linker can be 3' of the nucleic acid sequence encoding the alpha chain and 5' of the nucleic acid sequence encoding the beta chain or it can be 3' of the nucleic acid sequence encoding the beta chain and 5' of the nucleic acid sequence encoding the alpha chain.

In some cases, the linker can be a self-cleaving peptide (e.g., a 2A peptide) such that during translation of the transcripts, the growing polypeptide can be cleaved at the 2A peptide with translation continuing through to the next chain. When designing a vector to express the alpha and beta chains as a multicistronic unit, the nucleic acid encoding the alpha and beta chains and the self-cleaving peptide (e.g., a 2A peptide) can be designed such that they are in translational frame with each other. Examples of 2A peptides that can be used as described herein include, without limitation, a 2A peptide of foot-and-mouth disease virus (FMDV), a 2A peptide of equine rhinitis A virus (ERAVO), a 2A peptide of *Thosea asigna* virus (TaV), or a 2A peptide of porcine teschovirus-1 (PTV-1). 2A peptides derived from FMDV, ERAV, PTV-1, and TaV are referred to herein as "F2A," "E2A," "P2A," and "T2A," respectively. Table 4 provides exemplary amino acid sequences of 2A peptides.

TABLE 4

Exemplary 2A peptides that can be used as described herein.

| Type | Peptide Sequence | SEQ ID NO: |
|---|---|---|
| P2A | GSGATNFSLLKQAGDVEENPGP | 69 |
| | or | |
| | RAKRSGSGATNFSLLKQAGDVE ENPGP | 95 |
| T2A | GSGEGRGSLLTCGDVEENPGP | 70 |
| E2A | GSGQCTNYALLKLAGDVESNP GP | 71 |
| F2A | GSGVKQTLNFDLLKLAGDV ESNPGP | 72 |

In some cases, an Internal Ribosome Entry Site (IRES) can be used in place of (or in addition to) a self-cleaving peptide. Examples of IRES sequences that can be used as described herein include, without limitation, an Encephalomyocrditis virus (EMCV) IRES (e.g., IRES2), a Hepatitis C virus (HCV) IRES, a Picoma virus IRES, and a Pestivirus IRES.

In some cases, a linker can include a furin cleavage site. Furin is a ubiquitously expressed protease that resides in the trans-golgi and processes protein precursors before their secretion. Furin cleaves at the COOH terminus of its consensus recognition sequence. Examples of furin consensus recognition sequences (or "furin cleavage sites") that can be used as described herein include, without limitation, Arg-X-Lys-Arg (SEQ ID NO:73) or Arg-X-Arg-Arg (SEQ ID NO:74), (Lys/Arg)-Arg-X-(Lys/Arg)-Arg (SEQ ID NO:75) and Arg-X-X-Arg (SEQ ID NO:76), such as an Arg-Gln-Lys-Arg (SEQ ID NO:77), where X is any naturally occurring amino acid.

A vector that includes one or more nucleic acids that encode an alpha chain and/or beta chain of a TCR provided herein can be a nucleic acid vector (e.g., naked DNA or plasmid vector) or a viral vector. Examples of viral vectors that can be designed to include one or more nucleic acids encoding an alpha chain and/or beta chain of a TCR provided herein include, without limitation, retroviral vectors, parvovirus-based vectors (e.g., adenoviral-based vectors and adeno-associated virus (AAV)-based vectors), lentiviral vectors (e.g., herpes simplex (HSV)-based vectors), or poxviral vectors (e.g., vaccinia virus-based vectors and fowlpox virus-based vectors), and hybrid or chimeric viral vectors. For example, a viral vector having an adenoviral backbone with lentiviral components such as those described elsewhere (Zheng et al., *Nat. Biotech.,* 18(2):176-80 (2000); WO 98/22143; WO 98/46778; and WO 00/17376) or viral vectors having an adenoviral backbone with AAV components such as those described elsewhere (Fisher et al., *Hum. Gene Ther.,* 7:2079-2087 (1996)) can be designed to include one or more nucleic acids encoding an alpha chain and/or beta chain of a TCR provided herein. Any appropriate nucleic acid or viral vector construction methods can be used to make a nucleic acid vector that includes one or more nucleic acids encoding an alpha chain and/or beta chain of a TCR provided herein (see, e.g., Green and Sambrook, Molecular Cloning: A Laboratory Manual, 4th edition, Cold Spring Harbor Laboratory, N Y (2012); and Ausubel et al., Current Protocols in Molecular Biology, Green Publishing Associates and John Wiley & Sons, New York, New York (1987-2008)).

A vector provided herein (e.g., a nucleic acid or viral vector provided herein) can include any appropriate promoter and/or other regulatory sequences (e.g., transcription and translation initiation and termination codons) operably linked the nucleic acid encoding a polypeptide (e.g., an alpha chain and/or beta chain of a TCR provided herein). In some cases, a promoter used to drive expression of an alpha chain and/or beta chain of a TCR provided herein can be a constitutive or regulatable promotor. Examples of regulatable promoters that can be used as described herein include, without limitation, inducible promotors, repressible promotors, and tissue-specific promoters. Examples of viral promotors that can be used as described herein include, without limitation, adenoviral promotors, vaccinia virus promotors, and AAV promoters. In some embodiments, the promoter can be a viral 5' long terminal repeat (LTR) or 3' LTR.

In some cases, a vector includes a separate promoter to drive expression of each chain instead of using a linker between the chains. In these cases, one promoter sequence can drive expression of an alpha chain, and a separate promoter sequence can drive expression of a beta chain. These two promoter sequences can be the same or different.

This document also provides cells (e.g., host cells or isolated cells) that include at least one nucleic acid provided herein (e.g., a nucleic acid encoding an alpha chain and/or beta chain of a TCR having affinity for an ATM peptide and/or a nucleic acid encoding an alpha chain and/or beta chain of a TCR having affinity for an ARID1A peptide, or a nucleic acid vector or viral vector provided herein). Such cells (e.g., host cells or isolated cells) that can be designed to include one or more nucleic acids provided herein can be prokaryotic cells or eukaryotic cells. Examples of prokaryotic cells that can include one or more nucleic acids provided herein (e.g., a nucleic acid encoding an alpha chain and/or beta chain of a TCR provided herein, or a nucleic acid vector or viral vector provided herein) include, without limitation, *E. coli* (e.g., Tb-1, TG-1, DH5α, XL-Blue MRF (Stratagene), SA2821, or Y1090 cells), *Bacillus subtilis, Salmonella typhimurium, Serratia marcescens*, or *Pseudomonas* (e.g., *P. aerugenosa*) cells.

Examples of eukaryotic cells that can include one or more nucleic acids provided herein (e.g., a nucleic acid encoding an alpha chain and/or beta chain of a TCR having affinity for an ATM peptide and/or a nucleic acid encoding an alpha chain and/or beta chain of a TCR having affinity for an ARID1A peptide, or a nucleic acid vector or viral vector provided herein) include, without limitation, insect cells (e.g., Sf9 or Ea4 cells), yeast cells (e.g., *S. cerevisiae* cells), and mammalian cells (e.g., mouse, rat, hamster, monkey, or human cells). For example, VERO cells, HeLa cells, 3T3 cells, Chinese hamster ovary (CHO) cells, W138 BHK cells, COS-7 cells, and MDCK cells can be designed to include a nucleic acid provided herein (e.g., a nucleic acid encoding an alpha chain and/or beta chain of a TCR having affinity for an ATM peptide and/or a nucleic acid encoding an alpha chain and/or beta chain of a TCR having affinity for an ARID1A peptide, or a nucleic acid vector or viral vector provided herein).

In some cases, a eukaryotic cell that includes a nucleic acid provided herein (e.g., a nucleic acid encoding an alpha chain and/or beta chain of a TCR having affinity for an ATM peptide and/or a nucleic acid encoding an alpha chain and/or beta chain of a TCR having affinity for an ARID1A peptide, or a nucleic acid vector or viral vector provided herein) is an immune cell such as a T cell. Such cells can include an exogenous TCR, expressed from a nucleic acid provided herein, on their surface that has reactivity against the mutated form of ATM without having reactivity to the non-mutated form of ATM and/or an exogenous TCR, expressed from a nucleic acid provided herein, on their surface that has reactivity against the mutated form of ARID1A without having reactivity to the non-mutated form of ARID1A. A T cell can be any type of T cell and can be of any developmental stage, including $CD4^+$ and/or $CD8^+$ T cells. For example, the T cells can be helper T cells, e.g., Th1 and Th2 cells, $CD8^+$ T cells (e.g., cytotoxic T cells), tumor infiltrating cells (TILs), memory T cells, naive T cells, cytotoxic T lymphocytes (CTLs), regulatory T cells, activated T cells, memory T cells, or natural killer cells. The T cell can be a cultured T cell, e.g., a primary T cell or a T cell from a cultured T cell line, e.g., Jurkat or Sup-T1. In some cases, the T cell can be isolated from a mammal such as a human. Mammalian T cells can be obtained, for example, from blood, bone marrow, lymph node, the thymus, or other tissues or fluids. T cells also can be enriched or purified.

In some cases, the T cell can be isolated from the mammal to be treated, i.e., the cells are autologous to the mammal (e.g., human), and modified to include a nucleic acid provided herein (e.g., a nucleic acid encoding an alpha chain and/or beta chain of a TCR provided herein, or a nucleic acid vector or viral vector provided herein) and comprise an exogenous TCR on the surface of the cell that is expressed from the nucleic acid. For example, for autologous cells, the immune cells can be obtained from the mammal's blood, cord blood, or bone marrow. In some cases, the T cells are heterologous to the mammal, i.e., the cells are not from the mammal to be treated.

In some cases, an immune cell such as a T cell (e.g., a human T cell) that includes a nucleic acid provided herein (e.g., a nucleic acid encoding an alpha chain and/or beta chain of a TCR having affinity for an ATM peptide and/or a nucleic acid encoding an alpha chain and/or beta chain of a TCR having affinity for an ARID1A peptide, or a nucleic acid vector or viral vector provided herein) and comprises an exogenous TCR expressed from the nucleic acid, can lack expression of an endogenous alpha chain of a TCR and/or lack expression of an endogenous beta chain of a TCR. Any appropriate method can be used to generate T cells that lack expression of one or both chains of an endogenous TCR. For example, gene editing techniques such as those that involve using Clustered Regularly Interspaced Short Palindromic Repeats (CRISPR) technology or Transcription Activator-Like Effector Nuclease (TALEN) technology can be used to interfere with the expression of one or both chains of an endogenous TCR.

In some cases, an immune cell such as a natural killer (NK) cell that includes a nucleic acid provided herein (e.g., a nucleic acid encoding an alpha chain and/or beta chain of a TCR having affinity for an ATM peptide and/or a nucleic acid encoding an alpha chain and/or beta chain of a TCR having affinity for an ARID1A peptide, or a nucleic acid vector or viral vector provided herein) and comprises an exogenous TCR expressed from the nucleic acid, can be engineered to express one or more of the CD3 chains of the TCR complex (e.g., the CD3ε, CD3γ, CD3 ζ, and optionally CD3δ). In such cases, an exogenous TCR can be expressed on the surface of the immune cell (e.g., a NK cell) in combination with the exogenously provided one or more CD3 chains of a CD3 complex.

In some cases, an immune cell such as a T cell (e.g., a human T cell) that includes a nucleic acid provided herein (e.g., a nucleic acid encoding an alpha chain and/or beta chain of a TCR having affinity for an ATM peptide and/or a nucleic acid encoding an alpha chain and/or beta chain of a TCR having affinity for an ARID1A peptide, or a nucleic acid vector or viral vector provided herein) and comprises an exogenous TCR expressed from the nucleic acid, expresses an endogenous TCR. In such cases, a portion of the TCRs present on the surface of such T cells can be endogenous TCRs, a portion of the TCRs present on the surface of such T cells can be exogenously provided TCRs (e.g., TCRs containing a combination of alpha and beta chain polypeptides described herein), and a portion of the TCRs present on the surface of such T cells can have one endogenous provided TCR chain and one exogenously provided TCR chain.

In some cases, the constant regions of the alpha and beta chains encoded by a nucleic acid provided herein can be engineered to include sequences that encode one or more cysteine residues to increase the pairing of the alpha and beta chains with each other when expressed within a cell. Examples of such cysteine residues include, without limitation, those described elsewhere (see, e.g., Kuball et al., *Blood,* 109:2331-2338 (2007)).

Any appropriate method can be used to introduce one or more nucleic acids provided herein (e.g., a vector containing a nucleic acid encoding the alpha chain and/or beta chain polypeptides of a TCR provided herein) into a cell (e.g., a host cell or an isolated cell). For example, calcium chloride-mediated transformation, transduction, conjugation, triparental mating, DEAE, dextran-mediated transfection, infection, membrane fusion with liposomes, high velocity bombardment with DNA-coated microprojectiles, direct microinjection into single cells, electroporation, or combinations thereof can be used to introduce a nucleic acid provided herein into a cell (e.g., a host cell or an isolated cell) (see, e.g., Green and Sambrook, Molecular Cloning: A Laboratory Manual, 4th edition, Cold Spring Harbor Laboratory, NY (2012); Davis et al., Basic Methods in Molecular Biology (1986); and Neumann et al., *EMBO J.,* 1:841 (1982)).

The immune cells (e.g., T cells) can be activated and expanded, before or after introduction of the nucleic acid. T-cell activation reagents are commercially available, including CTS™ Dynabeads™ CD3/28, MACS GMP ExpAct Treg beads (Miltenyi Biotec), MACS GMP TransAct CD3/28 beads (Miltenyi Biotec), and Expamer technology (Juno Therapeutics). See, for example, Wang and Riviere, *Molecular Therapy Oncolytics,* 3:16015 (2016). T cells can be expanded, for example, using a GE WAVE bioreactor system that includes a Cellbag Bioreactor and a rocking base, and which allows the cells to expand to more than $10^7$ cells/mL. In some cases, T cells can be expanded using Gas Permeable Rapid Expansion (G-Rex®) (Wilson Wolf Manufacturing), which includes a cell culture flask with a gas-permeable membrane at the base that allows cells to grow to a high density. T cells also can be expanded using a CliniMACS Prodigy system (Miltenyi Biotec), which uses a magnetic cell separation system, and a cell cultivation device. See, for example, Wang and Riviere, *Molecular Therapy Oncolytics,* 3:16015 (2016).

In some cases, the immune cells (e.g., T cells) that include, for example, a vector containing a nucleic acid encoding the alpha chain and/or beta chain polypeptides of a TCR provided herein, can be cryopreserved for use at a later time. For example, the cells can be cryopreserved with dimethylsulfoxide (DMSO) and human serum albumin (HSA). In some cases, the cells can be cryopreserved with a balanced crystalloid solution (e.g., Plasma-Lyte 148), DMSO, and HSA.

In some cases, a nucleic acid provided herein, a vector provided herein, or an immune cell provided herein can be formulated as a pharmaceutical composition for administration to a mammal (e.g., a human) to treat a disorder, disease, or condition. For example, immune cells that comprise an exogenous TCR provided herein having affinity for an ATM peptide and/or an exogenous TCR provided herein having affinity for an ARID1A peptide can be formulated and used for cell therapy, e.g., adoptive cell therapy. In some cases, a nucleic acid, a vector, or an immune cell provided herein can be formulated for administration to a mammal (e.g., a human to treat cancer). In some cases, a pharmaceutical composition provided herein can include a pharmaceutically acceptable carrier such as a buffer, a salt, a surfactant, a sugar, a tonicity modifier, or combinations thereof. See, for example, Gervasi, et al., *Eur. J. Pharmaceutics and Biopharmaceutics*, Volume 131, pages 8-24 (2018). Examples of pharmaceutically acceptable carriers that can be used to make a pharmaceutical composition provided herein include, without limitation, water, lactic acid, citric acid, sodium chloride, sodium citrate, sodium succinate, sodium phosphate, a surfactant (e.g., polysorbate 20, polysorbate 80, or poloxamer 188), dextran 40, or a sugar (e.g., sorbitol, mannitol, sucrose, dextrose, or trehalose), or combinations thereof. For example, a pharmaceutical composition designed to include immune cells comprising an exogenous TCR provided herein having affinity for an ATM peptide (or nucleic acid or vector encoding an alpha and/or beta chain of a TCR) or an exogenous TCR provided herein having affinity for an ARID1A peptide (or nucleic acid or vector encoding an alpha and/or beta chain of a TCR) can be formulated to include a buffer (e.g., an acetate, citrate, histidine, succinate, phosphate, hydroxymethylaminomethane (Tris), or Plasma-lyte buffer).

In some cases, when a pharmaceutical composition is formulated to include immune cells, the formulation contains a sufficient number of cells to deliver about $1\times10^5$ to about $1\times10^{10}$ cells/kg body weight to the mammal. For example, the formulation contains a sufficient number of cells to deliver $1\times10^5$ to about $1\times10^9$ cells/kg body weight, $1\times10^5$ to about $1\times10^8$ cells/kg body weight, $2\times10^5$ to about $2\times10^6$ cells/kg body weight, or $1\times10^6$ to about $1\times10^7$ cells/kg body weight to the mammal.

In some cases, when a pharmaceutical composition is formulated to include one or more nucleic acids (e.g., vectors such as viral vectors) encoding an alpha and/or beta chain of a TCR provided herein, any appropriate concentration of the nucleic acid can be used. For example, a pharmaceutical composition provided herein can be formulated to be a liquid that includes from about 0.5 mg to about 500 mg (e.g., from about 1 mg to about 500 mg, from about 10 mg to about 500 mg, from about 50 mg to about 500 mg, from about 100 mg to about 500 mg, from about 0.5 mg to about 250 mg, from about 0.5 mg to about 150 mg, from about 0.5 mg to about 100 mg, from about 0.5 mg to about 50 mg, from about 1 mg to about 300 mg, from about 2 mg to about 200 mg, from about 10 mg to about 300 mg, from about 25 mg to about 300 mg, from about 50 mg to about 150 mg, or from about 150 mg to about 300 mg) of a nucleic acid (e.g., a vector such as a viral vector) encoding an alpha and/or beta chain of a TCR per mL. In another example, a pharmaceutical composition provided herein can be formulated to be a solid or semi-solid that includes from about 0.5 mg to about 500 mg (e.g., from about 1 mg to about 500 mg, from about 10 mg to about 500 mg, from about 50 mg to about 500 mg, from about 100 mg to about 500 mg, from about 0.5 mg to about 250 mg, from about 0.5 mg to about 150 mg, from about 0.5 mg to about 100 mg, from about 0.5 mg to about 50 mg, from about 1 mg to about 300 mg, from about 10 mg to about 300 mg, from about 25 mg to about 300 mg, from about 50 mg to about 150 mg, or from about 150 mg to about 300 mg) of a nucleic acid (e.g., a vector such as a viral vector) encoding a an alpha and/or beta chain of a TCR.

A pharmaceutical composition provided herein can be in any appropriate form. For example, a pharmaceutical composition provided herein can designed to be a liquid, a semi-solid, or a solid. In some cases, a pharmaceutical composition provided herein can be a liquid solution (e.g., an injectable and/or infusible solution), a dispersion, a suspension, a tablet, a pill, a powder, a microemulsion, a liposome, or a suppository. In some cases, a pharmaceutical composition provided herein can be lyophilized. In some cases, a pharmaceutical composition provided herein (e.g., a pharmaceutical composition that includes one or more nucleic acids provided herein) can be formulated with a carrier or coating designed to protect against rapid release. For example, a pharmaceutical composition provided herein can be formulated as a controlled release formulation or as a regulated release formulation as described elsewhere (U.S. Patent Application Publication Nos. 2019/0241667; 2019/0233522; and 2019/0233498).

This document also provides methods for administering a composition (e.g., a pharmaceutical composition provided herein) containing immune cells that include an exogenous TCR provided herein having affinity for an ATM peptide (or nucleic acid or vector encoding an alpha and/or beta chain of such a TCR), an exogenous TCR provided herein having affinity for an ARID1A peptide (or nucleic acid or vector encoding an alpha and/or beta chain of such a TCR), or both a TCR having affinity for a mutant ATM peptide and a TCR having affinity for an ARID1A peptide (or nucleic acid or vector encoding an alpha and/or beta chain of both of such TCRs) to a mammal (e.g., a human). For example, a composition (e.g., a pharmaceutical composition provided herein) containing immune cells that include an exogenous TCR having affinity for an ATM peptide, an exogenous TCR having affinity for an ARID1A peptide, or both a TCR having affinity for a mutant ATM peptide and a TCR having affinity for an ARID1A peptide provided herein (or nucleic acid or vector encoding an alpha and/or beta chain of one or both of such TCRs) can be administered to a mammal (e.g., a human) in need thereof to treat a disorder, disease, or condition. Any appropriate method can be used to administer a composition (e.g., a pharmaceutical composition provided herein) to a mammal (e.g., a human). For example, a composition (e.g., a pharmaceutical composition provided herein) containing immune cells that include an exogenous TCR provided herein having affinity for an ATM peptide and/or an exogenous TCR provided herein having affinity for an ARID1A peptide (or nucleic acid or vector encoding an alpha and/or beta chain of one or both of such TCRs) can be administered to a mammal (e.g., a human) intravenously (e.g., via an intravenous injection or infusion), subcutaneously (e.g., via a subcutaneous injection), intraperitoneally (e.g., via an intraperitoneal injection), orally, via inhalation, or intramuscularly (e.g., via intramuscular injection). In some cases, the route and/or mode of administration of a composition (e.g., a pharmaceutical composition provided herein) containing immune cells that include an exogenous TCR provided herein (or nucleic acid or vector encoding an alpha and/or beta chain of such a TCR) can be adjusted for the mammal being treated.

Effective doses of a composition containing immune cells that include an exogenous TCR provided herein having affinity for an ATM peptide, and/or an exogenous TCR provided herein having affinity for an ARID1A peptide (or nucleic acid or vector encoding an alpha and/or beta chain of one or both of such TCRs), or both a TCR having affinity for a mutant ATM peptide and a TCR having affinity for an ARID1A peptide can vary depending on the severity of the disorder, the route of administration, the age and general health condition of the subject, excipient usage, the possibility of co-usage with other therapeutic treatments such as use of other agents, and the judgment of the treating physician.

In some cases, an effective amount of a composition containing immune cells comprising an exogenous TCR provided herein having affinity for an ATM peptide and/or an exogenous TCR provided herein having affinity for an ARID1A peptide (or nucleic acid or vector encoding an alpha and/or beta chain of one or both of such TCRs) can be an amount that reduces the activity of the target antigen within a mammal without producing significant toxicity to the mammal. For example, an effective amount of immune cells that comprise an exogenous TCR provided herein can be from about $1\times10^5$ to about $1\times10^{10}$ cells/kg body weight. For example, the cells can be administered to the mammal at a range of $1\times10^5$ to about $1\times10^9$ cells/kg body weight, $1\times10^5$ to about $1\times10^8$ cells/kg body weight, $2\times10^5$ to about $2\times10^6$ cells/kg body weight, $1\times10^6$ to about $1\times10^7$ cells/kg body weight.

The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the condition (e.g., cancer) may require an increase or decrease in the actual effective amount administered.

The frequency of administration of immune cells that include an exogenous TCR provided herein having affinity for an ATM peptide and/or an exogenous TCR provided herein having affinity for an ARID1A peptide (or nucleic acid or vector an alpha and/or beta chain of one or both of such TCRs) can be any amount that maintains a fairly steady state of reduced target antigen activity within a mammal without producing significant toxicity to the mammal. For example, the frequency of administration of immune cells provided herein can be from about twice daily to about once a week. In some cases, the frequency of administration of immune cells provided herein can be daily. The frequency of administration of immune cells provided herein can remain constant or can be variable during the duration of treatment. A course of treatment with a composition containing immune cells provided herein can include rest periods. For example, a composition containing immune cells provided herein can be administered daily over a two-week period followed by a one-week rest period, and such a regimen can be repeated multiple times. As with the effective amount, various factors can influence the actual frequency of administration used for a particular application. For example, the effective amount, duration of treatment, use of multiple treatment agents, route of administration, and severity of the condition (e.g., cancer) may require an increase or decrease in administration frequency.

An effective duration for administering a composition containing immune cells that include an exogenous TCR provided herein having affinity for an ATM peptide, an exogenous TCR provided herein having affinity for an ARID1A peptide, or both a TCR having affinity for a mutant ATM peptide and a TCR having affinity for an ARID1A peptide (or nucleic acid or vector encoding the alpha and/or beta chains of one or both of such TCRs) can be any appropriate duration that reduces the activity of the target antigen within a mammal without producing significant toxicity to the mammal. In some cases, the effective duration can vary from several weeks to several years (e.g., 5, 10, 15, or more years). Multiple factors can influence the actual effective duration used for a particular treatment. For example, an effective duration can vary with the frequency of administration, effective amount, use of multiple treatment agents, route of administration, and severity of the condition being treated.

In some cases, a composition containing immune cells that include an exogenous TCR provided herein having affinity for an ATM peptide, an exogenous TCR provided herein having affinity for an ARID1A peptide, or both a TCR having affinity for a mutant ATM peptide and a TCR having affinity for an ARID1A peptide (or nucleic acid or vector encoding the alpha and/or beta chains of one or both of such TCRs) can be administered as part of a combination treatment, such as simultaneously with or sequentially with, in any order, another therapeutic agent, such as a cytokine (e.g., IL-2), antibody (e.g., tocilizumab, which blocks IL-6 activity), an immune checkpoint inhibitor (e.g., one or more of an anti-PD-1 antibody, an anti-PDL-1 antibody, or an anti-CTLA-4 antibody), or a chemotherapeutic agent.

The invention will be further described in the following examples, which do not limit the scope of the invention described in the claims.

EXAMPLES

To confirm the specificity and activity of nucleic acid encoding TCRs against ATM and ARID1A, each of the codon optimized nucleic acids were introduced into donor T cells. The chimeric TCR-transduced T cells (TRBV9*01+TRAV14/DV4 chimeric TCR) were co-cultured with dendritic cells expressing wildtype ATM or mutated forms of ATM (G2695V, G2695A, G2695C, or G2695S). The chimeric TCR-transduced T cells (TRBV25-1+TRAV20 chimeric TCR) were co-cultured with dendritic cells expressing wildtype ARID1A or ARID1A H1960fs. After overnight incubation, the supernatant was assessed for production of interferon-gamma using an ELISA. It was found that the introduced nucleic acids encoding TCRs conferred mutation reactivity without reactivity against the wild-type form of ATM and ARID1A. See FIGS. 9A and 9B, respectively.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated human immune cell comprising an exogenous T cell receptor (TCR) having affinity for a human Ataxia-Telangiesctasia Mutated (ATM) peptide comprising a valine, alanine, cysteine, or serine at position 2695 in the context of HLA A*03:01, said exogenous TCR comprising an alpha chain and a beta chain, said alpha chain comprising the amino acid sequences set forth in SEQ ID NO:10, SEQ ID NO: 11, and SEQ ID NO: 12, and said beta chain comprising the amino acid sequences set forth in SEQ ID NO:1, SEQ ID NO: 2, and SEQ ID NO:3.

2. The immune cell of claim 1, wherein said alpha chain comprises an amino sequence having at least 80 percent identity to the amino acid sequence set forth in SEQ ID NO: 18 or SEQ ID NO:22.

3. The immune cell of claim 1, wherein said beta chain comprises an amino acid sequence having at least 80 percent identity to the amino acid sequence set forth in SEQ ID NO:9 or SEQ ID NO:20.

4. The immune cell of claim 1, wherein said immune cell is a T cell.

5. The immune cell of claim 4, wherein expression of the endogenous TCR alpha and beta chain coding sequences are downregulated in said T cell.

6. The immune cell of claim 1, wherein said human ATM peptide comprises a valine at position 2695.

7. A nucleic acid molecule comprising (a) a nucleic acid sequence encoding an alpha chain of a TCR having affinity for a human ATM peptide comprising a valine, alanine, cysteine, or serine at position 2695 in the context of HLA A*03:01 and (b) a nucleic acid sequence encoding a beta chain of said TCR, said alpha chain comprising the amino acid sequences set forth in SEQ ID NO:10, SEQ ID NO:11, and SEQ ID NO: 12, and said beta chain comprising the amino acid sequences set forth in SEQ ID NO:1, SEQ ID NO: 2, and SEQ ID NO: 3.

8. The nucleic acid of claim 7, wherein said nucleic acid is a vector.

9. The nucleic acid of claim 8, wherein said vector is a viral vector.

10. A method of making an immune cell comprising an exogenous TCR having affinity for a human ATM peptide comprising a valine, alanine, cysteine, or serine at position 2695 in the context of HLA A*03:01, said method comprising introducing, into said immune cell, nucleic acid, wherein said exogenous TCR is expressed from said nucleic acid in said immune cell, wherein said nucleic acid comprises:

(a) a nucleic acid sequence encoding an alpha chain of said TCR and a nucleic acid sequence encoding a beta chain of said TCR having, said alpha chain comprising the amino acid sequences set forth in SEQ ID NO:10, SEQ ID NO: 11, and SEQ ID NO: 12, and said beta chain comprising the amino acid sequences set forth in SEQ ID NO:1, SEQ ID NO: 2, and SEQ ID NO:3.

11. The method of claim 10, wherein said immune cell is a T cell.

12. An isolated immune cell comprising nucleic acid, said immune cell comprising an exogenous TCR having affinity for a human ATM peptide comprising a valine, alanine, cysteine, or serine at position 2695 in the context of HLA A*03:01, wherein said nucleic acid comprises:

(a) a nucleic acid sequence encoding an alpha chain of said TCR and a nucleic acid sequence encoding a beta chain of said TCR, said alpha chain comprising the amino acid sequences set forth in SEQ ID NO:10, SEQ ID NO: 11, and SEQ ID NO: 12, and said beta chain comprising the amino acid sequences set forth in SEQ ID NO:1, SEQ ID NO: 2, and SEQ ID NO: 3.

13. A method for providing a mammal with cells comprising a TCR having affinity for a human ATM peptide comprising a valine, alanine, cysteine, or serine at position 2695 in the context of HLA A*03:01, said method comprising delivering, to said mammal, nucleic acid, wherein said nucleic acid is expressed in cells of said mammal, wherein said nucleic acid comprises:

(a) a nucleic acid sequence encoding an alpha chain of said TCR and a nucleic acid sequence encoding a beta chain of said TCR, said alpha chain comprising the amino acid sequences set forth in SEQ ID NO:10, SEQ ID NO:11, and SEQ ID NO: 12, and said beta chain comprising the amino acid sequences set forth in SEQ ID NO:1, SEQ ID NO: 2, and SEQ ID NO:3.

14. A method for treating a mammal having cancer, said method comprising administering, to said mammal, (a) a population of cells or (b) nucleic acid, wherein said population of cells comprises at least one immune cell comprising said nucleic acid, wherein said immune cell comprises an exogenous TCR having affinity for a human ATM peptide comprising a valine, alanine, cysteine, or serine at position 2695 in the context of HLA A*03:01, and wherein said nucleic acid comprises:

(a) a nucleic acid sequence encoding an alpha chain of said TCR and a nucleic acid sequence encoding a beta chain of said TCR, said alpha chain comprising the amino acid sequences set forth in SEQ ID NO:10, SEQ ID NO: 11, and SEQ ID NO: 12, and said beta chain comprising the amino acid sequences set forth in SEQ ID NO:1, SEQ ID NO: 2, and SEQ ID NO:3.

15. The method of claim 14, wherein said mammal is a human.

16. The method of claim 15, wherein said cells are autologous to said human.

* * * * *